United States Patent [19]

Bernady et al.

[11] 4,054,604

[45] Oct. 18, 1977

[54] AMIDE DERIVATIVES OF 9-oXo-13-TRANS-PROSTENOIC ACID

[75] Inventors: Karel Francis Bernady; Middleton Brawner Floyd, Jr., both of Suffern; John Frank Poletto, Nanuet, all of N.Y.; Robert Eugene Schaub, Upper Saddle River; Martin Joseph Weiss, Oradell, both of N.J.

[73] Assignee: American Cyanamid Company, Stamford, Conn.

[21] Appl. No.: 685,943

[22] Filed: May 13, 1976

Related U.S. Application Data

[60] Division of Ser. No. 432,264, Jan. 10, 1974, Pat. No. 3,981,868, which is a continuation-in-part of Ser. No. 365,806, May 31, 1973, abandoned, which is a continuation of Ser. No. 162,712, July 14, 1971, abandoned.

[51] Int. Cl.$^2$ .................... C07C 103/19; A61K 31/16
[52] U.S. Cl. .......................... 260/557 R; 260/558 H; 260/558 P; 260/559 R; 260/559 H; 260/559 T
[58] Field of Search .......... 260/557 R, 557 H, 468 D, 260/514 D, 558 R, 558 H, 558 P, 558 S, 559 R, 559 T, 559 H

[56] References Cited

U.S. PATENT DOCUMENTS

| 3,751,463 | 8/1973 | Caton | 260/557 R |
|---|---|---|---|
| 3,853,951 | 12/1974 | Bernady et al. | 260/514 D X |
| 3,880,883 | 4/1975 | Caton et al. | 260/557 R X |
| 3,888,905 | 6/1975 | Miyano | 260/514 D X |
| 3,923,864 | 12/1975 | Nelson | 260/514 D X |
| 3,935,261 | 1/1976 | Caton et al. | 260/557 H X |
| 3,954,741 | 5/1976 | Schaaf et al. | 260/557 R X |
| 3,954,833 | 5/1976 | Magerlein | 260/514 D X |

*Primary Examiner*—Daniel E. Wyman
*Assistant Examiner*—Thomas A. Waltz
*Attorney, Agent, or Firm*—Denis A. Polyn

[57] ABSTRACT

This disclosure describes homologues, analogues, congeners, and derivatives of 9-oxo-13-trans-prostenamide and of 9-hydroxy-13-trans-prostenamide, having antimicrobial activity and prostaglandin-like hypotensive activity.

19 Claims, No Drawings

AMIDE DERIVATIVES OF 9-OXO-13-TRANS-PROSTENOIC ACID

CROSS REFERENCE TO RELATED APPLICATIONS

This is a division of Ser. No. 432,264, filed Jan. 10, 1974, now U.S. Pat. No. 3,981,868, which is a continuation-in-part of Ser. No. 365,806, filed May 31, 1973, which is a continuation of Ser. No. 162,712, filed July 14, 1971, both now abandoned.

BRIEF SUMMARY OF THE INVENTION

This invention relates to new organic compounds and, more particularly, is concerned with a class of compounds related to the natural prostaglandins. The novel compounds of the present inventon may be represented by the following general formulae:

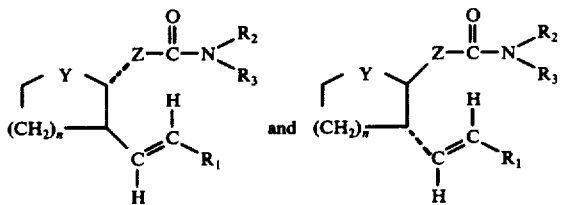

wherein n is the integer 1 or 2; Y is a divalent radical selected from the group consisting of

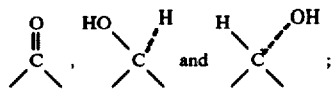

Z is a divalent radical selected from the group consisting of $$-(CH_2)_m-, \quad -CH_2-CH\overset{cis}{=}CH-(CH_2)_p-,$$

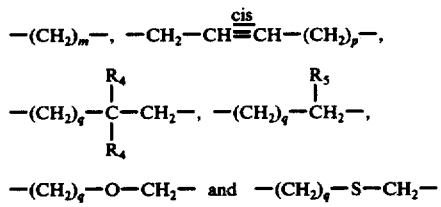

$$-(CH_2)_q-O-CH_2- \quad \text{and} \quad -(CH_2)_q-S-CH_2-$$

wherein m is an integer from 1 to 8, inclusive, p is an integer from 2 to 4, inclusive, q is an integer from 3 to 6, inclusive, $R_4$ is a lower alkyl group having up to carbon atoms, and $R_5$ is a lower alkyl group, phenyl or fluorine; $R_1$ is selected from the group consisting of (a) a staight chain alkyl group having from 3 to 10 carbon atoms, (b) a straight chain alkyl group having from 3 to 6 carbon atoms and having one branched lower alkyl group, (c) a straight chain alkenyl group having from 3 to 6 carbon atoms, (d) a straight chain ω-haloalkyl group having from 3 to 6 carbon atoms, (e) a straight chain ω-phenylalkyl group having from 1 to 4 carbon atoms in the chain; (f) a straight chain ω-(cycloalkyl)alkyl group having from 1 to 4 carbon atoms in the chain and from 5 to 7 carbon atoms in cycloalkyl, and (g) moieties of the formulae:

wherein p and $R_4$ are as hereinabove defined; $R_2$ is selected from the group consisting of hydrogen, lower alkyl, lower alkenyl, lower alkynyl, cyclohexyl, phenyl lower alkyl and ω-hydroxy lower alkyl; $R_3$ is selected from the group consisting of hydrogen, lower alkyl, hydroxy, ω-di(lower alkyl)amino lower alkyl, lower alkenyl, lower alkynyl, cyclohexyl, phenyl, trifluoromethylphenyl, di(lower alkyl)aminophenyl, chlorophenyl, lower alkylphenyl, pyridyl, phenyl lower alkyl, pyridyl lower alkyl, ω-hydroxy lower alkyl, ω-lower alkoxy lower alkyl, ω-di(lower alkyl)amino lower alkyl, ω-piperidino lower alkyl, ω-pyrrolidino lower alkyl, ω-morpholino lower alkyl, amino, di(lower alkyl)amino, N-piperidyl, N-hexamethyleneimino, N-morpholino, N-anilino and 4-lower alkyl-1-piperazino; and $R_2$ and $R_3$ taken together with the associated N(itrogen) is selected from the group consisting of pyrrolidino, piperidino, morpholino, hexamethyleneimino, 4-phenylpiperidino, 4-lower alkyl-1-piperazino, 4-phenylpiperazino, 3-pyrrolinyl, $\Delta^3$-piperidino, 3-azabicyclo[3.2.2]nonyl, N,N'-bis-di(lower alkyl)aminophenylureido and 4,4-spirocyclohexylpiperidyl.

Suitable lower alkyl and lower alkoxy groups contemplated by the present invention are those having up to four carbon atoms such as, for example, methyl, ethyl, isopropyl, sec-butyl, methoxy, ethoxy, n-propoxy, tert-butoxy, etc. Halo is exemplified by chloro, bromo or iodo whereas pyridyl may be α-, β-, or γ-pyridyl. Suitable phenyl lower alkyl and pyridyl lower alkyl groups thus may be, for example, benzyl, α-phenylethyl, β-phenylethyl, γ-phenylpropyl, α-pyridylmethyl, γ-pyridylmethyl, α-(β-pyridyl)ethyl, β-(γ-pyridyl)ethyl, γ-(α-pyridyl)propyl and the like. Appropriate ω-hydroxy lower alkyl and and ω-lower alkoxy lower alkyl groups thus may be hydroxymethyl, β-hydroxyethyl, γ-hydroxypropyl, γ-hydroxy-sec-butyl, methoxymethyl, β-ethoxyethyl, γ-ethoxypropyl, γ-(n-propoxy)-n-butyl, and the like. Suitable lower alkenyl and lower alkynyl groups contemplated by the present invention are those having up to 4 carbon atoms and attached to the nitrogen atom via a carbon atom that is not part of an unsaturated bond such as, for example, allyl, 2-butenyl, 3-butenyl, isobutenyl, 2-butynyl, propargyl, etc.

In the above general formulae, the side chains at the 8-position and the 12-position are in trans configuration. When the side chain is attached to C-8 or C-12 by a ― bond, then it is behind the plane of the paper. When the side chain is attached to C-8 or C-12 by a ― bond, then it is in front of the plane of the paper. Thus, all such isomers of trans configuration are included within the purview of the present invention.

The novel compounds of the present invention having a basic nitrogen atom in the $R_3$ substituent form acid-addition salts with a variety of pharmacologically acceptable organic and inorganic salt-forming reagents. Thus, acid-addition salts, formed by admixture of the base with an equivalent of an acid, suitably in a neutral solvent, are formed with such acids as sulfuric, phosphoric, hydrochloric, hydrobromic, citric, tartaric, acetic and related acids. For purposes of this invention, these bases are equivalent to their non-toxic acid-addition salts.

DETAILED DESCRIPTION OF THE INVENTION

The prostaglandins are a family of closely related compounds which have been obtained from various animal tissues, and which stimulate smooth muscle, lower arterial blood pressure, antagonize epinephrine-induced mobilization of free fatty acids, and have other pharmacological and autopharmacological effects in mammals. See Bergström et al., J. Biol. Chem. 238, 3555 (1963) and Horton, Experientia 21, 113 (1965) and references cited therein. All of the so-called natural prostaglandins are derivatives of prostanoic acid:

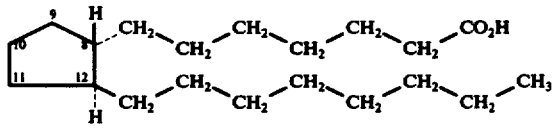

The hydrogen atoms attached to C-8 and C-12 are in trans configuration.

The novel compounds of the present invention may be readily prepared from 2-carbethoxycyclopentanone or 2-carbethoxycyclohexanone in accordance with the reaction schemes set forth in Flowsheets A through G. In particular, the requisite 2-(ω-carbethoxyalkyl)cycloalk-2-en-1-one intermediates (VIII) may be prepared in accordance with the following reaction scheme:

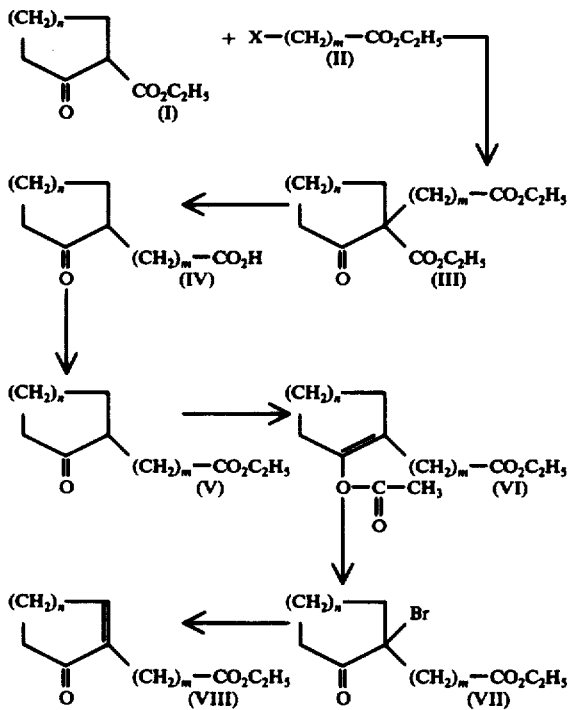

wherein m and n are as hereinbefore defined and X is iodo or bromo. In accordance with this reaction scheme, the cycloalk-2-en-1-ones (VIII) are developed by first converting 2-carbethoxycyclopentanone or 2-carbethoxycyclohexanone (I) to the sodium enolates thereof by means of sodium hydride in dimethoxyethane and then treating the sodium enolate with an ethyl ω-haloalkanoate (II). There is thus obtained the corresponding 2-carbethoxy-2-(ω-carbethoxyalkyl)cycloalkanone (III) which is then hydrolyzed and decarboxylated to afford the 2-(ω-carboxyalkyl)cycloalkanone (IV). This acid is then esterified with ethanol whereby the 2-(ω-carbethoxyalkyl)cycloalkanone (V) is obtained. The reaction conditions for carrying out the above sequence of reactions are well known in the art. The conversion of the cycloalkanone (V) to the enol acetate (VI) is effected by heating with acetic anhydride in the presence of p-toluenesulfonic acid. Preparation of the enol acetate (VI) usually requires heating for a period of from about eight to thirty-six hours. During this period, it is preferable to allow by-product acetic acid to distill out in order to force the reaction to completion. The bromination of the enol acetates (VI) to the 2-bromocycloalkanones (VII) is preferably carried out in a two phase system as follows. A solution of bromine in chloroform is added to a rapidly stirred mixture of a solution of the enol acetate (VI) in chloroform and an aqueous solution of an acid acceptor such as calcium carbonate or soda ash. This addition is carried out at 0°–5° C. over a period of about half an hour, stirring is continued for an additional period of about half an hour to a few hours, and the product (VII) is then isolated by standard procedures. The dehydrobromination of the 2-bromocycloalkanones (VII) is preferably carried out in dimethylformamide with a mixture of lithium bromide and lithium carbonate at the reflux temperature for a period of about 30 minutes to an hour or so. The so formed cycloalk-2-en-1-ones (VIII) are also isolated by standard procedures well known in the art. Substitution of X—(CH$_2$)$_q$—C(R$_4$)$_2$—CH$_2$—CO$_2$C$_2$H$_5$ for (II) in Flowsheet A and carrying through the sequence of transformations illustrated therein is productive of the following cycloalk-2-en-1-one (VIIIa):

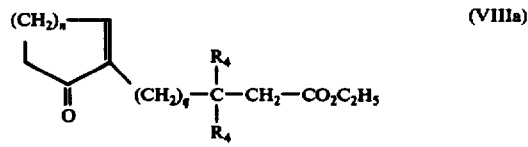

wherein X, n, q and R$_4$ are as hereinabove defined.

The required cycloalk-2-en-1-one intermediates of general structure (XVI), wherein the side-chain has a lower alkyl group, a phenyl group, or a fluorine atom alpha to the carbethoxy function, may be prepared in accordance with the following reaction scheme:

FLOWSHEET B

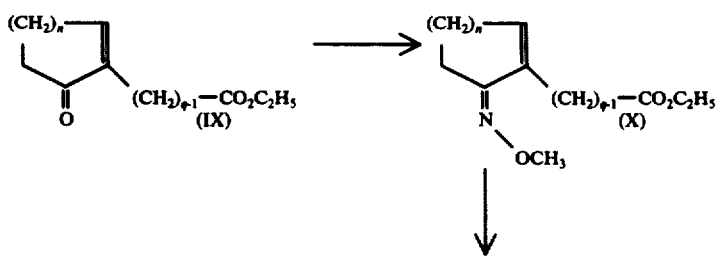

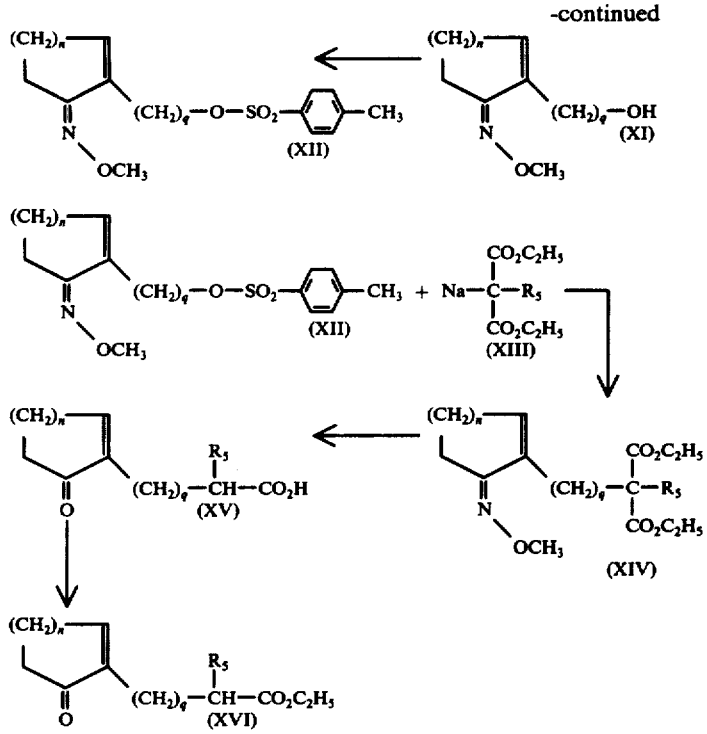

wherein $n$, $q$ and $R_5$ are as hereinabove defined. In accordance with this reaction scheme, the 2-($\omega$-carbethoxyalkyl)cycloalk-2-en-1-ones (IX) are converted to the corresponding 1-methoximino-2-($\omega$-carbethoxyalkyl)-2-cycloalkenes (X) by treatment with methoxyamine. With the ring carbonyl function thus blocked it is possible to effect a preferential reduction of the ester group by treatment with diisobutylaluminum hydride. The resulting alcohol (XI) is converted to a tosylate derivative (XII), which undergoes displacement on treatment with the sodium salt of a mono-substituted diethyl malonate (XIII) to provide the disubstituted malonate derivatives (XIV). Hydrolysis and decarboxylation as well as concomittant cleavage of the methoximino blocking group provides the desired 2-($\omega$-carboxy-$\alpha$-substituted-alkyl)cycloalk-2-en-1-ones (XV), which are readily converted to the corresponding ester (XVI) by the usual Fisher procedure.

The requisite 2-($\omega$-carbethoxy-3-oxa-alkyl)cycloalk-2-en-1-ones (XXII) and 2-($\omega$-carbethoxy-3-thia-alkyl)-cycloalk-2-en-1-ones (XXVI) may be prepared in accordance with the reaction schemes of Flowsheet C, wherein $n$ and $q$ are as hereinbefore defined.

FLOWSHEET C

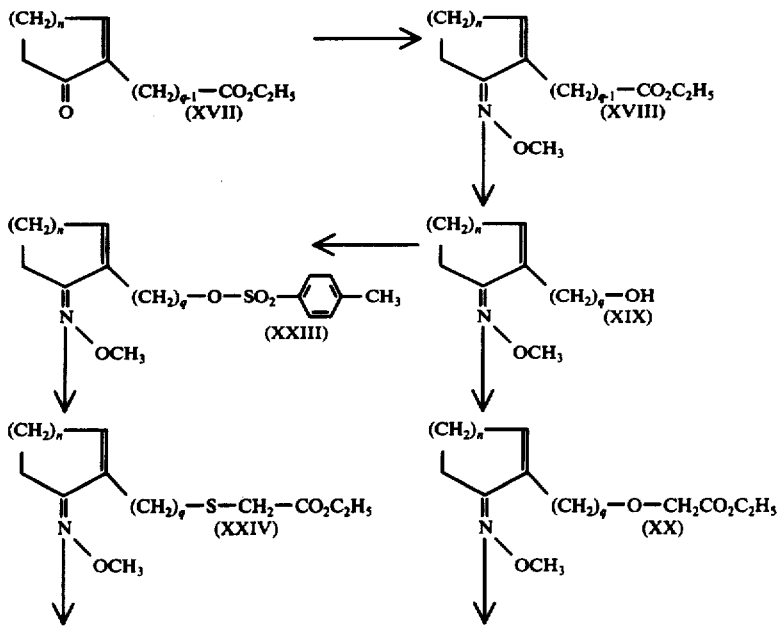

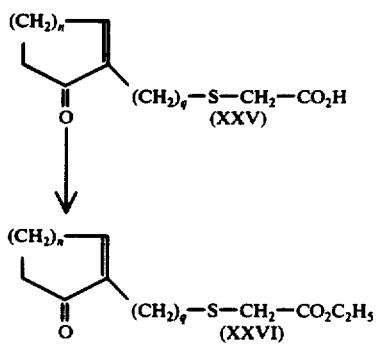

(XXV)

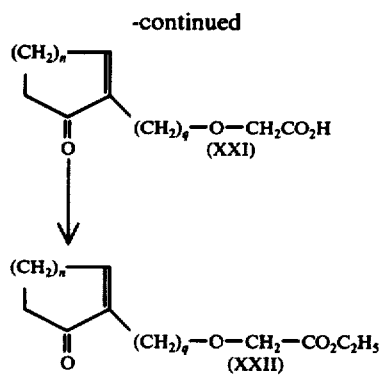

(XXI)

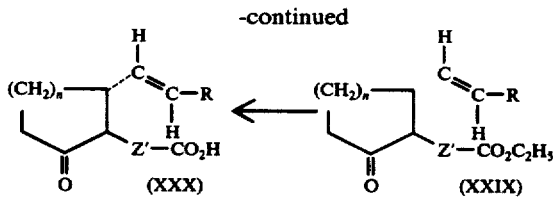

(XXVI)

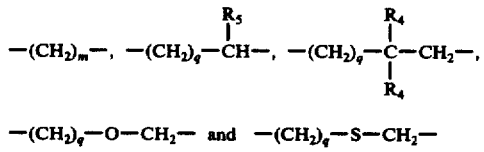

(XXII)

In accordance with the reaction scheme shown in Flowsheet C, for the preparation of the oxa derivative (XXII), an appropriate 2-(ω-carbethoxyalkyl)cyloalk-2-en-1-one (XVII) is converted to the corresponding methoxime (XVIII), the ester function of which is then preferentially reduced with diisobutylaluminum hydride to afford the methoxime alcohol (XIX). The alcohol (XIX) is converted on treatment with n-butyl lithium to the lithio alcoholate, which then is O-alkylated by reaction with ethyl bromoacetate to provide (XX). Hydrolysis with acetone-aqueous hydrochloric acid furnishes the deblocked keto-acid (XXI), which is then re-esterified with ethanol in the presence of p-toluenesulfonic acid to give the required 2-(ω-carbethoxy-3-oxa-alkyl)cycloalk-2-en-1-one (XXII). O-Alkylaytion can also be accomplished by treatment of the lithio alcoholate of (XIX) with sodium or other metal salt of bromoacetic acid, in which case the free carboxylic acid corresponding to ester (XX) is obtained. Hydrolysis as for (XX) provides the keto acid (XXI).

The preparation of the thia derivatives (XXVI), proceeds from the intermediate alcohol (XIX), which after conversion to the tosylate intermediate (XXIII) and reaction with the sodium salt of ethyl mercaptoacetate furnishes intermediate (XXIV). Deblocking of XXIV with acetone-aqueous hydrochloric acid provides the keto-acid (XXV), which on re-esterification with ethanol gives the required 2-(ω-carbethoxy-3-thia-alkyl)cycloalk-2-en-1-ones (XXVI).

Certain of the intermediates for the novel compounds of the present invention may be obtained in accordance with the following reaction scheme of Flowsheet D. Although a racemic mixture of isomers of trans configuration at C-8 and C-12 is obtained, only one such isomer is indicated for the sake of convenience. Likewise in Flowsheets E and F, only one such isomer is shown for the sake of convenience.

FLOWSHEET D

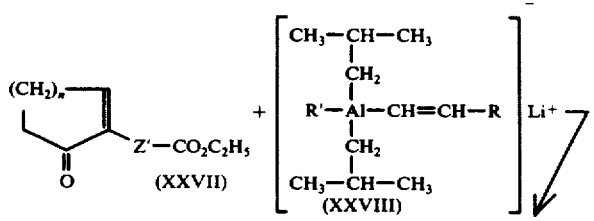

wherein Z' is a divalent radical selected from the group consisting of $$-(CH_2)_m-, \quad -(CH_2)_q-CH-, \quad -(CH_2)_q-C-CH_2-,$$
$$\phantom{-(CH_2)_m-, \quad -(CH_2)_q-}R_5 \phantom{-, \quad -(CH_2)_q-}R_4$$
$$\phantom{-(CH_2)_m-, \quad -(CH_2)_q-CH-, \quad -(CH_2)_q-}R_4$$

$$-(CH_2)_q-O-CH_2- \text{ and } -(CH_2)_q-S-CH_2-$$

and $n$, $m$, $q$, $R_4$ and $R_5$ are as hereinabove defined; R' is a lower alkyl group, preferably methyl or n-butyl; and R is a straight chain alkyl group having from 3 to 10 atoms, a straight chain alkyl group having from 2 to 6 carbon atoms and having one branched lower alkyl group, a straight chain alkenyl group having from 3 to 6 carbon atoms, a straight chain ω-chloroalkyl group having from 3 to 6 carbon atoms, an ω-phenylalkyl group, or an ω-(cycloalkyl)alkyl group. The compounds (XXIX) are readily prepared by the conjugate 1,4-addition of an alanate salt (XXVIII) to a 2-substituted cycloalk-2-en-1-one (XXVII). The yields for this operation are usually high and a clean product, uncontaminated with 1,2-addition product, is usually obtained. Furthermore, the transfer of the alkene group is effected with retention of the trans-configuration of the hydrogen atoms attached to the double bond, and no reaction is noted at the carbethoxy function of (XXVII). Another noteworthy aspect of this reaction is that it does not require a catalyst. The alanate salts (XXVIII) are conveniently prepared by the reaction of an appropriate 1-alkyne (R—C≡CH) with diisobutylaluminum hydride, followed by reaction with a lower alkyl lithium derivative, preferably methyl lithium or n-butyl lithium. Suitable 1-alkynes which may be thus employed are, for example, 1-pentyne, 1-hexyne, 1-decyne, 1-hendecyne, 1-dodecyne, 3-methyl-1-butyne, 1-heptyne, 1-octyne, 1-nonyne, 5-methyl-1-hexyne, 7-methyl-1-octyne, 7-methyl-1-nonyne, 3-methyl-1-octyne, 4-methyl 1-octyne, oct-5-en-1-yne, hept-5-en-1-yne, hex-4-en-1-yne, 5-chloro-1-pentyne, 6-chloro-1-hexyne, 7-chloro-1-heptyne, 8-chloro-1-octyne, etc. The reaction of the 1-alkyne with diisobutylaluminum hydride cleanly provides the trans-double bond and is preferably carried out in an inert solvent such as benzene, toluene, and the like at temperatures in the range of 40°–60° C. for several hours. The solvent is removed in vacuo and the subsequent reaction with methyl or n-butyl lithium is preferably carried out in an ether-type solvent such as diethyl ether, dibutyl ether, tetrahydrofuran, and the like. This reaction is rapid and is preferably carried out at 0°–10° C. with cooling. The conjugate 1,4-addition of the resulting alanate salt (XXVIII) to the cycloalk-2-en-1-one (XXVII) is preferably carried out at ambient temperatures for a period of 12 to 24 hours. This reaction is also best carried out in an ether-type solvent such as diethyl ether, dibutyl ether, tetrahydrofuran, and the like. The intermediate alanate-enolate adduct is then hydrolyzed in situ with dilute hydrochloric acid with cooling, and the products (XXIX) are isolated in the usual manner well known in the art. The conversion of the esters (XXIX) to the acids (XXX) is readily accomplished by mild saponification procedures such as in 0.5N aqueous-methanolic KOH at room temperature for 20–48 hours.

Other intermediates for the compounds of this invention may be prepared as illustrated by the following flowsheets. In Flowsheet E; n, p, Z and $R_4$ have the values hereinbefore defined.

FLOWSHEET E

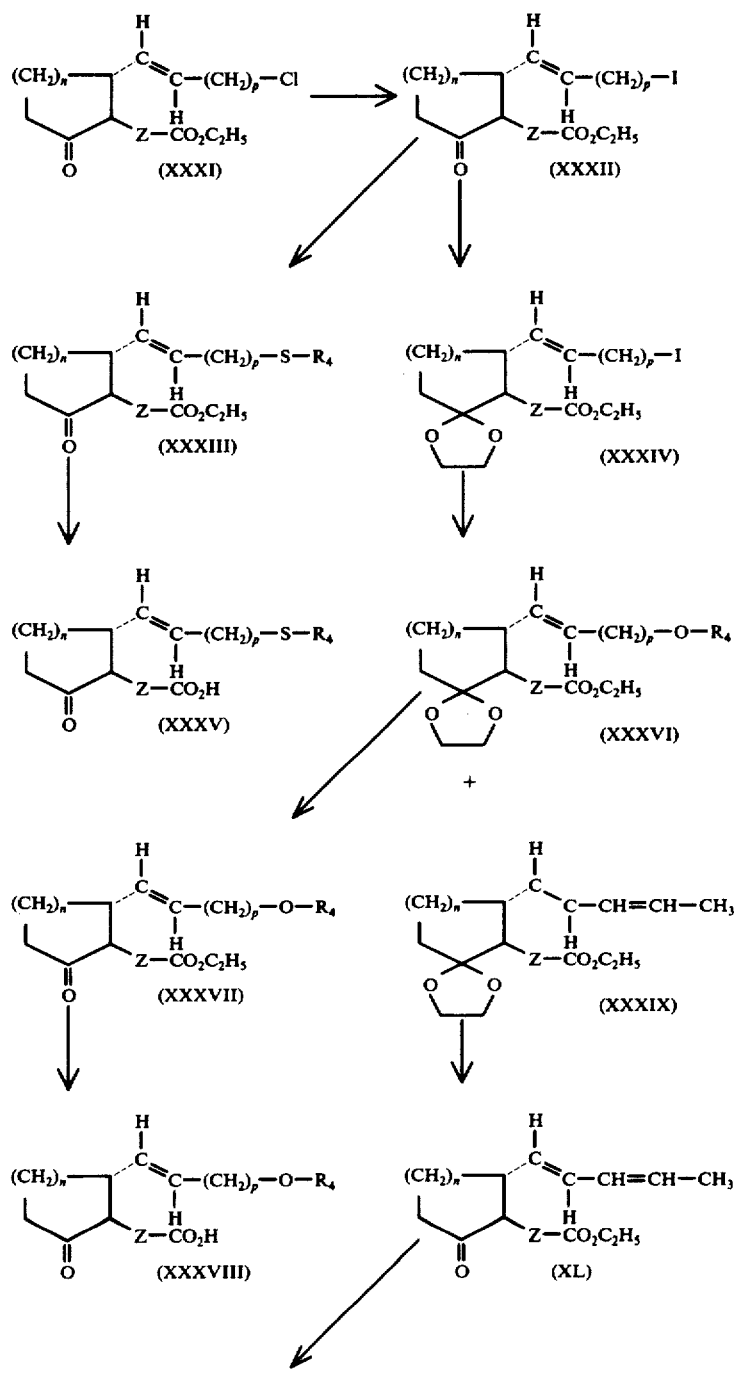

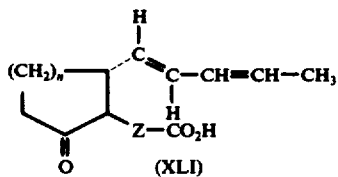

(XLI)

In Flowsheet E, treatment of the chloro derivative (XXXI) with sodium iodide provides the iodo derivative (XXXII), which on treatment with the sodium salt of an alkyl mercaptan furnishes the thia derivative (XXXIII), saponification of which gives (XXXV). For some displacement reactions it is preferable to protect the ring ketone function in (XXXII). This can be accomplished by conversion to the ethylene ketal derivatives (XXXIV). Treatment of iodo ketal (XXXIV) with a metal alkoxide provides a mixture of the oxa derivative (XXXVI) and the diene (XXXIX), separable by chromatography. Ketal hydrolysis with acetone and p-toluenesulfonic acid of these two ketal esters gives the corresponding keto ester (XXXVII) and (XL), respectively, saponification of which furnishes the keto acids (XXXVIII) and (XLI), respectively.

Additional intermediates are illustrated in Flowsheet F, wherein $n$, $p$ and $q$ are as defined hereinbefore. The group R' has all the possibilities that $R_1$ is defined above as having with the exception that a straight chain ω-haloalkyl group having from 3 to 6 carbon atoms is limited to an ω-chloroalkyl group. The synthesis of those compounds of this invention embodying at the same time Z as

and $R_1$ as an ω-haloalkyl group can be accomplished after formation of the carboxamide derivative by displacement with iodide, bromide or halide ions.

In Flowsheet F, which follows, the ring carbonyl function of the 2-(carbethoxymethyl)cyclopentanone (XLII) is blocked by conversion to the ketal (XLIII). The ester function in (XLIII) is then reduced to an aldehyde by treatment with diisobutylaluminium hydride. This reaction is preferably carried out by addition of one molecular equivalent of this reagent to a solution of ester (XLIII) in hexane or other hydrocarbon solvent, cooled to −78° C. After about 2.5 hours at this temperature the entire reaction mixture is poured quickly into aqueous excess mineral acid, and the product aldehyde (XLIV) is obtained upon immediate workup in the usual way. The aldehyde (XLIV) is then converted to (XLV) by addition of (XLIV) to the ylid prepared from an (ω-carboxyalkyl) triphenyl phosphonium bromide and two molecular equivalents of sodium hydride in anhydrous dimethylsulfoxide. The use of dimethylsulfoxide as a solvent for this reaction leads to the predominant formation of the desired cis double bond in product (XLV). The ketal blocking group in (XLV) is then cleaved by treatment with acetone and p-toluenesulfonic acid producing the keto acid (XLVI).

FLOWSHEET F

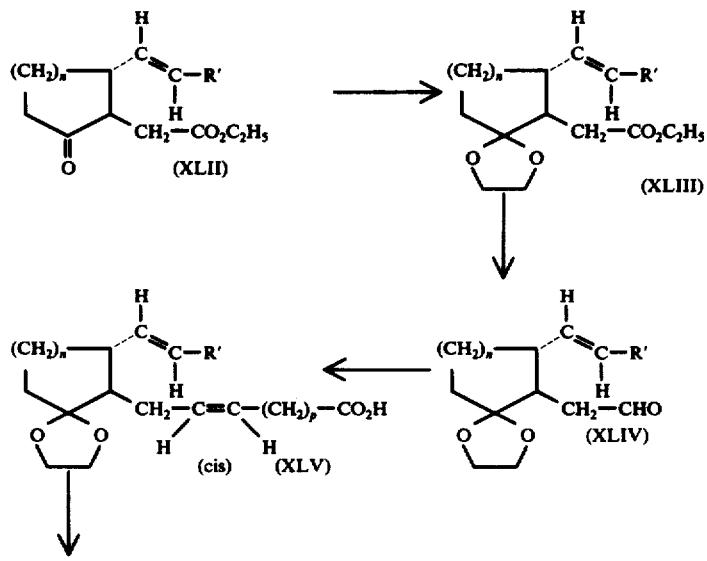

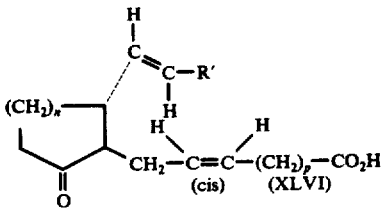

(XLVI)

The prostanoic acids described herein are convertable to the corresponding ester by first treating with thionyl chloride and then reacting the resulting acid chloride with an appropriate alcohol in the presence of an acid acceptor, e.g., triethylamine. The new ester can then undergo the transformations illustrated in Flowsheet E. Treatment of the prostanoic acid chloride with an appropriate amine in the presence of excess amine or a non-reacting acid acceptor such as triethylamine provides the novel prostanoic acid amides of this invention. These compounds can also be obtained by other methods of amide formation, well known in the art, such as reaction of the amine with mixed anhydride derivatives of the carboxylic acid. The prostenoic acid hydrazides of this invention are similarly prepared, substituting hydrazine or its appropriate derivative for the amine.

The various 9-hydroxy derivatives of this invention are prepared by reduction of the corresponding 9-keto amide. The reduction is preferably carried out in the usual manner with sodium borohydride in ethanol as a solvent. This procedure provides a mixture of the 9α- and 9β-hydroxy derivatives. (XLVII and XLVIII) which can be separated by chromatography. The stereospecific preparation of the 9α-hydroxy derivative (XLVII), wherein the 9-hydroxy group is cis to the side-chain attached to $C_8$, can be accomplished via the reduction of the 9-keto ester or acid or amide with either lithium perhydro-9b-boraphenalyl hydride [H. C. Brown and W. C. Dickason, Journ. Amer. Chem. Soc., 92, 709 (1970)] or lithium tri(sec-butyl)borohydride.

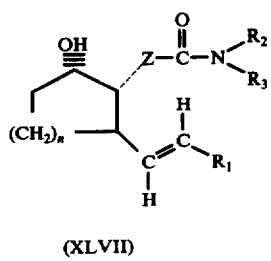

(XLVII)

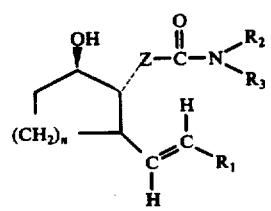

(XLVIII)

The hydroxamic acid derivatives of this invention are obtained via conversion of the appropriate prostanoic acid to a mixed carbonic anhydride by the usual procedure involving treatment with ethyl chloroformate in the presence of triethylamine, followed by reaction with hydroxyl amine or an N-hydroxyl primary amine. The ureido derivatives of this invention can be prepared by treatment of the prostanoic acids with the appropriate N,N'-di(lower alkyl)phenylcarbodiimide.

All of the compounds of this invention can be isolated and purified by conventional methods. Isolation can be accomplished, for example, by dilution of the reaction mixture with water, extraction with a water-immiscible solvent such as methylene chloride, ethyl acetate, benzene, cyclohexane, ether, toluene and the like, chromatography, adsorption on ion-exchange resins, distillation, or a combination of these. Purification of the compounds of this invention can be accomplished by means known in the art for the purification of prostaglandins and lipids, fatty acids, fatty esters and fatty amides. For example, reverse phase partition chromatography, countercurrent distribution, adsorption chromatography on acid washed Florisil® (synthetic magnesium silicate) and acid washed silica gel, preparative paper chromatography, preparative thin layer chromatography, chromatography over silver loaded cation exchange resins, and combinations thereof can be used effectively to purify the compounds produced by the processes of this invention.

The racemic intermediates of this invention can be resolved into their optically active components by a number of methods of resolution well known in the art. For example, compounds XXX, XXXV, XXXVIII, XLI and XLVI can all be obtained as free acids. These acids can be treated with an optically active base such as cinchonine, quinine, brucine, d- or 1-α-phenylethylamine and the like to produce diastereoisomeric salts which can be separated by crystallization. Alternatively, the acid may be esterified with an optically active alcohol, e.g., d- or 1-menthol, estradiol 3-acetate, etc., and the diastereoisomeric esters then resolved.

Resolution of the racemic prostaglandin-like compounds of this invention can also be accomplished by reverse phase and absorption chromatography on an optically active support and adsorbent and by selective transformation of one isomer with a biologically-active prostaglandin transforming system. Such transformations can be carried out by incubation or perfusion using methods well established in the art, followed by isolation and recovery of the isomer resistant to the metabolic transformation applied.

Additional procedures for effecting the resolution of the racemic products and intermediates of this invention involve conversion of a 9α-hydroxy racemate (illustrated by IL and L below) to the corresponding phthalate half acid-ester (e.g., LI) and conversion of this di-acid to a bis salt (e.g., LII) with an optically active amine (e.g., 1-(−)-α-methylbenzylamine, d-(+)-α-methylbenzylamine, brucine, dehydroabietylamine, strychnine, quinine, cinchonine, cinchonidine, quinidine, ephedrine, deoxyephedrine, amphetamine, (+)-2-amino-1-butanol, (−)-2-amino-1-butanol, and the like). The resulting diastereoisomers are than separated by fractional crystallization and the individual components are then converted by acidification and saponification to the individual optically active parent 9α-hydroxy enantiomers (IL) and (L), oxidation of which provides the corresponding individual 9-oxo-enantiomers (LIII) and (LIV).

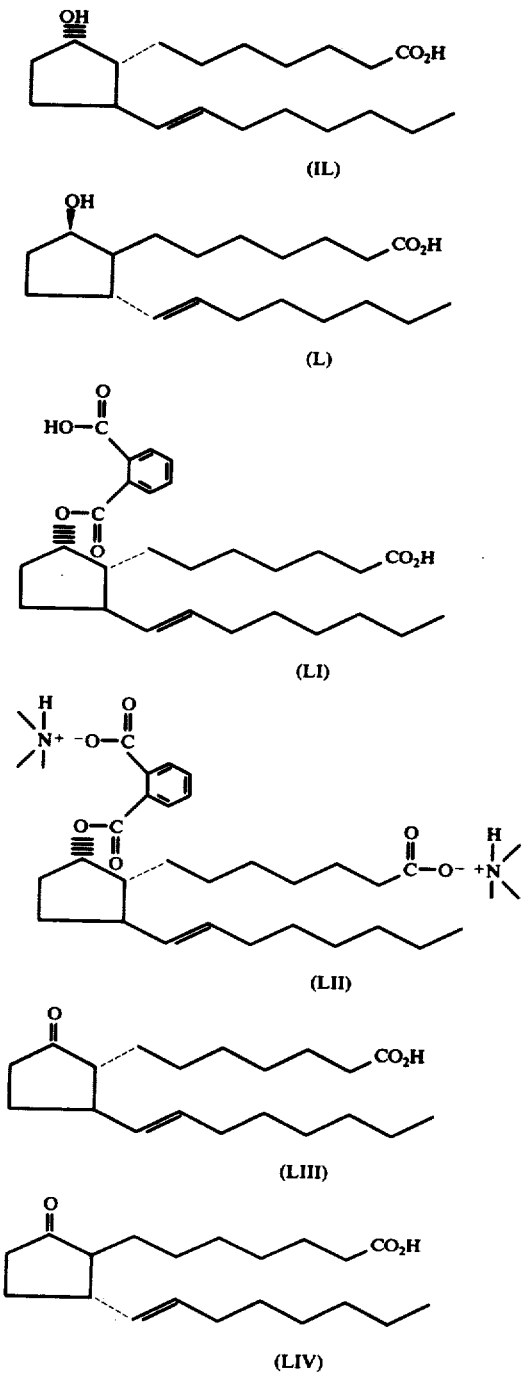

Another procedure involves conversion of the 9α-hydroxy racemate (as the prostenoic acid ester or tertiary amide) to the diastereoisomeric carbamates with an optically active isocyanate, e.g., (+)-1-phenylethylisocyanate and (−)-1-phenylethylisocyanate. Separation of the diastereoisomers, for example (LV) and (LVI), can be accomplished by fractional crystallization or by the usual chromatographic procedures, or if necessary by high speed liquid chromatography involving, if necessary, recycling techniques [see G. Fallick, *American Laboratory*, 19-27 (Aug., 1973) as well as references cited therein. Additional information concerning high speed liquid chromatography and the instruments necessary for its application is available from Waters Associates Inc., Maple St., Milford, Mass.] Base-treatement of the individual disastereoisomeric carbamates then affords the individual enantiomeric alcohols.

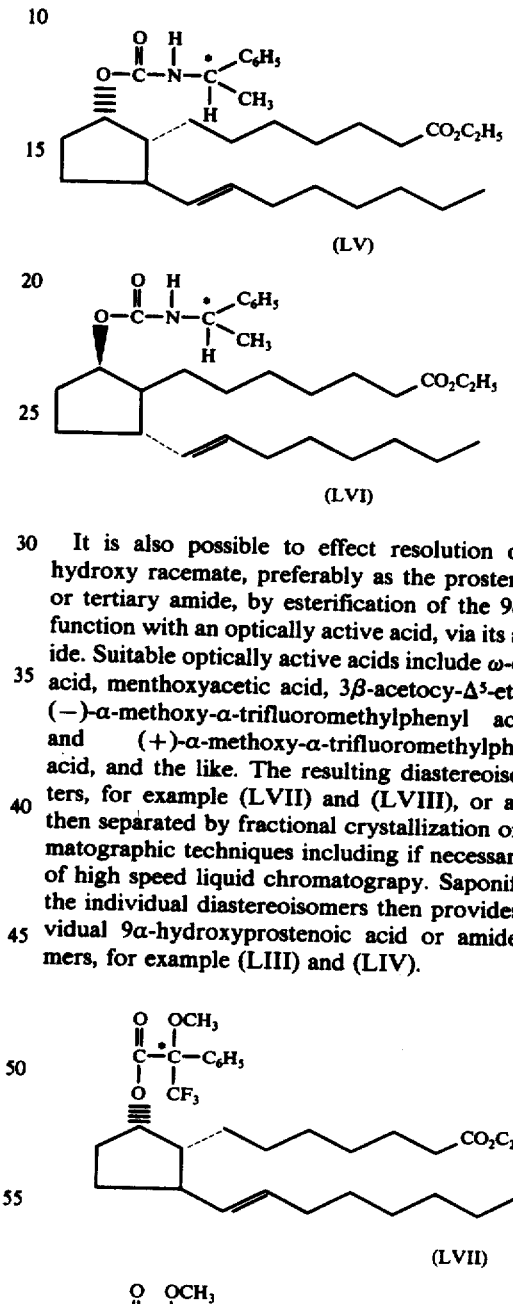

It is also possible to effect resolution of the 9α-hydroxy racemate, preferably as the prostenoate ester or tertiary amide, by esterification of the 9α-hydroxy function with an optically active acid, via its acid chloride. Suitable optically active acids include ω-camphoric acid, menthoxyacetic acid, 3β-acetocy-Δ⁵-etianic acid, (−)-α-methoxy-α-trifluoromethylphenyl acetic acid and (+)-α-methoxy-α-trifluoromethylphenylacetic acid, and the like. The resulting diastereoisomeric esters, for example (LVII) and (LVIII), or amides are then separated by fractional crystallization or by chromatographic techniques including if necessary, the use of high speed liquid chromatograpy. Saponification of the individual diastereoisomers then provides the individual 9α-hydroxyprostenoic acid or amide enantiomers, for example (LIII) and (LIV).

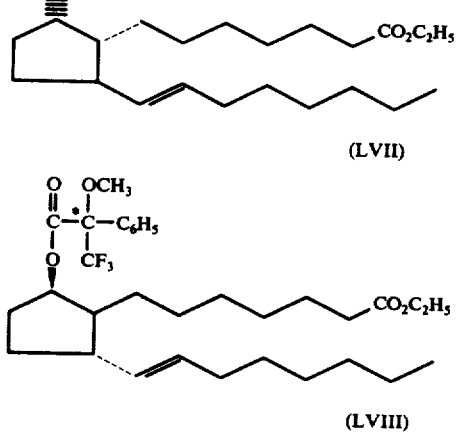

Another resolution procedure involves derivatization of the keto function of the racemic 9-oxoprostenoic acid, ester, or amide wth the usual type of ketone derivatizing agents bearing an optically active center. The resulting mixture of diastereoisomeric derivatives can then be separated by fractional crystallization or by chromatography or, if necessary, by high speed liquid chromatography. The individual diastereoisomeric keto derivatives, for example (LIX) and (LX), are then convertable to the individual 9-oxo enantiomers (LIII) and (LIV) by any of the usual cleavage techniques. Ketone reduction of the 9-oxo-enantiomer as described hereinabove then provides the corresponding 9α-hydroxy or 9β-hydroxy enantiomer. Among the optically active reagents useful for ketone derivatization are 1-α-aminoxy-γ-methylpentanoic acid hydrochloride [E. Testa et al., Helv. Chimica Acta, 47 (3), 766 (1973)], menthylhydrazine, and 4-α-methylbenzylsemicarbazide.

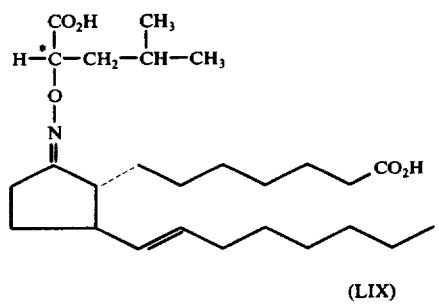

(LIX)

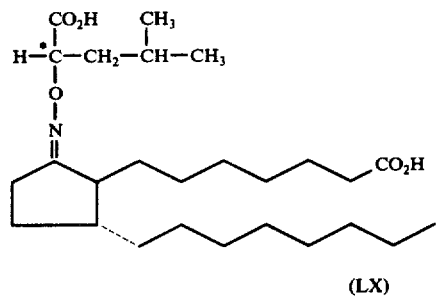

(LX)

The novel compounds of the present invention are obtainable as yellow oils having characteristic absorption spectra They are relatively soluble in common organic solvents such as ethanol, ethyl acetate, dimethylformamide, and the like.

The novel compounds of the present invention are useful as hypotensive agents and their prostaglandin-like hypotensive activity was demonstrated in the following test procedure. This procedure is a modification of the technique described by Pike et al., Prostaglandins, Nobel Symposium 2, Stockholm, June, 1966; p. 165.

Male Wistar strain rates (Royal Hart Farms) averaging approximately 250 grams in weight were fastened to rat boards in a supine position by mans of canvas vests and limb ties. The femoral area was infiltrated subcutaneously with lidocaine and the iliac artery and vein were exposed and cannulated. Arterial blood pressure (systolic/diastolic) was recorded using a Statham $P_{23}$ Db pressure transducer-Offner dynograph system. To obtain a stable blood pressure, the animals were anesthetized before use with pentobarbital, 30 mg./kg. of body weight intravenously, and also were given hexamethonium bitartrate, 2 mg./kg., of body weight intravenously. The test compounds were prepared by ultrasonic dispersion in a saline-Tween 80® vehicle. A constant intravenous dose volume of 0.5 ml. was administered and test doses ranged from 0.1 to 10.0 mg./kg. of body weight. Increasing or decreasing doses were selected depending on the dose response obtained. In Table I below are set forth the minimal doses required to produce a decrease of about 10 mm. in diastolic blood pressure for typical compounds of the present invention.

TABLE I

| Compound | Minimal Effective Dose (mg./kg. of body weight) |
|---|---|
| 9-oxo-13-trans-prostenohydroxamic acid | 2 |
| dimethyl amide of 9-oxo-13-trans-prostenoic acid | 2 |
| β-pyridyl amide of 9-oxo-13-trans-prostenoic acid | 2–8 |
| 4-phenyl-1-piperazinyl amide of 9-oxo-13-trans-prostenoic acid | 8 |
| N-(3-dimethylaminopropyl)-9-hydroxy-13-trans-prostenamide | 0.2 |
| 4-methyl-1-piperazinyl amide of 9-oxo-13-trans-prostenoic acid | 4 |
| pyrrolidine amide of 9-oxo-13-trans-prostenoic acid | 8 |
| β-hydroxyethyl amide of 9-oxo-13-trans-prostenoic acid | 0.4 |
| N-(3-dimethylaminopropyl)-9-oxo-13-trans-prostenamide | 0.4 |
| methyl amide of 9-oxo-13-trans-prostenoic acid | 4–8 |
| 9-oxo-13-trans-prostenamide | 2 |
| morpholine amide of 9-oxo-13-trans-prostenoic acid | 1 |
| dimethyl hydrazide of 9-oxo-13-trans-prostenoic acid | 2 |

This hypotensive effect is short acting and a continuous infusion of compound is necessary to maintain the effect. Nevertheless, it is authoritatively claimed that hypotension induced by prostaglandins is of an ideal nature and therefore, despite the necessity of infusion, these compounds may be useful in the treatment of certain hypertensive crisis situations such as eclampsia. A decription of this problem appears in The Medical Letter on Drugs and Therapeutics (p. 31–32, issue of April 3, 1970). Also, in a news item from *Medical World News*, 10, 12 (August 1, 1969), Dr. J. B. Lee, associate professor of medicine at St. Louis University, is quoted as saying that the related prostaglandin A compounds "might be useful in a hypertensive crisis such as eclampsia." The natural prostaglandins are only difficultly available, and at great cost. Thus, although the prostaglandin congeners and derivatives of this invention may be less potent and larger doses would probably be necessary, the greater availability of these compounds, when prepared by the methods of this invention, should provide a substantial economic advantage.

The novel compounds of the present invention are also useful as antimicrobial agents. They posses antibacterial and antifungal activity in vitro against a variety of standard laboratory microorganisms as determined by the agar-dilution streak-plate technique. In this assay, the compounds to be tested are made up to contain 2.5 mg. of test compound per milliliter of solution. Observing sterile techniques, two-fold serial dilutions are made of each test solution. One milliliter of each of the original solutions and of each of the serial dilutions is then added to 9 ml. of warm sterile nutrient agar capable of supporting growth of the bacterial test cultures. A second set of agar dilutions is prepared identical to the first except that the nutrient agar is designed to support the growth of the fungal test cultures. The standard sterile nutrient agar solutions containing the different dilutions of the test compounds, along with suitable and comparable control dilutions containing no test compound, are then allowed to cool in Petri dishes thereby forming solidified agar plates. The test bacteria and yeast-like fungi are prepared for use by growing in broth overnight. The spores of the filamentous fungi are harvested from mature agar slant cultures and are suspended in sterile physiological saline solution. A loopful of each of the resulting live suspensions is then, still employing sterile techniques, streaked upon the surfaces of each of the agar plates and the resulting streaked plates are then incubated. After an appropriate period of time, each of the streaks on each of the plates is inspected visually and the extent, if any, of bacterial or fungal growth is noted. The minimal inhibitory concentration (expressed in micrograms per milliliter) is defined as the concentration of test compound causing complete inhibition of growth of any particular organism.

In a representative operation, and merely by way of illustration, the minimal inhibitory concentration of typical compounds of the present invention against a variety of test organisms as determined in the above-described assay are set forth in Tables II and III below:

TABLE II

| Compound | Minimal inhibitory conc. (meg./ml.) | | | |
|---|---|---|---|---|
| | (1) | (2) | (3) | (4) |
| dimethyl amide of 9-oxo-13-trans-prostenoic acid | 25 | 25 | 25 | 25 |
| morpholine amide of 9-oxo-13-trans-prostenoic acid | 250 | | 250 | 250 |
| 9-oxo-13-trans-prostenamide | 50 | 50 | 50 | 25 |
| 4-methyl-1-piperazinyl amide of 9-oxo-13-trans-prostenoic acid | 25 | 25 | 25 | 10 |
| pyrrolidone amide of 9-oxo-13-trans-prostenoic acid | 100 | 10 | 50 | 50 |
| β-hydroxyethyl amide of 9-oxo-13-trans-prostenoic acid | 25 | 25 | 25 | 10 |
| N-(3-dimethylaminopropyl)-9-oxo-13-trans-prostenamide | 100 | 100 | 100 | 25 |
| 9-oxo-13-trans-prostenehydroxamic acid | 250 | 250 | 250 | 250 |
| methyl amide of 9-oxo-13-trans-prostenoic acid | 100 | 50 | 25 | 25 |
| dimethyl hydrazide of 9-oxo-13-trans-prostenoic acid | 25 | 25 | 25 | 25 |
| N-(3-dimethylaminopropyl)-9-hydroxy-13-trans-prostenamide | 250 | 125 | 125 | 125 |

(1) Microsporum canis ATCC 10214
(2) Microsporum gypseum ATCC 14683
(3) Trichophyton tensurans NIH 662
(4) Trichophyton mentagrophytes E 11

TABLE III

| Compound | Minimal inhibitory conc. (meg./ml.) | | | |
|---|---|---|---|---|
| | (5) | (6) | (7) | (8) |
| dimethyl amide of 9-oxo-13-trans-prostenoic acid | 25 | 10 | 25 | 10 |
| | | 10 | | 25 |
| N-H amide of 9-oxo-13-trans-prostenoic acid | | | | |
| morpholine amide of 9-oxo-13-trans-prostenoic acid | | 25 | | 25 |
| 9-oxo-13-trans-prostenamide | 50 | 25 | 50 | 10 |
| 4-methyl-1-piperazineyl amide of 9-oxo-13-trans-prostenoic acid | 25 | 10 | 25 | 10 |
| pyrrolidine amide of 9-oxo-13-trans-prostenoic acid | 25 | 5 | 50 | 5 |
| β-hydroxyethyl amide of 9-oxo-13-trans-prostenoic acid | 25 | 25 | 25 | 10 |
| N-(3-dimethylaminopropyl)-9-oxo-13-trans-prostenamide | 100 | 10 | 50 | 10 |
| 9-oxo-13-trans-prostenohydroxamic acid | 250 | 250 | 250 | 250 |
| β-pyridyl amide of 9-oxo-13-trans-prostenoic acid | | | | 5 |
| methyl amide of 9-oxo-13-trans-prostenoic acid | 100 | | 5 | |
| dimethyl hydrazide of 9-oxo-13-trans-prostenoic acid | 25 | 10 | 25 | 10 |
| N-(3-dimethylaminopropyl)-9-hydroxy-13-trans-prostenamide | 250 | 6 | 62 | 6 |

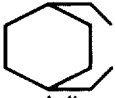

(5) Trichophyton rubrum E 97
(6) Mycobacterium smegmatis ATCC 606
(7) Stpahylococcus aureus Rose ATCC 14154
(8) Streptococcus pyogenes C 203

Topical preparations containing the novel compounds of the present invention, it is expected, will prove particularly useful. Such compositions would be designed for administration to subjects exposed to, or infected with sensitive bacteria or fungi for either treatment or prophylaxis and may include ointments, creams, emulsions, unguents, salves, emollients, sprays, washes or the like. In addition, the compounds may be used in the form of solutions, suspensions, emulsions, washes, powders, dusts, mists, soaps, sprays, aerosols, drenches, or other forms for the purpose of cleaning, disinfecting, or sterilizing surgical instruments, laboratory glassware or instruments, hospital walls or other surfaces, linens, dishes, laboratory tables, coops, cages, or the like. Likewise these compounds might be incorporated into soaps, detergents, sprays, or the like in the home, farm office or elsewhere with the purpose of preventing or minimizing infection or contamination with sensitive bacteria or fungi. Painting, spraying, immersion or other means of effecting contact may be applied.

The novel compounds of the present invention are also effective inhibitors of gastric acid secretion and of ulcer development in experimental animals, and thus are potentially valuable as agents for the control of gastric acid secretion and of gastric erosion and an anti-ulcer agents. Gastric acid secretion inhibitory action is usually measured by the "Shay rat" procedure [1,2] with some modifications as follows.

1. Shay et al., Gastroenterology, 5, 43, (1945).
2. Shay et al., Gastroenterology, 26, 906 (1954).

The rats (male, CFE strain) were starved for 48 hours (water was given ad libitum) to permit evacuation of stomach contents. On the morning of the experiment, under ether anesthesia, the abdominal region was shaved and a midline incision (1-1¼inch) was made with a scalpel. With the help of a closed curved hemostat the duodenum was picked up. Upon getting the duodenum into view fingers were used to pull the stomach through the opening, the stomach was then gently manipulated with fingers to rid the stomach of air and residual matter which were pushed through the pylorus. Two 5-inch sutures were drawn under the pyloric-duodenal juncture. A ligature, at the juncture, was formed with one of the threads. The second ligature was also formed by not tightened.

The test compound or the vehicle, usually 1 ml./100 g. body weight, were injected into the duodenum as close as possible to the first ligature. After injection the second ligature was tightened below the injection site to minimize leakage. The stomach was placed back through the opening into the abdominal cavity, the area of incision was washed with saline and the incision was closed with autoclips. (Occasionally, instead of an intraduodenal injection, animals were dosed by the oral or subcutaneous route. In the latter case, dosing was done thirty to sixty minutes before the operation).

Three hours later, the rats were decapitated and exanguinated, taking care that blood did not drain into the esophagus. The abdominal cavity was exposed by cutting with scissors and the esophagus close to the stomach was clamped off with a hemostat. The stomach was removed by cutting above the hemostat (the esophagus was cut) and between the two sutures. Extraneous tissue was removed, the stomach washed with saline and blotted on gauze. A slit was carefully made in the stomach which was held over a funnel and the contents were collected in a centrifuge tube. The stomach was further cut along the outside edge and turned inside out. Two ml. of water were used to wash the stomach contents into the respective centrifuge tube. The combined stomach contents and wash were then centifuged out for 10 minutes in the International Size 2 Centrifuge (setting at 30). The supernatant was collected, volume measured and recorded, 2 drops of phenolphthalein indicator (1% in 95% ethanol) were added and the solution was titrated with 0.02N NaOH (or with 0.04N NaOH when large volumes of stomach contents were encountered) to pH 8.4 (because of usual coloring of the stomach contents, phenolphthalein was only used to permit visual indication that the end point was near) and the amount of acid present was calculated.

Compounds inducing inhibition of gastric acid secretion of 20% or more were considered active. In a representative operation, and merely by way of illustration, the results obtained with this assay with typical compounds of the present invention are given in Table IIIA.

TABLE IIIA

INHIBITION OF GASTRIC ACID SECRETION (PYLORUS-LIGATED RAT)

| Compound | Intraduodenal dose mg./kg. body weight | Percent Inhibition |
|---|---|---|
| 9-oxo-13-trans-prosteno-hydroxamic acid | 100 | 38 |
| N-(3-dimethylamino-propyl) 9-oxo-13-trans-prostenamide | 100 | 76 |
| N-(3-dimethylamino-propyl) 9α/β-hydroxy-13-trans-prostenamide | 100 | 85 |
| N-(3-dimethylamino-propyl) 9-oxo-18,19,20-trinor-13-trans-prostenamide | 100 | 87 |
| N-dimethylamino 9-oxo-13-trans-prostenamide | 100 | 58 |
| N⁴-methylpiperazine amide of 9-oxo-13-trans-prostenoic acid | 100 | 36 |

Inhibition of basal gastric acid secretion was determined in the acute gastric fistula rat as follows. Female Sprague-Dawley rats (Charles River Laboratories) weighing 140–160 grams are fasted in individual cages for 18–24 hours. The rats are then lightly anesthetized with ether and their front teeth extracted to avoid destruction of the plastic cannula. A midline incision is then made and the stomach and duodenum exposed. A flanged polyvinyl tube is inserted into the fundic portion of the stomach and secured with a purse string suture line using 4-0 Mersilene. The rat is then dosed by injection of the compound into the duodenum (1.0 ml. per 100 grams body weight). After dosing, the abdominal wall and skin are closed using metal wound clips.

The rat is replaced in a cage containing a longitudinal slit to allow the polyvinyl tube to hang freely. An 8 ml. plastic collecting tube is attached to the flanged cannula and hangs freely below the cage. The first 30 minute sample is discarded designating this time as zero. The collecting tube is attached again and samples removed at the end of 60 and 120 minutes. The hourly samples are then transferred to a 15 ml. centrifuge tube and centrifuged for 5–10 minutes. Total and sediment volume are then recorded with the supernatant volume being used as volume of secretion. A 1 ml. or less aliquot is then removed and placed in a 50 ml. beaker containing 10 ml. of distilled water. This sample is then titrated using 0.01N NaOH to pH 7.0 using a Beckman zeromatic pH meter. Volume, titratable acidity (meq/L) and total acid output ($\mu$ eq/hour) are recorded. Percent inhibition is determined by comparison with the appropriate control. Groups of three rats were used. Results with representative compounds of this invention are given in Table IIIB below. All compounds are administered in vehicle (0.5% methocel, 0.4% Tween 80®, saline) at a constant volume of 1 ml./100 gram rat. Samples were sonicated with care to prevent overheating.

TABLE IIIB

INHIBITION OF GASTRIC ACID SECRETION (ACUTE GASTRIC FISTULA RAT)

| Compound | Dose mg./kg. Intraduodenal | % Inhibition after 120 minutes | |
|---|---|---|---|
| | | Total Acidity | Total Acid Output |
| N-(3-pyridyl)-3-oxo-13-trans-prostenamide | 10 | 30 | 54 |
| 4,4′-bis(dimethylamino)-N-{7-[trans-2-(1-octenyl)-5-oxo-cyclopentyl]-heptanoyl}carbanilide | 10 | 60 | 72 |

The compounds of this invention are also useful as antagonists of prostaglandin action and accordingly they are potentially useful as anti-inflammatory agents, and as agents for the treatment of periodontal disease and diarrhea. Testing for prostglandin antagonist ction is carried out in the following manner.

Sections of ascending colon, approximately 20 mm. long, from mature male gerbils (Meriones unguiculatus) weighing 70–80 g. were mounted in DeJalon's solution (154 mM NaCl; 5.95 mM $NaHCO_3$; 278 mM glucose, 5.64 mM KCl and .27 mM $CaCl_2$ in 20 ml. tissue baths) (L. and K. Glass Co., Lynnhurst, N.J.). The medium was continually gassed with a mixture of 95% $O_2$–5% $CO_2$ and maintained at 37° C. The tissues were suspended via silk suture threads between a glass hook at the base and a model FT .03C force displacement transducer (Grass Instrument, Quincy, Massachusetts). Contractions were recorded on a Poly-Viso® polygraph (Sanborn Co., Cambridge, Ma.).

After mounting, tissues were allowed to stabilize 15–20 minutes during which time adjustments were made to establish and maintain a 0.5 g. resting tension on the muscle. Thereafter, test cycles of 3–5 minutes were begun and consisted of a 1 minute exposure to the potential antagonist, if called for, folowed by a 1 minute exposure to the prostaglandin agonist, a 15–30 sec. washout and a recovery period of 2–2.5 minutes. Test compounds were introduced into the bath by microliter pipets and in preliminary experiments were observed to be evenly diffused throughout the bath within 2–3 sec. During the washout period, the tissue was rinsed with a measured amount equalling 8 volumes of medium. Muscle relaxation was virtually complete by the end of the washout period.

During preliminary tests it was noted that a final concentration of 200 ng./ml. of a racemic mixture of synthetic prostaglandin-$E_1$ (dl-$PGE_1$) produced maximal muscle contraction. Following stabilization, muscles were exposed 2 to 3 times to this concentration of dl-$PGE_1$ until a consistent response was recorded. Once maximal responses were established, test cycles with potential antagonists were commenced and were followed alternatively with prostaglandin-only test cycle. Occasionally the response to the prostaglandin alone did not return immediately to maximal and several exposures or washes with dl-$PGE_1$ were required. The contraction of the muscle induced by 200 mg./ml. dl-$PGE_1$ following exposure to a given concentration of the potential antagonist was always compared to the response of the tissue to that level of dl-$PGE_1$ in the immediately preceding cycle. Using a series of potential antagonist concentrations, an approximate $ID_{50}$ (concentration at which 50% inhibition was observed) was established. The compounds were also tested against a sub-maximal prostaglandin challenge (20 ng./ml. dl-$PGE_1$) in which case activity is reported in terns of a 50% inhibition of maximum response. The results with representative compounds of this invention are recorded below in Table IIIC.

EXAMPLE 1

Preparation of 2-carbalkoxy(methyl/ethyl)-2-(4-carbethoxybutyl)cyclopentan-1-one To a stirred solution of the sodium cyclopentanone carboxylate enolate in dimethoxyethane, prepared from 187 g. (1.248 moles) of 2-cyclopentanone carboxylate (mixed methyl and ethyl esters), 52.4 g. (1.248 moles) sodium hydride (57.2% in mineral oil) and 1.6 l. of dimethoxyethane, is added dropwise 309 g. (1.212 moles) of ethyl 5-iodovalerate. The reaction mixture is stirred and heated at reflux for 18 hours. The mixture is cooled and filtered. The solvent is removed from the filtrate by evaporation and the residue is poured into dilute hydrochloric acid and extracted with ether. The combined extracts are washed with water and saline, dried over magnesium sulfate and evaporated to give an oil. The oil is distilled under reduced pressure to give 274 g. of a light yellow oil, b.p. 140°-143° C. (0.17 mm).

EXAMPLE 2

Preparation of 2-(4-carboxybutyl)cyclopentan-1-one

A stirred mixture of 274 g. of 2-carbalkoxy(mixed methyl and ethyl esters)-2-(4-carbethoxybutyl)cyclopentan-1-one (Example 1), 600 ml. of 20% hydrochloric acid and 325 ml. of acetic acid is heated at reflux for 20 hours. Solution occurs in approximately one-half hour. The solution is cooled and diluted with water and extracted with ether. The combined extracts are washed with saline and dried over magnesium sulfate and evaporated. The residue is evaporated twice with toluene to give 144 g. of an oil.

TABLE IIIC

| INHIBITION OF dl-$PGE_1$-INDUCED CONTRACTION OF GERBIL COLON | | |
|---|---|---|
| | $ID_{50}$ (μg./ml.) | |
| Compound | vs. 20 ng. of $PGE_1$/ml. | vs. 200 ng. of $PGE_1$/ml. |
| 4-methylpiperazine amide of 9-oxo-13-trans-prostenoic acid maleate | 0.5 | 3 |
| pyrroliddine amide of 9-oxo-13-trans-prostenoic acid | 1 | |
| morpholine amide of 9-oxo-13-trans-prostenoic acid | 0.5 | |
| 3-azabicyclo[3,2,2]nonyl amide of 9-oxo-13-trans-prostenoic acid | 4 | |
| 9-oxo-13-trans-prostenamide | 5 | |
| N,N-dimethyl-9-oxo-13-trans-prostenamide | 2 | |
| N-(2-hydroxyethyl)-9-oxo-13-trans-prostenamide | 1 | |
| N-(dimethylamino)-9-oxo-13-trans-prostenamide | 0.5 | |
| N-dimethylaminopropyl)-9-oxo-13-trans-prostenamide | 0.5 | |
| 9-oxo-13-trans-prostenhydroxamine acid | | 12 |

The novel compounds of the present invention also possess activity as anti-inflammatory agents, fertility controlling agents, central nervous system regulatory agents, salt- and water-retention regulatory agents, fat matbolic regulatory agents, serum cholesterol-lowering agents and as abortifacients, anticonvulsants, and bronchodilators.

In accordance with accepted convention, an α-substituent at the 9-position is behind the plane whereas a β-substituent at the 9-position is in front of the plane of the paper. This is usually represented by a - - - bond for an α-substituent, a — bond for a β-substituent, and a ～ bond where both are indicated. Thus, the 9-hydroxy derivatives may be variously represented as follows:

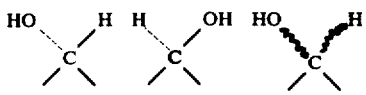

The invention will be described in greater detail in conjunction with the following specific examples.

EXAMPLE 3

Preparation of 2-(4-carbethoxybutyl)cyclopentan-1-one

A stirred solution of 124 g. (0.673 mole) of 2-(4-carboxybutyl)cyclopentan-1-one (Example 2), 800 ml. of ethanol and 1 g. of p-toluenesulfonic acid monohydrate is heated at reflux for 18 hours. The solvent is evaporated and the residue is dissolved in ether. The ether solution is washed with saline, dilute sodium bicarbonate solution and again with saline, dried over magnesium sulfate and evaporated. The oil is distilled under reduced pressure to give 149 g. of a colorless oil, b.p. 106°-109° C. (0.23 mm).

EXAMPLE 4

Preparation of 2-carbalkoxy(methyl/ethyl)-2-(3-carbethoxypropyl)cyclopentan-1-one In the manner described in Example 1, treatment of 2-cyclopentanone carboxylate (mixed methyl and ethyl esters) with sodium hydride in dimethoxyethane followed by ethyl 4-iodobutyrate gives a yellow oil, b.p. 136°–137° C. (0.16 mm).

EXAMPLE 5

Preparation of 2-(3-carboxypropyl)cyclopentan-1-one

In the manner described in Example 2, treatment of 2-carbalkoxy(mixed methyl and ethyl esters)-2-(3-carbethoxypropyl)cyclopentan-1-one (Example 4) with a 20% hydrochloric acid and acetic acid mixture gives a yellow oil.

EXAMPLE 6

Preparation of 2-(4-carbethoxypropyl)cyclopentan-1-one

In the manner described in Example 3, treatment of 2-(3-carboxypropyl)cyclopentan-1-one (Example 5) with p-toluenesulfonic acid monohydrate in ethanol gives a colorless oil, b.p. 93° C. (0.10 mm).

EXAMPLE 7

Preparation of ethyl and methyl 2-(6-carbethoxyhexyl)-1-cyclopentanon-2-carboxylate In the manner described in Example 1, ethyl and methyl 2-cyclopentanone carboxylate is reacted with ethyl 7-bromoheptanoate to furnish the subject product, b.p. 147° C. (0.09 mm).

EXAMPLE 8

Preparation of 2-(6-carboxyhexyl)cyclopentan-1-one

In the manner described in Example 2, ethyl and methyl 2-(6-carbethoxyhexyl)-1-cyclopentanone-2-carboxylate (Example 7) is hydrolyzed to furnish the subject product, b.p. 143° C. (0.05 mm).

EXAMPLE 9

Preparation of 2-(6-carbethoxyhexyl)cyclopentan-1-one

In the manner described in Example 3, 2-(6-carboxyhexyl)cyclopentan-1-one (Example 8) is esterified to furnish the subject product, b.p. 110° C. (0.03 mm).

EXAMPLE 10

Preparation of ethyl (methyl) 7-(2-carbethoxycyclohexan-1-on-2-yl)heptanoate

To a stirred suspension of 51 g. of sodium hydride (57% in mineral oil) in 675 ml. of dimethylformamide is added 200 g. of 2-cyclohexanone carboxylate (60% ethyl - 40% methyl esters) over a 1–5 hr. period with external cooling to maintain the temperature at 20°–25° C. The reaction mixture is stirred at ambient temperature for 15 minutes and heated to 50° C. over 15 minutes. To the stirred mixture is added 300 g. of ethyl 7-bromoheptanoate during a 10 minute period. The reaction mixture is stirred at 50°–60° C. for 4 hours, cooled, and poured into water. The product is obtained by ether extraction. The extract is washed successively with water and saturated sodium chloride, dried and evaporated to give a liquid which is purified by distillation, IR 1735 cm$^{-1}$ (ester carbonyls) and 1710 cm$^{-1}$ (ketone carbonyl).

EXAMPLE 11

Preparation of 7-(cyclohexan-1-on-2-yl)heptanoic acid

A stirred mixture of 380 g. of mixed methyl and ethyl esters of 7-(2-carbethoxycyclohexan-1-on-2-yl)heptanoate (Example 10), 202 ml. of concentrated sulfuric acid, 970 ml. of glacial acetic acid, and 970 ml. of water is refluxed for 22.5 hours. The cooled reaction mixture is treated with 380 g. of sodium carbonate and 2 liters of water and is extracted with ether. Acidic material is partitioned from the ether extract with 1.0M sodium carbonate. The aqueous phase is acidified with concentrated hydrochloric acid and extracted with ether. The extract is washed successively with water and saturated sodium chloride, dried, and evaporated to give an oil

EXAMPLE 12

Preparation of ethyl 7-(cyclohexan-1-on-2-yl)heptanoate

A solution of 232 g. of 7-(cyclohexan-1-on-2-yl)heptanoic acid in 2500 ml. of ethanol is refluxed for 4.5 hours with 3.8 g. of p-toluenesulfonic acid monohydrate. The solution is diluted with 200 ml. of benzene, and boiling is continued for 2 hours as 200 ml. of distillate is removed. The volume of the solution is concentrated to 500 ml. After dilution with 500 ml. of ether the solution is extracted with a solution prepared from 50 ml. of saturated sodium bicarbonate, 50 ml. of saturated sodium chloride, and 100 ml. of water. The extract is washed with saturated sodium chloride, dried, and evaporated. The product is purified by distillation to give a liquid, IR 1740 cm$^{-1}$ (ester carbonyl) and 1715 cm$^{-1}$ (ketone carbonyl).

EXAMPLE 13

Preparation of 2-carbalkoxy(methyl/ethyl)-2-(3-carbethoxypropyl)cyclohexan-1-one The subject compound is prepared in the manner described in Example 10 by treatment of 2-cyclohexanone carboxylate (mixed methyl and ethyl esters) with sodium hydride and ethyl 4-iodobutyrate.

EXAMPLE 14

Preparation of 2-(3-carbethoxypropyl)cyclohexan-1-one

This compound is prepared from 2-carbalkoxy(methyl/ethyl)-2-(3-carbethoxypropyl)cyclohexan-1-one (Example 13) by decarbalkoxylation according to the procedure described in Example 11 followed by esterification by the procedure of Example 12.

EXAMPLE 15

Preparation of 2-(5-carbethoxypentyl)cyclohexan-1-one

This compound is prepared by alkylation of 2-cyclohexanone carboxylate (mixed methyl and ethyl esters) with ethyl 6-bromohexanote according to the procedure of Example 10, followed by decarbalkoxylation according to the procedure of Example 11 and finally esterification by the procedure of Example 12.

EXAMPLE 16

Preparation of 2-(7-carbethoxyheptyl)cyclohexan-1-one

Alkylation of 2-cyclohexanone carboxylate (mixed methyl and ethyl esters) with ethyl 8-bromoctanoate in accordance with the procedure of Example 10, followed by decarbalkoxylation by the procedure of Example 11 and then esterification by the procedure of Example 12 is productive of the subject compound.

EXAMPLE 17

Preparation of 2-carbalkoxy(methyl/ethyl)-2-(carbethoxymethyl)cyclopentan-1-one

In the manner described in Example 1, treatment of cyclopentane-2-carboxylate (mixed methyl and ethyl esters) with sodium hydride in dimethoxyethane followed by ethyl bromoacetate provides a yellow oil, b.p. 130°-131° C. (7 mm).

EXAMPLE 18

Preparation of 2-(carboxymethyl)cyclopentan-1-one

In the manner described in Example 2, the 2-carbalkoxy-2-carbethoxymethylcyclopentanone of Example 17 is decarbalkoxylated to provide 2-carboxymethylcyclopentan-1-one.

EXAMPLE 19

Preparation of 2-carbethoxymethylcyclopentan-1-one

In the manner of Example 3, 2-(carboxymethyl)cyclopentan-1-one (Example 18) is esterified to provide the subject ester.

EXAMPLE 20

Preparation of 1-acetoxy-2-(6-carbethoxyhexyl)cyclopent-1-ene

A stirred solution of 100 g. of 2-(6-carbethoxyhexyl)-cyclopentan-1-one (Example 9) in 250 ml. of acetic anhydride containing 0.940 g. of p-toluenesulfonic acid monohydrate is heated to boiling under partial reflux allowing distillate at 118° C. or less (i.e., acetic acid) to escape through a Vigreaux column equipped with a condenser to collect the distillate. After 16 hours, during which period acetic anhydride is added in portions in order to keep the solvent level at at least 100 ml., the solution is cooled and poured cautiously into a stirred cold mixture of saturated sodium bicarbonate solution (400 ml.) and hexane (250 ml.). The resulting mixture is stirred for an additional 30 minutes during which period solid sodium bicarbonate is added periodically to insure a basic solution. The hexane layer is separated and washed with saturated sodium chloride solution, dried with anhydrous magnesium sulfate and taken to dryness. Distillation of the residual oil gives 102 g. (87%) of pale yellow oil, b.p. 118° C. (0.07 mm).

EXAMPLE 21

Preparation of 1-acetoxy-2-(carbethoxymethyl)cyclopent-1-ene

In the manner described in Example 20, treatment of 2-(carbethoxymethyl)cyclopentan-1-one (Example 19) with acetic anhydride and p-toluenesulfonic acid monohydrate gives an oil, b.p. 130°-131° C. (7 mm).

EXAMPLE 22

Preparation of 1-acetoxy-2-(3-carbethoxypropyl)cyclopent-1-ene

In the manner described in Example 20, treatment of 2-(3-carbethoxypropyl)cyclopentan-1-one (Example 6) with acetic anhydride and p-toluenesulfonic acid monohydrate gives a yellow oil, b.p. 98°-103° C. (0.35 mm).

EXAMPLE 23

Preparation of 1-acetoxy-2-(4-carbethoxybutyl)cyclopent-1-ene

In the manner described in Example 20, treatment of 2-(4-carbethoxybutyl)cyclopentan-1-one (Example 3) with acetic anhydride and p-toluenesulfonic acid monohydrate gives a yellow oil, b.p. 109°-110° C. (0.37 mm).

EXAMPLE 24

Preparation of ethyl 7-(1-acetoxycyclohex-1-en-2-yl)heptanoate

A stirred solution of 28.0 g. of ethyl 7-(cyclohexan-1-on-2-yl)heptanoate (Example 12), 170 mg. of p-toluenesulfonic acid monohydrate, and 25.6 g. of acetic anhydride is heated for 5 hours while allowing 8.0 g. of distillate to distill. The cooled solution is poured into a stirred, ice-cold mixture of 500 ml. of saturated sodium bicarbonate and 250 ml. of hexane. After one hour the hexane phase is separated, dried, and evaporated. The crude product is distilled to give a liquid, IR 1760 cm$^{-1}$ (vinyl ester carbonyl) and 1740 cm$^{-1}$ (ethyl ester carbonyl).

EXAMPLE 25

Preparation of 1-acetoxy-2-(3-carbethoxypropyl)cyclohex-1-ene

Treatment of 2-(3-carbethoxypropyl)cyclohexan-1-one (Example 14) with acetic anhydride by the procedure of Example 24 is productive of the subject compound.

EXAMPLE 26

Preparation of 1-acetoxy-2-(5-carbethoxypentyl)cyclohex-1-ene

Treatment of 2-(5-carbethoxypentyl)cyclohexan-1-one (Example 15) with acetic anhydride by the procedure of Example 24 is productive of the subject compound.

EXAMPLE 27

Preparation of 1-acetoxy-2-(7-carbethoxyheptyl)cyclohex-1-ene

Treatment of 2-(7-carbethoxyheptyl)cyclohexan-1-one (Example 16) with acetic anhydride by the procedure of Example 24 is productive of the subject compound.

EXAMPLE 28

Preparation of 2-(6-carbethoxyhexyl)cyclopent-2-en-1-one

To a rapidly stirred mixture of 50 g. of 1acetoxy-2-(6-carbethoxyhexyl)cyclopent-1-ene (Example 20) in 150 ml. of chloroform, 200 ml. of water and 18.8 g. of calcium carbonate, cooled in an ice bath, is added dropwise over a period of about 30 minutes, a solution of 30 g. of bromine in 50 ml. of carbon tetrachloride. After stirring for an additional 45 minutes the chloroform layer is separated and washed successively with dilute sodium thiosulfate solution, saturated sodium chloride solution, dried with anhydrous magnesium sulfate and taken to dryness under reduced pressure.

The residual oil is dissolved in 50 ml. of N,N-dimethylformamide and added to a mixture of 33 g. of lithium bromide and 32 g. of lithium carbonate in 375 ml. of N,N-dimethylformamide, previously dried by refluxing with 375 ml. of benzene under a Dean-Stark apparatus followed by distillation of the benzene. The mixture is stirred at the reflux temperature for 30 minutes, then cooled and poured into 850 ml. of ice-cold water. The resulting mixture is acidified (cautiously) with 4N hydrochloric acid and extracted with ether three times. The combined ether extracts are washed with saturated sodium chloride solution, dried with anhydrous magnesium sulfate and taken to dryness under reduced pressure to afford 41.5 g. of an amber oil. In order to convert any isomeric material to the desired product, 41.5 g. of the above material is treated with 0.500 g. of p-toluenesulfonic acid monohydrate in 450 ml. of absolute alcohol at the reflux temperature for 18 hours. The solution is taken to dryness under reduced pressure. The resulting gum is dissolved in ether and washed with saturated sodium bicarbonate solution, saturated sodium chloride solution, dried with anhydrous magnesium sulfate and taken to dryness under reduced pressure. The residual oil is distilled to give 30.2 g. of product; b.p. 118° C. (0.05 mm); $\lambda_{max}^{MeOH}$ 229 mμ (ε9950); $\lambda_{max}$ 5.75, 5.85, 6.15, 8.45 μ; vapor phase chromatography shows 99% product, containing 1% 2-(6-carbethoxyhexyl)cyclopentan-1-one.

This product can be purified by the following procedure. A mixture of 120 g. of 2-(6-carbethoxyhexyl)-2-cyclopentenone, containing approximately 5% of the saturated analogue, and 7.67 g. (10 mole percent) of p-carboxyphenylhydrazine in 400 ml. of absolute ethanol is stirred at ambient temperatures for 18 hours and is then refluxed for 1 hour. The mixture is cooled, the solvent is evaporated, and the residue is taken up into 150 ml. of chloroform and passed through a column of 450 g. of aluminum oxide (Merck). The filtrate is evaporated to yield a colorless oil containing < 0.5% of the saturated impurity.

EXAMPLE 29

Preparation of 2-(carbethoxymethyl)cyclopent-2-en-1-one

In the manner described in Example 28, treatment of 1-acetoxy-2-(carbethoxymethyl)cyclopent-1-ene (Example 21) with bromine and subsequent dehydrobromination with lithium bromide-lithium carbonate in N,N-dimethylformamide gives an amber oil. This material is subjected to chromatography on diatomaceous earth using an n-heptane:methyl cellosolve system. Removal of the solvent from hold back volume 4.5–4.7 gives an oil which is then further treated with hydroxylamine hydrochloride, sodium acetate in ethanol at room temperature for 18 hours to give the desired product; b.p. 71° C. (0.12 mm); $\lambda_{max}^{MeOH}$ 222 mμ (10,300); $\lambda_{max}$ 5.75, 5.85, 6.15, 8.65 μ.

EXAMPLE 30

Preparation of 2-(3-carbethoxypropyl)cyclopent-2-en-1-one

In the manner described in Example 28, bromination of 1-acetoxy-2-(3-carbethoxypropyl)cyclopent-1-ene (Example 22) followed by dehydrobromination with lithium bromide and lithium carbonate is productive of the subject compound.

EXAMPLE 31

Preparation of 2-(4-carbethoxybutyl)cyclopent-2-en-1-one

In the manner described in Example 28, treatment of 1-acetoxy-2-(4-carbethoxybutyl)cyclopent-1-ene (Example 23) with bromine and subsequent treatment of the brominated product with a mixture of lithium bromide and lithium carbonate in N,N-dimethylformamide is productive of the subject compound. Treatment of this product with p-carboxyphenylhydrazine by the procedure of Example 28 furnishes a product which contains less than 0.5% of the corresponding saturated ketone.

EXAMPLE 32

Preparation of 1-methoximino-2-(6-carbethoxyhexyl)-2-cyclopentene

To a mixture of 35.97 g. (0.151 mole) of 2-(6-carbethoxyhexyl)-2-cyclopentenone (Example 28) and 15.0 g. (0.180 mole) of methoxyamine hydrochloride in 300 ml. of absolute ethanol is added 25 ml. of pyridine and the resulting solution is stirred for 20 hours at ambient temperatures. The solvent is evaporated and the residue is partitioned between water and diethyl ether. The organic phase is washed with water and saturated brine, dried (Na$_2$SO$_4$), and the solvent is evaporated to yield an oil. Distillation yields 38.7 g. of a colorless oil, b.p. 115°–118° C. (0.075 mm). IR (film): 1740, 1627, 1053, 890 cm$^{-1}$. $\lambda_{max}$(MeOH) 243 (13,000). NMR δ (CDCl$_3$): 3.89.

EXAMPLE 33

Preparation of 1-methoximino-2-(7-hydroxyheptyl)-2-cyclopentene

To an ice cooled solution of 34.10 g. (0.128 mole) of 1-methoximino-2-(6-carbethoxyhexyl)-2-cyclopentene (Example 32) in 200 ml. of benzene under nitrogen is added dropwise 225 ml. of a 25% solution of diisobutyl aluminum hydride in hexane. The resulting solution is stirred for 2 hours at 0°–5° C., poured onto ice and dilute hydrochloric acid, and the aqueous phase is saturated with sodium chloride. The organic phase is separated, washed with saturated brine, dried (Na$_2$SO$_4$), and evaporated to yield an oil. The latter is dissolved in 100 ml. of hot hexane and cooled to yield 24.3 g. of crystals, m.p. 62°–64° C. IR (KBr) 3260, 1630, 1059, 893 cm$^{-1}$. $\lambda_{max}$ 243 (14,200). NMR (CDCl$_3$) δ: 2.37.

EXAMPLE 34

Preparation of 1-methoximino-2-(7-p-toluenesulfonyloxyheptyl)-2-cyclopentene

To a solution of 5.00 g. (0.0222 mole) of 1-methoximino-2-(7-hydroxyheptyl)-2-cyclopentene (Example 33) in 50 ml. of dry pyridine at 0° C. is added 8.45 g. (0.0444 mole) of p-toluenesulfonyl chloride and the resulting solution is chilled at 5° C. overnight. The mixture is partitioned between 300 ml. of ice water and diethyl ether. The organic phase is washed with 1:1 ice cold hydrochloric acid, cold water, and cold saturated brine, dried (NaSO$_4$/K$_2$CO$_3$), and evaporated under reduced pressure at room temperature to yield an oil.

The latter is dissolved in 600 ml. of hexane, treated with 0.5 g. of Darco, filtered and evaporated to yield 7.7 g. of a colorless oil. IR (film) 1600, 1192, 1182, 1053, 890 cm$^{-1}$. $\lambda_{max}$ (MeOH) 228 and 243.

EXAMPLE 35

Preparation of 1-methoximino-2-(8,8-dicarbethoxyoctyl)-2-cyclopentene

To an alcoholic solution of sodiodiethyl malonate, prepared from 0.847 g. (0.0368 g. atoms) of sodium, 100 ml. of absolute ethanol, and 7.05 g. (0.0440 mole) of diethyl malonate is added 7.7 g. of the tosylate of Example 34 and the mixture is refluxed for 2 hours under a nitrogen atmosphere. The mixture is partitioned between cold dilute hydrochloric acid and diethyl ether, and the organic phase is washed with water and saturated brine, dried ($Na_2SO_4$), and evaporated to yield an oil. The excess diethyl malonate is distilled off under reduced pressure to yield 6.45 g. of a yellowish oil. IR (film) 1755, 1728, 1625, 1054, 890 cm$^{-1}$.

EXAMPLE 36

Preparation of 1-methoximino-2-(8,8-dicarboxyoctyl)-2cyclopentene

A mixture of 6.45 g. of the diester of Example 35 and 6.72 g. of potassium hydroxide in 150 ml. of 1:1 aqueous methanol is refluxed for 1 hour, cooled, and is partitioned between water and diethyl ether. The aqueous phase is acidified with hydrochloric acid, extracted with ether, and the organic phase is washed with water and saturated brine, dried ($Na_2SO_4$) and evaporated to yield a solid. The solid is crystallized from benzene to yield 4.15 g. of tan crystals, m.p. 135°–137° C. (—$CO_2$).

EXAMPLE 37

Preparation of 1-methoximino-2-(8-carboxyoctyl)-2-cyclopentene

A solution of 3.926 g. (0.0126 mole) of the diacid of Example 36 in 20 ml. of xylene is refluxed for 1.5 hours, cooled, and evaporated to yield a tan solid. IR (KBr) 1720, 1618, 1179, 1050, 986 cm$^{-1}$.

EXAMPLE 38

Preparation of 2-(8-carboxyoctyl)cycopent-2-en-1-one

The acid methoxime from Example 37 is refluxed for 5 hours with 55 ml. of acetone and 20 ml. of 2N hydrochloric acid. The mixture is cooled, the solvent is evaporated, and the residue is partitioned between water and diethyl ether. The organic phase is washed with water and saturated brine, dried ($Na_2SO_4$) and evaporated to yield a tan solid. IR (KBr) 1745, 1665 cm$^{-1}$. $\lambda_{max}$ (MeOH) 228 (12,600).

EXAMPLE 39

Preparation of 2-(8-carbethoxyoctyl)cyclopent-2-en-1-one

The acid ketone from Example 38 is Fisher esterified with 100 ml. of absolute ethanol, 100 ml. of benzene, and 20 mg. of p-toluenesulfonic acid for 6 hours, cooled, and the solvent is evaporated. The resulting oil is dissolved in 3:1 benzene-ether and the solution is passed through a column of 100 g. of Florisil. The filtrate is evaporated and the residue is distilled to yield 2.97 g. of a colorless oil, b.p. 137°–139° C. (0.05 Torr).

EXAMPLE 40

Preparation of ethyl 7-(cyclohex-2-en-1-one-2-yl)heptanoate

To a stirred solution of ethyl 7-(1-acetoxycyclohex-1-en-2-yl)heptanoate (Example 24) in 750 ml. of acetic acid and 125 ml. of pyridine at 10° C. is added a solution of 13.8 g. of bromine in 200 ml. of acetic acid over 20 minutes. The resulting solution is allowed to stand at ambient temperature for 45 minutes and is then decolorized with sodium sulfite. The solution is poured into 800 ml. of half-saturated sodium chloride and extracted with 1:1 hexane-ether. The extract is washed successively with water and saturated sodium chloride, dried over sodium carbonate, and evaporated to give 32 g. of the crude bromoketone. To a stirred suspension of 14.2 g. of lithium bromide and 16.6 g. of lithium carbonate in 250 ml. of anhydrous dimethylformamide at 80° C. is added the above bromoketone. The stirred mixture is heated to boiling over 20 minutes and refluxed for 15 minutes. The cooled mixture is poured into 1000 ml. of water, acidified with dilute hydrochloric acid, and extracted with ether. The extract is washed successively with water and saturated sodium chloride, dried, and evaporated. The product is purified by distillation to give a liquid, IR 1740 cm$^{-1}$ (ester carbonyl), 1685 cm$^{-1}$ (ketone carbonyl), and 1650 cm$^{-1}$ (olefin); NMR ($CCl_4$) 6.63 (multiplet, vinyl proton).

EXAMPLE 41

Preparation of 2-(3-carbethoxypropyl)cyclohex-2-en-1-one

In accordance with the procedure of Example 40, bromination of 1-acetoxy-2-(3-carbethoxypropyl)cyclohex-1-ene (Example 25) followed by treatment with lithium bromide and lithium carbonate is productive of the subject compound.

EXAMPLE 42

Preparation of 2-(5-carbethoxypentyl)cyclohex-2-en-1-one

By the procedure of Example 40, bromination of 1-acetoxy-2-(5-carbethoxypentyl)cyclohex-1-ene (Example 26) followed by treatment with lithium bromide and lithium carbonate is productive of the subject compound.

EXAMPLE 43

Preparation of 2-(7-carbethoxyheptyl)cyclohex-1-en-2-one

By the procedure of Example 40, bromination of 1-acetoxy-2-(7-carbethoxyheptyl)cyclohex-1-ene (Example 27) followed by treatment with lithium bromide and lithium carbonate is productive of the subject compound.

EXAMPLE 44

Preparation of ethyl 9-oxo-13-trans-prostenoate

A solution of 1.102 g. of 1-octyne in 2 ml. of benzene is treated with 11.5 ml. of 15% diisobutylaluminum hydride in toluene and the solution is heated to 50° C. for 2 hours. The solution is cooled, its solvent is removed in vacuo, and the resulting oil is treated with 5.45 ml. of 5.10% methyl lithium in diethyl ether with ice cooling. To the resulting solution is added 1.830 g. of 2-(6-carbethoxyhexyl)-2-cyclopentenone (Example 28) and the solution is stirred at ambient temperatures for 18 hours. The solution is poured onto ice and dilute hydrochloric acid, and the mixture is extracted with diethyl ether. The organic phase is washed with dilute sodium bicarbonate, water, and saturated brine, dried, and evaporated. The residue is purified by chromatography on Florisil and distillation to yield 1.878 g. of an oil, IR 1736 cm$^{-1}$ (ester and ketone carbonyls) 969 cm$^{-1}$ (trans vinyl group); NMR (CDCl$_3$)δ5.14–5.87 (multiplet, 2H, vinyl protone, J trans=15 Hz); Mass Spectrum, parent peak at 350 mu.

EXAMPLE 45

Preparation of ethyl 20-butyl-9-oxo-13-trans-prostenoate

In the manner described in Example 44, 2-(6-carbethoxyhexyl)-2-cyclopentenone (Example 28) is added to the reagent prepared from 1-dodecyne, diisobutylaluminum hydride, and methyl lithium. The crude produce product by acid hydrolysis and ether extraction is purified by silica gel chromatography to give an oil, IR 1740 cm$^{-1}$ (ester and ketone carbonyls) 967 cm$^{-1}$ (trans vinyl group).

EXAMPLE 46

Preparation of ethyl 9-oxo-18,19,20-trinor-13-trans-prostenoate

In the manner described in Example 44, 2-(6-carbethoxyhexyl)-2-cyclopentenone (Example 28) is added to the reagent prepared from 1-pentyne, diisobutylaluminum hydride, and methyl lithium. The crude product obtained by acid hydrolysis and ether extraction is purified by distillation to give a liquid, IR 1740 cm$^{-1}$ (ester and ketone carbonyls) 967 cm$^{-1}$ (trans vinyl group).

EXAMPLE 47

Preparation of ethyl 15-methyl-9-oxo-17,18,19,20-tetranor-13-trans-prostenoate

In the manner described in Example 44, 2-(6-carbethoxyhexyl)-2-cyclopentenone (Example 28) is added to the reagent prepared from 3-methyl-1-butyne, diisobutylaluminum hydride, and methyl lithium. The crude product obtained by acid hydrolysis and ether extraction is purified by distillation to give a liquid, IR 1740 cm$^{-1}$ (ester and ketone carbonyls) 967 cm$^{-1}$ (trans vinyl group).

EXAMPLE 48

Preparation of ethyl 20-chloro-9-oxo-13-trans-prostenoate

In the manner described in Example 44, 2-(6-carbethoxyhexyl)-2-cyclopentenone (Example 28) is added to the reagent prepared from 8-chloro-1-octyne [W. J. Gensler and G. R. Thomas, *J. Amer. Chem. Soc.*, 73, 4601 (1951)], diisobutylaluminum hydride, and methyl lithium. The crude product obtained by acid hydrolysis is purified by silica gel chromatography to give an oil, IR 1740 cm$^{-1}$ (ester and ketone carbonyls), 967 cm$^{-1}$ (trans vinyl group).

EXAMPLE 49

Preparation of ethyl 9-oxo-20-nor-13-trans-prostenoate

A solution of 5.30 g. of 1-heptyne in 10 ml. of benzene is treated with 40 ml. of 1.2N diisobutylaluminum hydride in hexane and heated at 50° C. for 2 hours. The solution is cooled in an ice bath and diluted with 25 ml. of ether. To the solution is added 30 ml. of 1.6M n-butyl lithium in hexane. After stirring for 20 minutes at 15–25° C. the resulting solution is treated with a solution of 2-(6-carbethoxyhexyl)-2-cyclopentenone (Example 28). The mixture is stirred at 5–25° C. for 18–20 hours and the product then is hydrolyzed with a mixture of ice and hydrochloric acid. The crude product, obtained from the organic phase, is purified by chromatography on silica gel to give an oil, IR 1740 cm$^{-1}$ (ester and ketone carbonyls) and 967 cm$^{-1}$ (trans vinyl group).

EXAMPLE 50

Preparation of ethyl 20-methyl-9-oxo-13-trans-prostenoate

In the manner described in Example 49, 2-(6-carbethoxyhexyl)-2-cyclopentenone (Example 28) is added to the reagent prepared from 1-nonyne, diisobutylaluminum hydride and n-butyl lithium. The crude product obtained by acid hydrolysis and evaporation of organic solvent is purified by chromatography on silica gel to give an oil, IR 1740 cm$^{-1}$ (ester and ketone carbonyls) and 967 cm$^{-1}$ (trans vinyl group).

EXAMPLE 51

Preparation of ethyl 17-methyl-9-oxo-19,20-dinor-13-trans-prostenoate

In the manner described in Example 49, 2-(6-carbethoxyhexyl)-2-cyclopentenone (Example 28) is added to the reagent prepared from 5-methyl-1-hexyne, diisobutylaluminum hydride and n-butyl lithium. The crude product obtained by acid hydrolysis and evaporation of the organic solvent is purified by chromatography on silica gel to give an oil, IR 1740 cm$^{-1}$ (ester and ketone carbonyls) and 967 cm$^{-1}$ (trans vinyl group).

EXAMPLE 52

Preparation of ethyl 20-chloro-9-oxo-17,18,19-trinor-13-trans-prostenoate

In the manner described in Example 49, 2-(6-carbethoxyhexyl)-2-cyclopentenone (Example 28) is added to the reagent prepared from 5-chloro-1-pentyne, diisobutylaluminum hydride, and n-butyl lithium. The crude product, obtained by acid hydrolysis and evaporation of the organic solvent, is purified by distillation to give an oil, IR 1740 cm$^{-1}$ (ester and ketone carbonyls) and 967 cm$^{-1}$ (trans vinyl group).

EXAMPLE 53

Preparation of ethyl 9-oxo-13-propyl-18,19,20-trinor-13-trans-prostenoate

In the manner described in Example 49, 2-(6-carbethoxyhexyl)-2-cyclopentenone (Example 28) is added to the reagent prepared from 4-octyne, diisobutylaluminum hydride, and n-butyl lithium. The crude product mixture, obtained by acid hydrolysis and evaporation of the organic solvent, is separated by chromatography on silica gel and distillation to give ethyl 9-oxo-13-propyl-18,19,20-trinor-13-trans-prostenoate as an oil, IR 1740 cm$^{-1}$ (ester and ketone carbonyls); NMR (CCl$_4$) δ 5.2 ppm (multiplet, vinyl proton) and a second oil (ethyl 9-oxo-17,18,19,20-tetranorprostanoate), IR 1740 cm$^{-1}$ (ester and ketone carbonyls); NMR (CCl$_4$) δ 1.0 ppm (multiplet, terminal methyl group).

EXAMPLE 54

Preparation of cis-5-octen-1-yne

A 57% sodium hydride dispersion (9.66 g. 0.23 mole) is washed free of mineral oil in a nitrogen atmosphere with hexane. The hydride is heated at 75° C. with 220 ml. of dimethylsulfoxide for 45 minutes. The resulting green solution is cooled to 18° C. and treated with a solution of 4-pentynyl-triphenylphosphonium iodide (100 g., 0.22 mole). in 220 ml. of dimethylsulfoxide over a 25 minute period. The resulting red solution is stirred at ambient temperature for 45 minutes. To the solution is added a solution of freshly distilled propionaldehyde (14.0 g.., 0.24 mole) in 10 ml. of dimethylsulfoxide over a 10 minute period at 25° C. After standing at room temperature, the reaction is quenched with half-saturated brine and brought to pH with 4N HCl. The product is extracted with an ether-hexane mixture, and the extract is washed successively with water and brine, dried over $MgSO_4$, and concentrated. The crude product is fractionated with a spinning band column to give a colorless distillate, b.p. 121°-122° C., IR 3270, 2110 and 1645 $cm^{-1}$.

EXAMPLE 55

Preparation of ethyl 9-oxo-13-trans-17-cis-prostadienoate

In the manner described in Example 49, 2-(6-carbethoxyhexyl)-2-cyclopentenone (Example 28) is added to the reagent prepared from cis-5-octen-1-yne (Example 54), diisobutylaluminum hydride, and n-butyl lithium. The crude product, obtained by acid hydrolysis and evaporation of the organic solvent, is purified by distillation to give an oil, IR 1740 $cm^{-1}$ (ester and ketone carbonyls) and 967 $cm^{-1}$ (trans-vinyl group).

EXAMPLE 56

Preparation of ethyl 9-oxo-6,7-dinor-13-trans-prostenoate

In the manner described in Example 44, 2-(4-carbethoxybutyl)-2-cyclopentenone (Example 31) is added to the reagent prepared from 1-octyne, diisobutylaluminum hydride, and methyl lithium. The product is obtained by acid hydrolysis, ether extraction and distillation to yield a colorless oil, b.p. 149°-150° C. (0.075 mm.). IR 1740 $cm^{-1}$ (ester and ketone carbonyls) 963 $cm^{-1}$ (trans-vinyl group).

EXAMPLE 57

Preparation of ethyl 20-chloro-9-oxo-6,7-dinor-13-trans prostenoate

In the manner described in Example 49, 2-(4-carbethoxybutyl)-2-cyclopentenone (Example 31) is added to the reagent prepared from 8-chloro-1-octyne, diisobutylaluminum hydride, and n-butyl lithium. The crude product obtained by acid hydrolysis and ether extraction is purified by silica gel chromatography to give an oil, IR 1740 $cm^{-1}$ (ester and ketone carbonyls) 967 $cm^{-1}$ (trans-vinyl group).

EXAMPLE 58

Preparation of ethyl 9-oxo-6,7,20-trinor-13-trans-prostenoate

In the manner described in Example 44, 2-(6-carbethoxybutyl)-3-cyclopentenone (Example 31) is added to the reagent prepared from 1-heptyne, diisobutylaluminum hydride and methyl lithium. The crude product obtained by acid hydrolysis and ether extraction is purified by silica gel chromatography to give an oil, IR 1740 $cm^{-1}$ (ester and ketone carbonyls) 967 $cm^{-1}$ (trans-vinyl group).

EXAMPLE 59

Preparation of ethyl 9-oxo-6,7-dinor-13-trans-17-cis-prostadienoate

In the manner described in Example 55, 2-(4-carbethoxybutyl)-2-cyclopentenone (Example 31) is added to the reagent prepared from cis-5-octen-1-yne (Example 54), diisobutylaluminum hydride, and n-butyl lithium. The crude product obtained by acid hydrolysis and ether extraction is purified by silica gel chromatography to give an oil, IR 1740 $cm^{-1}$ (ester and ketone carbonyls) 967 $cm^{-1}$ (trans-vinyl group).

EXAMPLE 60

Preparation of ethyl 20-chloro-9-oxo-6,7,17,18,19-pentanor-13-trans-prostenoate In the manner described in Example 49, 2-(4-carbethoxybutyl)-2-cyclopentenone (Example 31) is added to the reagent prepared from 5-chloro-1-pentyne, diisobutylaluminum hydride, and n-butyl lithium. The crude product obtained by acid hydrolysis and ether extraction is purified by silica gel chromatography to give an oil, IR 1740 $cm^{-1}$ (ester and ketone carbonyls), 967 $cm^{-1}$ (trans-vinyl group).

EXAMPLE 61

Preparation of ethyl 17-methyl-9-oxo-6,7,19,20-tetranor-13-trans-prostenoate In the manner described in Example 49, 2-(4-carbethoxybutyl)-2-cyclopentenone (Example 31) is added to the reagent prepared from 5-methyl-1-hexyne, diisobutylaluminum hydride and n-butyl lithium. The crude product obtained by acid hydrolysis and ether extraction is purified by silica gel chromatography to give an oil, IR 1740 $cm^{-1}$ (ester and ketone carbonyls), 967 $cm^{-1}$ (trans-vinyl group).

EXAMPLE 62

Preparation of ethyl 9-oxo-13-propyl-6,7,18,19,20-pentanor-13-trans-prostenoate In the manner described in Example 44, 2(4-carbethoxybutyl)-2-cyclopentenone (Example 31) is added to the reagent prepared from 4-octyne, diisobutylaluminum hydride, and methyl lithium. The crude product obtained by acid hydroylsis and ether extraction is purified by silica gel chromatography to give an oil, IR 1740 $cm^{-1}$ (ester and ketone carbonyls).

EXAMPLE 63

Preparation of ethyl 9-oxo-3,4,5,6,7-pentanor-13-trans-prostenoate

In the manner described in Example 44, 2 -(carbethoxymethyl)-2-cyclopentenone (Example 29) is added to the reagent prepared from 1-octyne, diisobutylaluminum hydride and methyl lithium. The crude product obtained by acid hydrolysis and ether extraction is purified by silica gel chromatography to give an oil, IR 1740 cm¹ (ester and ketone carbonyls), 967 cm⁻¹ (trans-vinyl group).

EXAMPLE 64

Preparation of ethyl 9-oxo-3,4,5,6,7-pentanor-13-trans-17-cis-prostadienoate

In the manner described in Example 55, 2-(carbethoxymethyl)-2-cyclopentenone (Example 29) is added to the reagent prepared from cis-5-octen-1-yne (Example 54), diisobutylaluminum hydride, and n-butyl lithium. The crude product obtained by acid hydrolysis and ether extraction is purified by silica gel chromatograpy to give an oil, IR 1740 cm¹ (ester and ketone carbonyls), 967 cm⁻¹ (trans-vinyl group).

EXAMPLE 65

Preparation of ethyl 20chloro-9-oxo-3,4,5,6,7,17,18,19-octanor-13-trans-prostenoate In the manner described in Example 49, 2-(carbethoxymethyl)-2-cyclopentenone (Example 29) is added to the reagent prepared from 5-chloro-1-pentyne, diisobutylaluminum hydride, and n-butyl lithium. The crude product obtained by acid hydrolysis and ether extraction is purified by silica gel chromatography to give an oil, IR 1740 cm⁻¹ (ester and ketone carbonyls), 967 cm⁻¹ (trans-vinyl group).

EXAMPLE 66

Preparation of ethyl 9-oxo-5,6,7-trinor-13-trans-prostenoate

In the manner described in Example 44, 2-(3-carbethoxypropyl)-2-cyclopentenone (Example 30) is added to the reagent prepared from 1-octyne, diisobutylaluminum hydride and methyl lithium. The crude product obtained by acid hydrolysis and ether extraction is purified by silica gel chromatography to give an oil, IR 1740 cm⁻¹ (ester and ketone carbonyls), 967 cm⁻¹ (trans-vinyl group).

EXAMPLE 67

Preparation of ethyl 9-oxo-20-propyl-5,6,7-trinor-13-trans-prostenoate

In the manner described in Example 44, 2-(3-carbethoxypropyl)-2-cyclopentenone (Example 30) is added to the reagent prepared from 1-undecyne, diisobutylaluminum hydride and methyl lithium. The crude product obtained by acid hydrolysis and ether extraction is purified by silica gel chromatography to give an oil, IR 1740 cm⁻¹ (ester and ketone carbonyls), 967 cm⁻¹ (trans-vinyl group).

EXAMPLE 68

Preparation of ethyl 9-oxo-5,6,7,18,19,20-hexanor-13-trans-prostenoate

In the manner described in Example 44, 2-(3-carbethoxypropyl)-2-cyclopentenone (Example 30) is added to the reagent prepared from 1-pentyne, diisobutylaluminum hydride and methyl lithium. The crude product obtained by acid hydrolysis and ether extraction is purified by silica gel chromatography to give an oil, IR 1740 cm⁻¹ (ester and ketone carbonyls) 967 cm⁻¹ (trans-vinyl group).

EXAMPLE 69

Preparation of ethyl 20-chloro-9-oxo-5,6,7-trinor-13-transprostenate

In the manner described in Example 44, 2-(3-carbethoxypropyl)-2-cyclopentenone (Example 30) is added to the reagent prepared from 8-chloro-1-octyne, diisobutylaluminum hydride, and methyl lithium. The crude product obtained by acid hydrolysis and ether extraction is purified by silica gel chromatography to give an oil, IR 1740 cm⁻¹ (ester and ketone carbonyls), 967 cm⁻¹ (trans-vinyl group).

EXAMPLE 70

Preparation of ethyl 9-oxo-7a,7b-bis-homo-13-trans-prostenoate

In the maner described in Example 44, 2-(8-carbethoxyoctyl)-2-cyclopentenone (Example 39) is added to the reagent prepared from 1-octyne, diisobutylaluminum hydride, and methyl lithium. The crude product obtained by acid hydrolysis and ether extraction is purified by silica gel chromatography to give an oil, IR 1740 cm⁻¹ (ester and ketone carbonyls), 967 cm⁻¹ (trans-vinyl group).

EXAMPLE 71

Preparation of ethyl 20-chloro-9-oxo-7a,7b-bis-homo-17,18,19-trinor-13-trans-prostenoate In the manner described in Example 49, 2-(8carbethoxyoctyl)-2-cyclopentenone (Example 39) is added to the reagent prepared from 5-chloro-1-pentyne, diisobutylaluminum hydride, and n-butyl lithium. The crude product obained by acid hydrolysis and ether extraction is purified by silica gel chromatography to give an oil, IR 1740 cm⁻¹ (ester and ketone carbonyls), 967 cm⁻¹ (trans-vinyl group).

EXAMPLE 72

Preparation of ethyl 20-butyl-9-oxo-7a,7b-bis-homo-13-transprostenoate

In the manner described in Example 44, 2-(8carbethoxyoctyl)-2-cyclopentenone (Example 39) is added to the reagent prepared from 1-dodecyne, diisobutylaluminum hydride, and methyl lithium. The crude product obtained by acid hydrolysis and ether extraction is purified by silica gel chromatography to give an oil, IR 1740 cm⁻¹ (ester and ketone carbonyls), 967 cm⁻¹ (trans-vinyl group),

EXAMPLE 73

Preparation of ethyl 15-methyl-9-oxo-7a,7b-bis-homo-17,18,19,20-tetranor-13-trans-prostenoate In the manner described in Example 44, 2-(8-carbethoxyoctyl)-2-cyclopentenone (Example 39) is added to the reagent prepared from 3-methyl-1-butyne, diisobutylaluminum hydride, and methyl lithium. The crude product obtained by acid hydrolysis and ether extraction is purified by silica gel chromatography to give an oil, IR 1740 cm⁻¹ (ester and ketone carbonyls), 967 cm⁻¹ (trans-vinyl group).

EXAMPLE 74

Preparation of ethyl 9-oxo-10a-homo-13-trans-prostenoate

In the manner described in Example 49, 2-(6-carbethoxyhexyl)-2-cyclohexenone (Example 40) is added to the reagent prepared from 1-octyne, diisobutylaluminum hydride and n-butyl lithium. The crude product, obtained by acid hydrolysis and evaporation of the organic solvent, is purified by chromatography on silica gel and distillation to give an oil, IR 1740 cm$^{-1}$ (ester carbonyl), 1750 cm$^{-1}$ (ketone carbonyl), and 967 cm$^{-1}$ (transvinyl group).

EXAMPLE 75

Preparation of ethyl 20-butyl-9-oxo-10a-homo-13-trans-prostenoate

In the manner described in Example 49, 2-(6-carbethoxyhexyl)-2-cyclohexenone (Example 40) is added to the reagent prepared from 1-dodecyne, diisobutylaluminum hydride, and n-butyl lithium. The crude product, obtained by acid hydrolysis and evaporation of organic solvent, is purified by chromatography on silica gel and distillation to give an oil, IR 1740 cm$^{-1}$ (ester carbonyl), 1750 cm$^{-1}$ (ketone carbonyl), and 967 cm$^{-1}$ (trans-vinyl group).

EXAMPLE 76

Preparation of ethyl 20-chloro-9-oxo-10a-homo-13-trans-prostenoate

In the manner described in Example 49, 2-(6-carbethoxyhexyl)-2-cyclohexenone (Example 40) is added to the reagent prepared from 8-chloro-1-octyne, diisobutylaluminum hydride, and n-butyl lithium. The crude product, obtained by acid hydrolysis and evaporation of the organic solvent, is purified by chromatography on silica gel and distillation to give an oil, IR 1740 cm$^{-1}$ (ester carbonyl), 1750 cm$^{-1}$ (ketone carbonyl), and 967 cm$^{-1}$ (trans-vinyl group).

EXAMPLE 77

Preparation of ethyl 20-chloro-9-oxo-17,18,19-trinor-10a-homo-13-trans-prostenoate In the manner described in Example 49, 2-(6-carbethoxyhexyl)-2-cyclohexenone (Example 40) is added to the reagent prepared from 5-chloro-1-pentyne, diisobutylaluminum hydride, and n-butyl lithium. The crude product, obtained by acid hydrolysis and evaporation of the organic solvent, is purified by chromatography on silica gel and distillation to give an oil, IR 1740 cm$^{-1}$ (ester carbonyl), 1750 cm$^{-1}$ (ketone carbonyl), and 967 cm$^{-1}$ (trans-vinyl group).

EXAMPLE 78

Preparation of ethyl 9-oxo-18,19,20-trinor-10-a-homo-13-trans-prostenoate

In the manner described in Example 49, 2-(6-carbethoxyhexyl)-2-cyclohexenone (Example 40) is added to the reagent prepared from 1pentyne, diisobutylaluminum hydride, and n-butyl lithium. The crude product, obtained by acid hydrolysis and evaporation of the organic solvent, is purified by chromatography on silica gel and distillation to give an oil, IR 1740 cm$^{-1}$ (ester carbonyl), 1750 cm$^{-1}$ (ketone carbonyl), and 967 cm$^{-1}$ (trans-vinyl group).

EXAMPLE 79

Preparation of ethyl 9-oxo-10-a-homo-13-trans-17-cis-prostadienoate

In the manner described in Example 49, 2-(6-carbethoxyhexyl)-2-cyclohexenone (Example 40) is added to the reagent prepared from cis-5-octen-1-yne (Example 54), diisobutylaluminum hydride, and n-butyl lithium. The crude product, obtained by acid hydrolysis and evaporation of the organic solvent, is purified by chromatography on silica gel and distillation to give an oil, IR 1740 cm$^{-1}$ (ester carbonyl), 1750 cm$^{-1}$ (ketone carbonyl), and 967 cm$^{-1}$ (trans-vinyl group).

EXAMPLE 80-92

The 10a-homo-prostenoate derivatives of Table VI below are obtained in the manner described in Example 49 by addition of the indicated 2-(ω-carbethoxyalkyl)-2-cyclohexenone to the reagent prepared from the appropriate 1-alkyne (listed in the Table), diisobutylaluminum hydride, and n-butyl lithium. The crude products, obtained as oils by acid hydrolysis and evaporation of the organic solvent, are purified by chromatpgraphy on silica gel and distillation, IR 1740 cm$^{-1}$ (ester carbonyl), 1750 cm$^{-1}$ (ketone carbonyl), and 967 cm$^{-1}$ (trans-vinyl group).

TABLE IV

| Example | Cyclohexenone | 1-Alkyne | Product |
| --- | --- | --- | --- |
| 80 | 2-(3-carbethoxypropyl)-2-cyclohexenone (Example 41) | 1-octyne | ethyl 9-oxo-5,6,7-trinor-10a-homo-13-trans-prostenoate |
| 81 | 2-(3-carbethoxypropyl)-2-cyclohexenone (Example 41) | 1-heptyne | ethyl 9-oxo-5,6,7-20-tetranor-10a-homo-13-trans-prostenoate |
| 82 | 2-(3-carbethoxypropyl)-2-cyclohexenone (Example 41) | 5-chloro-1-pentyne | ethyl 20-chloro-9-oxo-10a-homo-5,6-7,17,18,19-hexanor-13-trans-prostenoate |
| 83 | 2-(3-carbethoxypropyl)-2-cyclohexenone (Example 41) | 3-methyl-1-butyne | ethyl 15-methyl-9-oxo-5,6,7,17,18,-19,20-heptanor-10a-homo-13-trans-prostenoate |
| 84 | 2-(5-carbethoxypentyl)-2-cyclohexenone (Example 42) | 1-octyne | ethyl 9-oxo-7-non-10a-homo-13-trans-prostenoate |
| 85 | 2-(5-carbethoxypentyl)-2-cyclohexenone (Example 42) | 1-undecyne | ethyl 9-oxo-20-propyl-7-nor-10a-homo-13-trans-prostenoate |
| 86 | 2-(5-carbethoxypentyl)-2-cyclohexenone (Example 42) | 5-methyl-1-hexyne | ethyl 17-methyl-9-oxo-7,19,20-trinor-10a-homo-13-trans-prostenoate |
| 87 | 2-(5-carbethoxypentyl)-2-cyclohexenone (Example 42) | 8-chloro-1-octyne | ethyl 20-chloro-9-oxo-10a-homo-7-nor-13-trans-prostenoate |
| 88 | 2-(7-carbethoxyheptyl)-2-cyclohexenone (Example 43) | 1-octyne | ethyl 9-oxo-7a,10a-bis-homo-13-trans-prostenoate |
| 89 | 2-(7-carbethoxyheptyl)-2-cyclohexenone (Example 43) | 1-hexyne | ethyl-9-oxo-19,20-dinor-7a,10a-bis-homo-13-trans-prostenoate |
| 90 | 2-(7-carbethoxyheptyl)-2-cyclohexenone (Example 43) | 5-chloro-1-pentyne | ethyl 20-chloro-9-oxo-7a,10a-bis-homo-17,18,19-trinor-13-trans-prestenoate |
| 91 | 2-(7-carbethoxyheptyl)-2-cyclohexenone (Example 43) | 8-chloro-1-octyne | ethyl 20-chloro-9-oxo-7a,10a-bis-homo-13-trans-prostenoate |
| 92 | 2-(7-carbethoxyheptyl)-2-cyclohexenone (Example 43) | 4-octyne | ethyl 13-propyl-9-oxo-18,19,20-trinor-7a,10a-bis-homo-13-trans-prostenoate |

EXAMPLE 93

Preparation of ethyl 9-oxo-5,6,7-trinor-10a-homo-13-trans-17-cis-prostadienoate In the manner described in Example 49, 2-(3-carbethoxypropyl)-2-cyclohexenone (Example 41) is added to the reagent prepared from cis-5-octen-1-yne (Example 54), diisobutylaluminium hydride, and n-butyl lithium.. The crude product, obtained by acid hydrolysis and evaporation of the organic solvent, is purified by chromatography on silica gel and distillation to give an oil, IR 1740 cm$^{-1}$ (ester carbonyl), 1750 cm$^{-1}$ (ketone carbonyl), and 967 cm$^{-1}$ (trans vinyl group).

EXAMPLE 94

Preparation of ethyl 9-oxo-7a,10a-bis-homo-13-trans-17-cis-prostadienoate

In the manner described in Example 49, 2-(7carbethoxyheptyl)-2-cyclohexenone (Example 43) is added to the reagent prepared from cis-5-octen-1-yne (Example 54), diisobutylaluminum hydride, and n-butyl lithium. The crude product, obtained by acid hydrolysis and evaporation of the organic solvent, is purified by chromatography on silica gel and distillation to give an oil, IR 1740 cm$^{-1}$ (ester carbonyl), 1750 cm$^{-1}$ (ketone carbonyl), and 967 cm$^{-1}$ (trans vinyl group).

EXAMPLE 95

Preparation of ethyl 20-iodo-9-oxo-17,18,19-trinor-13-trans-prostenoate

A stirred mixture of 51.5 g. of ethyl 20-chloro-9-oxo-17,18,19-trinor-13-trans-prostenoate (Example 52), 30 g. of sodium iodide, and 250 ml. of acetone is refluxed for 10 hours. An additinal 10 g. of sodium iodide is added, and the reaction is continued for 2 hours. The reaction mixture is filtered, concentrated to a volume of 150 ml., diluted with water, and extracted with ether. The extract is washed with saturated sodium chloride, dried, and evaporated to give an oil.

EXAMPLE 96

Preparation of ethyl 20-iodo-9-oxo-13-trans-prostenoate

A stirred mixture of 30 g. of ethyl 20-chloro-9-oxo-13-trans-prostenoate (Example 48), 25 g. of sodium iodide and 225 ml. of acetone is refluxed for 12 hours. The reaction mixture is concentrated, diluted with water, and extracted with ether. The extract is washed with saturated sodium chloride, dried, and evaporated to give an oil.

EXAMPLES 97–107

Treatment of the corresponding 20-chloroprostenoate or 20-chloro-17,18,19-trinor-prostenoate with sodium iodide in acetone by the procedure of Example 95 provides the 20iodo derivatives of Table V below.

TABLE V

| Example | Starting 20-Chloro Derivative of Example | Product |
|---|---|---|
| 97 | 57 | ethyl 20-iodo-9-oxo-6,7-dinor-13-trans-prostenoate |
| 98 | 60 | ethyl 20-iodo-9-oxo-6,7,17,18,19-pentanor-13-trans-prostenoate |
| 99 | 65 | ethyl 20-iodo-9-oxo-3,4,5,6,7,17,-18,19-octanor-13-trans-prostenoate |
| 100 | 69 | ethyl 20-iodo-9-oxo-5,6,7-trinor-13-trans-prostenoate |
| 101 | 71 | ethyl 20-iodo-9-oxo-7a,7b-dihomo-17,18,19-trinor-13-trans-prostenoate |
| 102 | 76 | ethyl 20-iodo-9-oxo-10a-homo-13-trans-prostenoate |
| 103 | 77 | ethyl 20-iodo-9-oxo-10a-homo-17,-18,19-trinor-13-trans-prostenoate |
| 104 | 82 | ethyl 20-iodo-9-oxo-10a-homo-5,6-7,17,18,19-hexanor-13-trans-prostenoate |
| 105 | 87 | ethyl 20-iodo-9-oxo-10a-homo-7-nor-13-trans-prostenoate |
| 106 | 90 | ethyl 20-iodo-9-oxo-7a,10a-dihomo-17,18,19-trinor-13-trans-prostenoate |
| 107 | 91 | ethyl 20-iodo-9-oxo-7a,10a-dihomo-13-trans-prostenoate |

EXAMPLE 108

Preparation of ethyl 9-oxo-18-thia-13-trans-prostenoate

To 6.0 ml. of a stirred, ice-cold solution of 0.5M 5-ethylisothiouronium iodide in 10:1 ethanol:water is added 264 mg. of sodium hydroxide dissolved in 2.0 ml. of ethanol and 4.0 ml. of water. The mixture is stirred under nitrogen at ambient temperature for 15 min. and then cooled in the ice bath while a solution of ethyl 20-iodo-9-oxo-17,18,19-trinor-13-trans-prostenoate (434 mg.) (Example 95) in 3 ml. of ethanol is added. The reaction mixture is stirred successively at 0° for 15 min., at ambient temperature for 15 min., and at 40° for 5 min. The mixture is diluted with water and extracted with ether. The extract is washed successively with water and saturated sodium chloride, dried, and evaporated. The crude product is purified by chromatography on silica gel to give an oil, IR 1740 cm$^{-1}$ (ester and ketone carbonyls) and 967 cm$^{-1}$ (trans vinyl group); NMR (CCl$_4$)δ2.47 ppm (multiplet, methylenethio groups).

EXAMPLES 109–119

Treatment according to the procedure of Example 108, of the various 20-iodo-17,18,19-trinor-trans-prostenoates of Table VI (below) with sodium ethyl mercaptide (prepared in situ as in Example 108) is productive of the various 18-thiaprostenoates of the Table.

TABLE VI

| Example | Starting 20-Iodoprostenoate of Example | Product 18-Thiaprostenoate |
|---|---|---|
| 109 | 98 | ethyl 9-oxo-18-thia-6,7-dinor-13-trans-prostenoate |
| 110 | 99 | ethyl 9-oxo-18-thia-3,4,5,6,7-pentanor-13-trans-prostenoate |
| 111 | 101 | ethyl 9-oxo-18-thia-7a,7b-bis-homo-13-trans-prostenoate |
| 112 | 103 | ethyl 9-oxo-18-thia-10a-homo-13-trans-prostenoate |
| 113 | 104 | ethyl 9-oxo-18-thia-10a-homo-5,6-7-trinor-13-trans-prostenoate |
| 114 | 106 | ethyl 9-oxo-18-thia-7a,10a-bis-homo-13-trans-prostenoate |

EXAMPLE 115

Preparation of ethyl 9,9-ethylenedioxy-20-iodo-17,18,19-trinor-13-trans-prostenoate A solution of 25.2 g. of ethyl 20-iodo-9-oxo-17,18,19-trinor-13-trans-prostenoate (Example 95), 5.6 ml. of ethylene glycol and 110 mg. of p-toluenesulfonic acid monohydrate in 170 ml. of benzene is refluxed for 4 hours with azeotropic removal of water. The solution is concentrated to a volume of 50 ml. Column chromatography of the solution on Florisil with benzene gives a liquid, IR 1740 (ester carbonyl, 967 (trans vinyl group), and 952 cm$^{-1}$ (ethylene ketal).

EXAMPLES 116–120

Ketalization with ethylene glycol in the presence of p-toluenesulfonic acid of the appropriate 20-iodo-9-oxo-prostenoates by the procedure of Example 115 provides the ketals of Table VII, which follows.

TABLE VII

| Example | Starting Ketone of Example | Product |
| --- | --- | --- |
| 116 | 99 | ethyl 9,9-ethylenedioxy-20-iodo-3,4,5,6,7,17,18,19-octanor-13-trans-prostenoate |
| 117 | 98 | ethyl 9,9-ethylenedioxy-20-iodo-6,7,17,18,19-pentanor-13-trans-prostenoate |
| 118 | 104 | ethyl 9,9-ethylenedioxy-20-iodo-10a-homo-5,6,7,17,18,19-hexanor-13-trans-prostenoate |
| 119 | 106 | ethyl 9,9-ethylenedioxy-20-iodo-7a,10a-bis-homo-17,18,19-trinor-13-trans-prostenoate |
| 120 | 96 | ethyl 9,9-ethylenedioxy-20-iodo-13-trans-prostenoate |

EXAMPLE 121

Preparation of ethyl 9,9-ethylenedioxy-18-oxa-13-trans-prostenoate

To a stirred, ice-cold suspension of 1.68 g. of 57% sodium hydride in oil and 20 ml. of dimethylformamide (DMF) is added a solution of 2.5 ml. of ethanol in 5 ml. of DMF over a 15 min. period. The mixture evolves gas and is stirred at room temperature for 45 min. To the resulting suspension is added a solution of 9.57 g. of ethyl 9,9-ethylenedioxy-20-iodo-17,18,19-trinor-13-trans-prostenoate (Example 115) in 15 ml. of DMF over a 10 min. period at 10°–15° C. The resulting dark mixture is stirred at ambient temperature for 45 min. and then poured into 200 ml. of ice water. The mixture is brought to pH 7 with 4N HCl and extracted with ether. The extract is washed with brine, dried over MgSO$_4$, and concentrated. Column chromatography of the residue on silica gel with benzene-ether mixtures gives a liquid, IR 1740 (ester carbonyl, 967 (trans vinyl group), and 952 cm$^{-1}$ (ethylene ketal); nmr 3.4δ(triplet superimposed on quartet, O-methylene ether groups).

EXAMPLES 122–124

Treatment of the appropriate 20-iodoprostenoate ketals with sodium ethoxide by the procedure of Example 121 is productive of the 18-oxaprostenoate ketals of Table VIII, which follows.

TABLE VIII

| Example | Starting 20-Iodoprostenoate Ketal of Example | Product |
| --- | --- | --- |
| 122 | 116 | ethyl 9,9-ethylenedioxy-18-oxa-3,4,5,6,7-pentanor-13-trans-prostenoate |
| 123 | 118 | ethyl 9,9-ethylenedioxy-18-oxa-10a-homo-5,6,7-trinor-13-trans-prostenoate |
| 124 | 119 | ethyl 9,9-ethylenedioxy-18-oxa-7a,10a-bis-homo-13-trans-prostenoate |

EXAMPLE 125

Preparation of 2-(4-carbethoxybutyl)-2-cyclopentenonemethoxime

Treatment of 2-(4-carbethoxybutyl)-2-cyclopentenone (Example 31) with methoxyamine hydrochloride in the manner described in Example 32 gives an oil, b.p. 107°–109° C. (0.05 mm). IR (film): 1740, 1628, 1050, 885 cm$^{-1}$. $\lambda_{max}$ (MeOH) 243 (13,600).

EXAMPLE 126

Preparation of 2-(5-hydroxypentyl)-2-cyclopentenomethoxime

Treatment of 2-(4-carbethoxybutyl)-2-cyclopentenomethoxime (Example 125) with diisobutyl aluminum hydride in the manner described in Example 33 gives crystals, m.p. 33°–35° C. IR (KBr)3420, 1630, 1050, 886 cm$^{-1}$. $\lambda_{max}^{MeOH}$ 243 (12,020).

EXAMPLE 127

Preparation of 2-(5-tosyloxypentyl)-2-cyclopentenomethoxime

Treatment of 2-(5-hydroxypentyl)-2-cyclopentenomethoxime (Example 126) with p-toluenesulfonyl chloride in pyridine in the manner described in Example 34 gives a colorless oil. IR (film) 1600, 1190, 1180, 1050, 885 cm$^{-1}$.

EXAMPLE 128

Preparation of 2-(6,6-dicarbethoxyoctyl)-2-cyclopentenomethoxime

To a solution of sodio diethyl ethylmalonate, prepared from 1.63 g. (0.0387 mole) of sodium hydride in mineral oil (57.2%), 100 ml. of ethylene glycol dimethyl ether and 8.5 g. (0.0452 mole) of ethyl diethyl malonate, is added 7.5 g. of tosylate from Example 127 in 20 ml. of ethylene glycol dimethyl ether and the mixture is refluxed for 3 hours and then allowed to stand at room temperature for 18 hours under nitrogen atmosphere. The reaction mixture is filtered and most of the solvent is removed. The mixture is partitioned between cold dilute hydrochloric acid and diethyl ether, and the organic phase is washed with water and saturated brine, dried (MgSO$_4$), and evaporated to yield an oil. The excess ethyl diethyl malonate is distilled off under reduced pressure to yield 6.7 g. of a yellow oil. IR (film) 1755, 1728, 1627, 1050, 885 cm$^{-1}$.

EXAMPLE 129

Preparation of 2-(6,6-dicarboxyoctyl)-2-cyclopentenomethoxime

Treatment of 2-(6,6-dicarbethoxyoctyl)-2-cyclopentenomethoxime (Example 128) with potassium hydroxide, and 1:1 aqueous methanol in the manner described in Example 36 gives a light yellow oil.

EXAMPLE 130

Preparation of 2-(6-carboxyoctyl)-2-cyclopentenomethoxime

In the manner described in Example 37, treatment of 2-(6,6-dicarboxyoctyl)-2-cyclopentenomethoxime (Example 129) with xylene at reflux for 18 hours gives a yellow oil.

EXAMPLE 131

Preparation of 2-(6-carboxyoctyl)-2-cyclopentenone

Treatment of 2-(6-carboxyoctyl)-2-cyclopentenomethoxime (Example 130) with acetone and 2N hydrochloric acid in the manner described in Example 38 gives a light yellow oil.

EXAMPLE 132

Preparation of 2-(6-carbethoxyoctyl)-2-cyclopentenone

Treatment of 2-(6-carboxyoctyl)-2-cyclopentenone (Example 131) with thionyl chloride and then treatment of the acid chloride with ethanol in the manner described in Example 456 gives an amber oil. The oil is placed on a magnesia-silica gel column and eluted with 3:1 benzene:ether. The solvent is removed and the residue is distilled, b.p. 122° C. (0.06 mm).

EXAMPLES 133-138

Treatment of 2-(6-carbethoxyoctyl)-2-cyclopentenone (Example 132) in the manner of Example 44 with the reagents prepared from the alkyne indicated in Table IX below, diisobutylaluminum hydride and methyl lithium is productive of the prostenoate esters of the first three Examples of this table. Saponification of the ester by the procedure of Example 139 provides the corresponding prostenoic acids.

TABLE IX

| Example | Starting Alkyne or Prostenoate ester | Product |
|---|---|---|
| 133 | 1-octyne | ethyl 2-ethyl-9-oxo-13-trans-prostenoate |
| 134 | cis-5-octen-1-yne | ethyl 2-ethyl-9-oxo-13-trans-17-cis-prostadienoate |
| 135 | 8-chloro-1-octyne | ethyl 2-ethyl-9-oxo-20-chloro-13-trans-prostenoate |
| 136 | Example 133 | 2-ethyl-9-oxo-13-trans-prostenoic acid |
| 137 | Example 134 | 2-ethyl-9-oxo-13-trans-17-cis-prostadienoic acid |
| 138 | Example 135 | 2-ethyl-9-oxo-chloro-13-trans-prostenoic acid |

EXAMPLE 130

Preparation of 20-butyl-9-oxo-13-trans-prostenoic acid

A solution of 2.33 g. of ethyl 20-butyl-9-oxo-13-trans-prostenoate (Example 45) and 1.30 g. of potassium hydroxide in 35 ml. of methanol and 3.5 ml. of water is allowed to stand at room temperature for 24 hours. The reaction mixture is concentrated in vacuo, diluted with water, and washed with ether. The aqueous phase is acidified to pH 2 and extracted with ether. The extract is washed with saturated sodium chloride, dried, and evaporated to give an oil, IR 1745 cm$^{-1}$ (ketone carbonyl), 1710 cm$^{-1}$ (acid carbonyl), and 967 cm$^{-1}$ (trans vinyl group).

EXAMPLE 140

Preparation of 9-oxo-13-trans-prostenoic acid

A mixture of 0.140 g. of ethyl 9-oxo-13-trans-prostenoate (Example 44) and 0.072 g. of potassium hydroxide in 6 ml. of 1:1 aqueous methanol is stirred at ambient temperature for 17 hours. The resulting solution is acidified with hydrochloric acid, extracted with diethyl ether, and the organic phase is washed with water and saturated brine, dried, and the solvent removed to yield 0.128 g. of an oil, IR 1739 cm$^{-1}$ (ketone carbonyl) 1706 cm$^{-1}$ (acid carbonyl), 969 cm$^{-1}$ (trans vinyl group); NMR (CDCl$_3$) 5.34–5.67 (multiplet, 2H, vinyl protons, J trans=15 Hz), 10.47 (broad singlet, 1H, carboxyl proton, exchangeable); Mass spectrum, parent peak at 322 mu.

EXAMPLE 141

Preparation of 9-oxo-6,7-dinor-13-trans-prostenoic acid

In the manner described in Example 140, ethyl 9-oxo-6,7-dinor-13-trans-prostenoate (Example 56) is saponified with potassium hydroxide, acidified, and worked-up by ether extraction and evaporative distillation at 160° C. (0.005 Torr) to yield a colorless oil.

EXAMPLES 142–195

In the manner described in Example 139, the carboxylic acids of Table X (below) are prepared by saponification of the corresponding ethyl esters at room temperature in methanol-water followed by acidification and extraction with ether. Infrared characterization of the cyclopentanone derivatives gives bands at about 1745 cm$^{-1}$ (ketone carbonyl), 1710 cm$^{-1}$ (acid carbonyl) and 967 cm$^{-1}$ (trans vinyl group). The cyclohexanone derivatives also show the 967 cm$^{-1}$ band, but the carboxylic acid and ketone carbonyl functions give bands occurring at about 1715 cm$^{-1}$.

TABLE X

| Example | Starting Ester of Example | Product |
|---|---|---|
| 142 | 46 | 9-oxo-18,19,20-trinor-13-trans-prostenoic acid |
| 143 | 47 | 15-methyl-9-oxo-17,18,19,20-tetranor-13-trans-prostenoic acid |
| 144 | 48 | 20-chloro-9-oxo-13-trans-prostenoic acid |
| 145 | 49 | 9-oxo-20-nor-13-trans-prostenoic acid |
| 146 | 50 | 20-methyl-9-oxo-13-trans-prostenoic acid |
| 147 | 51 | 17-methyl-9-oxo-19,20-dinor-13-trans-prostenoic acid |
| 148 | 52 | 20-chloro-9-oxo-17,18,19-trinor-13-trans-prostenoic acid |
| 149 | 53 | 9-oxo-13-propyl-18,19,20-trinor-13-trans-prostenoic acid |
| 150 | 55 | 9-oxo-13-trans-17-cis-prostadienoic acid |
| 151 | 57 | 20-chloro-9-oxo-6,7-dinor-13-trans-prostenoic acid |
| 152 | 58 | 9-oxo-6,7,20-trinor-13-trans-prostenoic acid |
| 153 | 59 | 9-oxo-6,7-dinor-13-trans-17-cis-prostadienoic acid |
| 154 | 60 | 20-chloro-9-oxo-6,7,17,18,19-pentanor-13-trans-prostenoic acid |
| 155 | 61 | 17-methyl-9-oxo-6,7,19,20-tetranor-13-trans-prostenoic acid |
| 156 | 62 | 9-oxo-13-propyl-6,7,18,19,20-pentanor-13-trans-prostenoic acid |
| 157 | 63 | 9-oxo-3,4,5,6,7-pentanor-13-trans-prostenoic acid |
| 158 | 64 | 9-oxo-3,4,5,6,7-pentanor-13-trans-17-cis-prostadienoic acid |
| 159 | 65 | 20-chloro-9-oxo-3,4,5,6,7,17,18,19-octanor-13-trans-prostenoic acid |
| 160 | 66 | 9-oxo-5,6,7-trinor-13-trans-prostenoic acid |
| 161 | 67 | 9-oxo-20-propyl-5,6,7-trinor-13-trans-prostenoic acid |
| 162 | 68 | 9-oxo-5,6,7,18,19,20-hexanor-13-trans-prostenoic acid |
| 163 | 69 | 20-chloro-9-oxo-5,6,7-trinor-13-trans-prostenoic acid |
| 164 | 70 | 9-oxo-7a,7b-bis-homo-13-trans-prostenoic acid |
| 165 | 71 | 20-chloro-9-oxo-7a,7b-bis-homo-17,18,19-trinor-13-trans-prostenoic acid |
| 166 | 72 | 20-butyl-9-oxo-7a,7b-bis-homo-13-trans-prostenoic acid |
| 167 | 73 | 15-methyl-9-oxo-7a,7b-bis-homo-17,18,19,20-tetranor-13-trans-prostenoic acid |
| 168 | 74 | 9-oxo-10a-homo-13-trans-prostenoic acid |
| 169 | 75 | 20-butyl-9-oxo-10a-homo-13-trans- |

TABLE X-continued

| Example | Starting Ester of Example | Product |
|---|---|---|
| | | prostenoic acid |
| 170 | 76 | 20-chloro-9-oxo-10a-homo-13-trans-prostenoic acid |
| 171 | 77 | 20-chloro-9-oxo-10a-homo-17,18,19-trinor-13-trans-prostenoic acid |
| 172 | 78 | 9-oxo-18,19,20-trinor-10a-homo-13-trans-prostenoic acid |
| 173 | 79 | 9-oxo-10a-homo-13-trans-17-cis-prostadienoic acid |
| 174 | 93 | 9-oxo-5,6,7-trinor-10a-homo-13-trans-17-cis-prostadienoic acid |
| 175 | 94 | 9-oxo-7a,10a-bis-homo-13-trans-17-cis-prostadienoic acid |
| 176 | 80 | 9-oxo-5,6,7-trinor-10a-homo-13-trans-prostenoic acid |
| 177 | 81 | 9-oxo-5,6,7,20-tetranor-10a-homo-13-trans-prostenoic acid |
| 178 | 82 | 20-chloro-9-oxo-5,6,7,17,18,19-hexanor-10a-homo-13-trans-prostenoic acid |
| 179 | 83 | 15-methyl-9-oxo-5,6,7,17,18,19,20-heptanor-10a-homo-13-trans-prostenoic acid |
| 180 | 84 | 9-oxo-7-nor-10a-homo-13-trans-prostenoic acid |
| 181 | 85 | 9-oxo-20-propyl-7-nor-10a-homo-13-trans-prostenoic acid |
| 182 | 86 | 17-methyl-9-oxo-7,19,20-trinor-10a-homo-13-trans-prostenoic acid |
| 183 | 87 | 20-chloro-9-oxo-7-nor-10a-homo-13-trans-prostenoic acid |
| 184 | 88 | 9-oxo-7a,10a-bis-homo-13-trans-prostenoic acid |
| 185 | 89 | 9-oxo-19,20-dinor-7a,10a-bis-homo-13-trans-prostenoic acid |
| 186 | 90 | 20-chloro-9-oxo-7a,10a-bis-homo-17,18,19-trinor-13-trans-prostenoic acid |
| 187 | 91 | 20-chloro-9-oxo-7a,10a-bis-homo-13-trans-prostenoic acid |
| 188 | 92 | 13-propyl-9-oxo-7a,10a-bis-homo-18,19,20-trinor-13-trans-prostenoate |
| 189 | 108 | 9-oxo-18-thia-13-trans-prostenoic acid |
| 190 | 109 | 9-oxo-18-thia-6,7-dinor-13-trans-prostenoic acid |
| 191 | 110 | 9-oxo-18-thia-3,4,5,6,7-pentanor-13-trans-prostenoic acid |
| 192 | 111 | 9-oxo-18-thia-7a,7b-bis-homo-13-trans-prostenoic acid |
| 193 | 112 | 9-oxo-18-thia-10a-homo-13-trans-prostenoic acid |
| 194 | 113 | 9-oxo-18-thia-10a-homo-5,6,7-trinor-13-trans-prostenoic acid |
| 195 | 114 | 9-oxo-18-thia-7a,10a-bis-homo-13-trans-prostenoic acid |

EXAMPLE 196

Preparation of ethyl 18-oxa-9-oxo-13-trans-prostenoate

A solution of 1.07 g. of ethyl 9,9-ethylenedioxy-18-oxa-13-trans-prostenoate (Example 121) and 27 mg. of p-toluenesulfonic acid monohydrate in 10 ml. of acetone is allowed to stand at room temperature for 17 hours. The bulk of the acetone is evaporated, and the residue is treated with 25 ml. of water and extracted with ether. The extract is washed successively with dilute NaHCO$_3$ and brine and dried over MgSO$_4$. Evaporation of the solvent gives an oil, IR 1740 (ester and ketone carbonyls) and 967 cm$^{-1}$ (trans vinyl group).

EXAMPLES 197–199

Treatment of the appropriate 18-oxaprostenoate ketals with acetone and p-toluenesulfonic acid by the procedure of Example 196 is productive of the ethyl 18-oxa-9-oxo-13-trans-prostenoates of Table XI, which follows.

TABLE XI

| Example | Starting 18-Oxa-prostenoate Ketal of Example | Product |
|---|---|---|
| 197 | 122 | ethyl 18-oxa-9-oxo-3,4,5,6,7-penta-nor-13-trans-prostenoate |
| 198 | 123 | ethyl 18-oxa-9-oxo-5,6,7-trinor-10a-homo-13-trans-prostenoate |
| 199 | 124 | ethyl 18-oxa-9-oxo-7a,10a-bis-homo-13-trans-prostenoate |

EXAMPLES 200–203

Saponification of the appropriate ethyl 18-oxa-9-oxo-13-trans-prostenoates by the procedure of Example 139 is productive of the 18-oxa-9-oxo-13-trans-prostenoic acids of Table XII which follows.

TABLE XII

| Example | Starting 18-Oxa-prostenoate of Example | Product |
|---|---|---|
| 200 | 196 | 18-oxa-9-oxo-13-trans-prostenoic acid |
| 201 | 197 | 18-oxa-9-oxo-3,4,5,6,7-pentanor-13-trans-prostenoic acid |
| 202 | 198 | 18-oxa-9-oxo-5,6,7-trinor-10a-homo-13-trans-prostenoic acid |
| 203 | 199 | 18-oxa-9-oxo-7a,10a-bis-homo-13-trans-prostenoic acid |

EXAMPLE 204

Preparation of 4-chloro-1-tetrahydropyranyloxybutane

To 9.25 g. (0.11 mole) of dihydropyran containing 3 drops of phosphorus oxychloride is added 10 g. (0.092 mole) of 4-chlorobutanol-1 dropwise over a period of 2 hours with stirring. The reaction mixture is then allowed to stir overnight at room temperature. The reaction mixture is concentrated, the residue is placed on a Florisil column and the product is eluted with benzene to give 14.4 g. (81%) of the subject compound as an oil.

EXAMPLE 205

Preparation of diethyl 1,1-dimethyl-5-tetrahydropyranylpentyl-malonate

To 486 mg. (0.02 g.-atoms) of magnesium in 5 ml. of toluene containing 1 molar equivalent of tetrahydrofuran per equivalent of magnesium and one percent iodine (calculated in weight of magnesium) is added dropwise 3.86 g. (0.02 mole) of 4-chloro-1-tetrahydropyranyloxybutane over a period of 1 hour with stirring, under nitrogen at 70° C. The reaction mixture is stirred at 70° C. for 4 hours. This reagent is then added dropwise to 3 g. (0.015 mole) of ethyl isopropylidenemalonate in 40 ml. of tetrahydrofuran containing 392 mg. of tetrakis[iodo(tri-n-butylphosphine)copper (I)] and stirred at room temperature for 2 hours. The reaction mixture is poured into cold dilute hydrochloric acid and extracted with ether. The ether extract is dried over magnesium sulfate and concentrated to give 5.92 g. of subject product as an oil.

EXAMPLE 206

Preparation of diethyl 1,1-dimethyl-5-hydroxypentylmalonate

A solution of 3.5 g. (0.01 mole) of diethyl 1,1-dimethyl-5-tetrahydrofuranyloxypentylmalonate in 70 ml. of ethanol containing 3 ml. of hydrochloric acid is allowed to stir at room temperature for 18 hours. The solution is concentrated, diluted with water and extracted with ether. The ether extract is washed with water, dried over magnesium sulfate and concentrated to give 3.262 g. of a light yellow oil. The oil is purified by distillation, b.p. 116°-117° C. (0.05 mm).

EXAMPLE 207

Preparation of 3,3-dimethyl-7-hydroxyheptanoic acid

A mixture of 32 g. (0.117 mole) of diethyl 1,1-dimethyl-5-hydroxypentylmalonate, 25 g. of potassium hydroxide and 600 ml. of methanol-water (1:1) is heated at reflux for 8 hours and then allowed to stand at room temperature for 18 hours. The methanol is removed, diluted with water and the reaction mixture is acidified with concentrated hydrochloric acid. The mixture is extracted with ether. The extract is washed with water and saline, dried over anhydrous magnesium sulfate and concentrated to give 27 g. of 1,1-dimethyl-5-hydroxypentylmalonic acid. This crude oil is dissolved in 200 ml. of bis-(2-methoxyethyl)ether and is heated at reflux for 4 hours and then allowed to stand at room temperature overnight. The solvent is removed and the reaction mixture is diluted with water and extracted with ether. The organic solution is washed with saline, dried over magnesium sulfate and concentrated to give 18 g. of product as an oil.

EXAMPLE 208

Preparation of ethyl 3,3-dimethyl-7-chloroheptanoate

To a solution of 3.484 g. (0.02 mole) of 3,3-dimethyl-7-hydroxyheptanoic acid in 25 ml. of chloroform containing 3 drops of dimethylformamide is added 5.8 ml. (0.08 mole) of thionyl chloride and the solution is then heated at reflux for 3-4 hours. The solution is concentrated to give the intermediate 3,3-dimethyl-7-chloro-1-heptanoyl chloride. The acid chloride is dissolved in a minimum amount of benzene and added slowly to 20 ml. benzene, 10 ml. of ethanol and 2.65 ml. of collidine. The solution is heated at reflux for one hour and then concentrated. The residue is dissolved in ether, washed with water, dilute sodium bicarbonate solution and saline. The organic solution is dried over magnesium sulfate and concentrated to give 3.57 g. of product as a yellow oil.

EXAMPLE 209

Preparation of ethyl 3,3-dimethyl-7-iodoheptanoate

To a solution of 3.57 g. (0.0162 mole) of ethyl 3,3-dimethyl-7-chloroheptanoate in 100 ml. of methyl ethyl ketone is added 4 g. of sodium iodide and the mixture heated at reflux for 18 hours. The reaction mixture is cooled, filtered and concentrated. The residue is partitioned between ether and water. The aqueous phase is extracted several times with ether. The extract is washed with sodium bisulfite solution, water and saline. The organic solution is dried over magnesium sulfate and concentrated to give 4.182 g. of a yellow oil. The material is purified by distillation, b.p. 86°-87° C. (0.18 Torr).

EXAMPLE 210

Preparation of 2-carbalkoxy(methyl/ethyl)-2-(6-carbethoxy-5,5-dimethylhexyl)cyclopentan-1-one This compound is prepared by treatment of sodio cyclopentanone carboxylate enolate with ethyl 3,3-dimethyl-7-iodoheptanoate by the procedure described in Example 1.

EXAMPLE 211

Preparation of 2-(6-carboxy-5,5-dimethylhexyl)cyclopentan-1-one

This compound is prepared by decarbalkoxylation of 2-carbalkoxy (mixed methyl and ethyl ester)-2-(6-carbethoxy-5,5-dimethylhexyl)cyclopentan-1-one by the procedure described in Example 2.

EXAMPLE 212

Preparation of 2-(6-carbethoxy-5,5-dimethylhexyl)cyclopentan-1-one

Esterification of 2-(6-carboxy-5,5-dimethylhexyl)cyclopentan-1-one with ethanol by the procedure of Example 456 is productive of the subject compound.

EXAMPLE 213

Preparation of 1-acetoxy-2-(6-carbethoxy-5,5-dimethylhexyl)cyclopent-1-ene

This compound is prepared from 2-(6-carbethoxy-5,5-dimethylhexyl)cyclopentan-1-one and acetic anhydride by the process described in Example 20.

EXAMPLE 214

Preparation of 2-(6-carbethoxy-5,5-dimethylhexy)cyclopent-2-en-1-one

This compound is prepared from 1-acetoxy-2-(6-carbethoxy-5,5-dimethylhexyl)cyclopent-1-ene via bromination and dehydrobromination according to the procedure described in Example 28.

EXAMPLE 215

Preparation of 2-(3-carbethoxypropyl)-1-methoximino-2-cyclopentene

In the manner described for the preparation of the compound of Exammple 32, 2-(3-carbethoxypropyl)-1-methoximino-2-cyclopentene is prepared from 2-(3-carbethoxypropyl)-2-cyclopentenone (Example 30) and methoxyamine hydrochloride.

EXAMPLE 216

Preparation of 2-(4-hydroxybutyl)-1-methoximino-2-cyclopentene

In the manner described for the preparation of the compound of Example 33, 2-(4-hydroxybutyl)-1-methoximino-2-cyclopentene is prepared from 2-(3-carbethoxypropyl)-1-methoximino-2-cyclopentenone and diisobutylaluminum hydride.

EXAMPLE 217

Preparation of 2-(6-carbethoxy-5-oxahexyl)-1-methoximino-2-cyclopentene

To an ice cold solution of 4.833 g. (0.0266 mole) of 2-(4-hydroxypentane)-1-methoximino-2-cyclopentene in 50 ml. of dry tetrahydrofuran under nitrogen is added 16.7 ml. of 1.6 molar n-butyl lithium in hexane, dropwise. The reaction mixture is stirred for 0.5 hour and then 4.85 g. (0.029 mole) of ethyl bromoacetate is added dropwise. The reaction mixture is stirred overnight at room temperature and then refluxed for 1.5 hours. The reaction is cooled and poured into water and extracted several times with ether. The ether extracts are washed with saline, dried over magnesium sulfate, and concentrated. The residue is placed on an alumina column, chloroform being used as a wash solvent. The combind washings are concentrated to dryness to give 4.903 g. of product an a yellow oil.

EXAMPLE 218

Preparation of 2-(6-carboxy-5-oxahexyl)-2-cyclopentenone

In the manner described in Example 38, treatment of 2-(6-carbethoxy-5-oxahexyl)-1-methoximino-2-cyclopentene with acetone and 2N hydrochloric acid at reflux gives the subject compound as a yellow oil.

EXAMPLE 219

Preparation of 2-(6-carbethoxy-5-oxahexyl)-2-cyclopentenone

In the manner described in Example 39, treatment of 2-(6-carboxy-5-oxahexyl)-2-cyclopentenone with p-toluenesulfonic acid in ethanol produces the subject product as a light yellow oil.

EXAMPLE 220

Preparation of 2-(4-p-toluenesulfonyloxybutyl)-1-methoximino-2-cyclopentene

In the manner described in Example 34, treatment of 2-(4-hydroxybutyl)-1-methoximino-2-cyclopentene with p-toluene sulfonyl chloride in pyridine gives the subject product as a light yellow oil; IR (film): 1600, 1190, 1050, 885 cm$^{-1}$.

EXAMPLE 221

Preparation of 2-(6-carbethoxy-5-thiahexyl)-1-methoximino-2-cyclopentene

To a stirred mixture of 1.465 g. (0.0348 mole) of sodium hydride (57.2% in mineral oil) in 50 ml. of dimethoxyethane, under nitrogen, is added slowly 4.8 g. (0.0347 mole) of ethyl-2-mercaptoacetate. The reaction mixture is stirred at room temperature for one hour and then a solution of 7.8 g. (0.0231 mole) of 2-(4-p-toluenesulfonyloxybutyl)-1-methoximino-2-cyclopentene in 30 ml. of dimethoxyethane is added dropwise and stirred at room temperature for 18 hours. The solution is heated at reflux for one hour, cooled and poured into cold dilute hydrochloric acid and then extracted with ether. The combined ether extracts are washed with saline, dried over magnesium sulfate and evaporated to give 7.6 g. of subject product as a yellow oil.

EXAMPLE 222

Preparation of 2-(6-carboxy-5-thiahexyl)-2-cyclopentenone

In the manner described in Example 38, treatment of 2-(6-carbethoxy-5-thiahexyl)-1-methoximino-2-cyclopentene with acetone and 2N hydrochloric acid at reflux gives the subject product as a yellow oil.

EXAMPLE 223

Preparation of 2-(6-carbethoxy-5-thiahexyl)-2-cyclopentenone

In the manner described in Example 39, treatment of 2-(6-carboxy-5-thiahexyl)-2-cyclopentenone with p-toluenesulfonic acid in ethanol gives the subject ester as a yellow oil.

EXAMPLE 224

Preparation of ethyl 9-oxo-3,3-dimethyl-13-trans-prostenoate

In the manner described in Example 44, treatment of 2-(6-carbethoxy-5,5-dimethylhexyl)cyclopent-2-en-1-one with the reagent prepared from 1-octyne, diisobutylaluminum hydride and methyl lithium provides the subject product as a yellow oil.

EXAMPLE 225

Preparation of ethyl 9-oxo-3-thia-13-trans-prostenoate

In the manner described in Example 44, treatment of 2-(6-carbethoxy-5-thiahexyl)-2-cyclopentenone with the reagent prepared from 1-octyne, diisobutylaluminum hydride and methyl lithium gives the subject 3-thiaprostenoate as a yellow oil.

EXAMPLE 226

Preparation of ethyl 3-oxa-9-oxo-13-trans-prostenoate

In the same manner as for the preparation of the compound of Example 44, ethyl 3-oxa-9-oxo-13-trans-prostenoate is prepared by the addition of 2-(6-carbethoxy-5-oxahexyl)-2-cyclopentenone to the reagent prepared from 1-octyne, diisobutylaluminum hydride and methyl lithium.

EXAMPLES 227-238

In the manner of Example 44, treatment of the gem-dimethyl, oxa, or thia cyclopentenone esters of Examples 214, 219 and 223, respectively, with the alanate complex obtained from the alkynes indicated in Table XIII below, diisobutylaluminum hydride and methyl lithium, is productive of the 3,3-dimethyl, 3-oxa, or 3-thia prostenoates of the Table.

TABLE XIII

| Example | Starting Cyclopentenone | Starting Alkyne | Product |
|---|---|---|---|
| 227 | 2-(6-carbethoxy-5,5-dimethylhexyl)-cyclopent-2-en-1-one (Example 214) | 8-chloro-1-octyne | ethyl 20-chloro-3,3-dimethyl-9-oxo-13-trans-prostenoate |
| 228 | 2-(6-carbethoxy-5,5-dimethylhexyl)-cyclopent-2-en-1-one (Example 214) | 5-chloro-1-pentyne | ethyl 20-chloro-3,3-dimethyl-9-oxo-17,18,19-trinor-13-trans-prostenoate |
| 229 | 2-(6-carbethoxy-5,5-dimethylhexyl)-cyclopent-2-en-1-one (Example 214) | cis-5-octen-1-yne | ethyl 3,3-dimethyl-9-oxo-13-trans-17-cis-prostadienoate |
| 230 | 2-(6-carbethoxy-5,5-dimethylhexyl)-cyclopent-2-en-1-one (Example 214) | 1-nonyne | ethyl 3,3,20-trimethyl-9-oxo-13-trans-prostenoate |
| 231 | 2-(6-carbethoxy-5-oxahexyl)-2-cyclopentenone (Example 219) | 8-chloro-1-octyne | ethyl 20-chloro-3-oxa-9-oxo-13-trans-prostenoate |
| 232 | 2-(6-carbethoxy-5-oxahexyl)-2-cyclopentenone (Example 219) | 5-chloro-1-pentyne | ethyl 20-chloro-3-oxa-9-oxo-17,18,19-trinor-13-trans-prostenoate |
| 233 | 2-(6-carbethoxy-5-oxahex- | cis-5-octen-1- | ethyl 3-oxa-9-oxo-13-trans-17-cis-prostadienoate |

TABLE XIII-continued

| Example | Starting Cyclopentenone | Starting Alkyne | Product |
|---|---|---|---|
| | yl)-2-cyclo-pentenone (Example 219) | yne | |
| 234 | 2-(6-carbeth-oxy-5-oxahex-yl)-2-cyclo-pentenone (Example 219) | 1-nonyne | ethyl 20-methyl-3-oxa-9-oxo-13-trans-prostenoate |
| 235 | 2-(6-carbeth-oxy-5-thiahex-yl)-2-cyclo-pentenone (Example 223) | 8-chloro-1-octyne | ethyl 20-chloro-9-oxo-3-thia-13-trans-prostenoate |
| 236 | 2-(6-carbeth-oxy-5-thiahex-yl)-2-cyclo-pentenone (Example 223) | 5-chloro-1-pentyne | ethyl 20-chloro-9-oxo-3-thia-17,18,19-trinor-13-trans-prostenoate |
| 237 | 2-(6-carbeth-oxy-5-thiahex-yl)-2-cyclo-pentenone (Example 223) | cis-5-octen-1-yne | ethyl 9-oxo-3-thia-13-trans-17-cis-prostadieno-ate |
| 238 | 2-(6-carbeth-oxy-5-thiahex-yl)-2-cyclo-pentenone (Example 223) | 1-hexyne | ethyl 9-oxo-3-thia-19,20-dinor-13-trans-prostenoate |

EXAMPLE 239

Preparation of 2-(carbethoxymethyl)-3-(1-trans-octenyl)-1,1-dioxolano-cyclopentane A mixture of 10.142 g. (0.0362 mole) of 2-(carbethoxymethyl)-3-(1-octenyl)cyclopentanone (ethyl 9-oxo-3,4,5,6,7-pentanor-13-trans-prostenoate, Example 63), 3.49 g. (0.0562 mole) of ethylene glycol, 0.344 g. of p-toluenesulfonic acid monohydrate, and 30 ml. of benzene is refluxed for 4.5 hours with azeotropic removal of water. The mixture is cooled, placed onto a column of 130 g. of Florisil in benzene and the ketal is eluted off with benzene. The filtrate is evaporated to yield 9.53 g. of a colorless oil.

EXAMPLE 240

Preparation of 2-(formylmethyl)-3-(1-trans octenyl)-1,1-dioxolano-cyclopentane

To a solution of 1.00 g. (0.00308 mole) of 2-(carbethoxymethyl)-3-(1-trans-octenyl)-1,1-dioxolano cyclopentane in 5 ml. of heptane at −78° C. and under nitrogen is added dropwise 2.60 ml. of a solution of 25% diisobutylaluminum hydride in hexane. The resulting solution is stirred at −78° C. for 2.5 hours and then poured into cold dilute hydrochloric acid. The organic phase is washed with saturated brine, dried (Na$_2$SO$_4$), and evaporated to yield 0.863 g. of a colorless oil. IR 2695, 1723, 1045, 970 cm$^{-1}$.

EXAMPLE 241

Preparation of 2-(6-carboxy-2-cis-hexenyl)-3-(1-trans-octenyl)-1,1-dioxolano cyclopentane A mixture of 0.194 g. (0.007952 mole) of sodium hydride (free of mineral oil) and 5.5 ml. of dimethylsulfoxide is heated to 70° C. until gas evolution ceases under a nitrogen atmosphere. The resulting solution is cooled below room temperature and treated with a solution of 1.400g. (0.00316 mole) of 4-carboxybutyltriphenyl phosphonium bromide [E. J. Corey et al., J. Am. Chem. Soc., 91, 5675 (1969)] in 6 ml. of dimethylsulfoxide. To the resulting red solution is added 0.738 g. (0.00263 mole) of 2-(formylmethyl)-3-(1-trans-octenyl)-1,1-dioxolano cyclopentane in 2 ml. of dimethylsulfoxide and the mixture is stirred at room temperature for 2.25 hours. The mixture is poured into ice water, sodium hydroxide solution is added to pH 12, and the neutral materials are extracted with diethyl ether. The basic phase is acidified with dilute hydrochloric acid and is extracted with diethyl ether. The organic phase is washed with water and saturated brine, dried (Na$_2$SO$_4$), and evaporated to a semicrystalline mass. The latter is triturated with hot hexane, the solids are filtered off, and the filtrate is evaporated to yield an oil. IR: 1705, 1040, 970, 722 cm$^{-1}$.

EXAMPLE 242

Preparation of 9-oxo-5-cis-13-trans-prostadienoic acid

A solution of 0.726 g. of 2-(6-carboxy-2-cis-hexenyl)-3-(1-trans-octenyl)-1,1-dioxolano cyclopentane and 19 mg. of p-toluenesulfonic acid monohydrate in 30 ml. of acetone is stirred at ambient temperatures for 66 hours. The volatile material is removed in vacuo and the residue is passed through a column of silica gel in chloroform collecting those fractions which contain product. The solvent is evaporated to yield the subject product as an oil. IR: 1740, 1705, 970, 722 cm$^{-1}$.

EXAMPLES 243-257

Saponification of the esters of the following table by the procedure of Example 139 is productive of the carboxylic acids of this table.

TABLE XIV

| Example | Starting Ester of Example | Product |
|---|---|---|
| 243 | 224 | 3,3-dimethyl-9-oxo-13-trans-prostenoic acid |
| 244 | 225 | 9-oxo-3-thia-13-trans-prostenoic acid |
| 245 | 226 | 9-oxo-3-oxa-13-trans-prostenoic acid |
| 246 | 227 | 20-chloro-3,3-dimethyl-9-oxo-13-trans-prostenoic acid |
| 247 | 228 | 20-chloro-3,3-dimethyl-9-oxo-17,18,19-trinor-13-trans-prostenoic acid |
| 248 | 229 | 3,3-dimethyl-9-oxo-13-trans-17-cis-prostadienoic acid |
| 249 | 230 | 3,3,20-trimethyl-9-oxo-13-trans-prostenoic acid |
| 250 | 231 | 20-chloro-3-oxa-9-oxo-13-trans-prostenoic acid |
| 251 | 232 | 20-chloro-3-oxa-9-oxo-17,18,19-trinor-13-trans-prostenoic acid |
| 252 | 233 | 3-oxa-9-oxo-13-trans-17-cis-prostadienoic acid |
| 253 | 234 | 20-methyl-3-oxa-9-oxo-13-trans-prostenoic acid |
| 254 | 235 | 20-chloro-9-oxo-3-thia-13-trans-prostenoic acid |
| 255 | 236 | 20-chloro-9-oxo-3-thia-17,18,19-trinor-13-trans-prostenoic acid |
| 256 | 237 | 9-oxo-3-thia-13-trans-17-cis-prostadienoic acid |
| 257 | 238 | 9-oxo-3-thia-19,20-dinor-13-trans-prostenoic acid |

EXAMPLE 258

Prepaation of 9-oxo-13-trans-prostenoyl chloride and 9 oxo-13-trans-prostenamide A solution of 5.00 g. of 9-oxo-13-trans-prostenoic acid and 2.67 g. of thionyl chloride in 15 ml. of chloroform is warmed to reflux until gas evolution ceases. The resulting solution, containing 9-oxo-13-trans-prostenoyl chloride, is cooled, poured into cold ammonia, and stirred for 0.5 hour. The mixture is extracted into chloroform, the organic phase is washed with dilute sodium bicarbonate, water, and saturated brine, dried, and the solvent evaporated. The residue is purified by chromatography on silica gel to yield an oil, IR 1739 cm$^{-1}$ (ketone carbonyl), 1664 cm$^{-1}$ (amide carbonyl), 969 cm$^{-1}$ (trans vinyl group).

EXAMPLE 259

Preparation of 9-oxo-13-trans-prostenoyl chloride and N-(3-dimethylaminopropyl)-9-oxo-13-trans-prostenamide A solution of 8 g. of 9-oxo-13-trans-prostenoic acid and 2.58 ml. of thionyl chloride in 40 ml. of chloroform containing 8 drops of dimethylformamide is warmed to reflux until gas evolution ceases. The reaction mixture is concentrated and the residue is dissolved in ether. The resulting solution is slowly added to 7.65 g. of 3-dimethylaminopropylamine in 600 ml. of ether and stirred at room temperature for one hour. The reaction mixture is filtered and the filtrate is washed with dilute sodium bicarbonate, water and saturated brine, dried, and the solvent evaporated. Excess 3-dimethylaminopropylamine is distilled off by heating under high vacuum. The residue is purified by chromatography on Florisil to yield an oil, IR 1745 cm$^{-1}$ (ketone carbonyl), 1660 cm$^{-1}$ (amide carbonyl), 969 cm$^{-1}$ (trans vinyl group).

EXAMPLE 260

Preparation of 4-{7-[(2-trans-octenyl)-5-oxocyclopentyl]heptanoyl}-morpholine (morpholine amide of 9-oxo-13-trans-prostenoic acid)

A solution of 3 g. of 9-oxo-13-trans-prostenoic acid and 1.6 ml. of thionyl chloride in 15 ml. of chloroform containing 4 drops of dimethylformamide is warmed to reflux until gas evolution ceases. The reaction mixture is concentrated and the residue dissolved in ether. The resulting solution is slowly added to 2 g. of morpholine in 30 ml. of ether and stirred for one hour at room temperature. The reaction mixture is filtered and the filtrate washed with 10% hydrochloric acid, dilute sodium bicarbonate and saturated brine, dried and the solvent evaporated. The residue is purified by chromatography on Florisil to yield an oil, IR 1749 cm$^{-1}$; (ketone carbonyl), 1660 cm$^{-1}$ (amide carbonyl), 969 cm$^{-1}$ (trans vinyl group).

EXAMPLES 261–342

In the manner described in Examples 258, 259, or 260, treatment of the appropriate prostenoic acid with thionyl chloride is productive of the correponding prostenoic acid chloride, which on further treatment with the amine indicated on Table XV, which follows, furnished the corresponding prostenoic acid amide of the Table.

TABLE XV

| Ex. | Starting Prostenoic Acid of Example | Amine | Prostenoic Acid Amide Product |
|---|---|---|---|
| 261 | 140 | dimethyl amine | N,N-dimethyl-9-oxo-13-trans-prostenamide |
| 262 | 161 | di-n-butyl amine | N,N-di-n-butyl-9-oxo-20-propyl-5,6,7-trinor-13-trans-prostenamide |
| 263 | 142 | di-n-octyl amine | N,N-di-n-octyl-9-oxo-18,19,20-trinor-13-trans-prostenamide |
| 264 | 187 | di-isobutyl amine | N,N-di-isobutyl-20-chloro-9-oxo-7a,10a-bis-homo-13-trans-prostenamide |
| 265 | 140 | methyl amine | N-methyl-9-oxo-13-trans-prostenamide |
| 266 | 191 | n-butyl amine | N-n-butyl-9-oxo-18-thia-3,4,5,6,7-pentanor-13-trans-prostenamide |
| 267 | 203 | n-nonyl amine | N-n-nonyl-18-oxa-9-oxo-7a,10a-bis-homo-13-trans-prostenamide |
| 268 | 153 | isopropyl amine | N-isopropyl-9-oxo-6,7-dinor-13-trans-17-cis-prostadienamide |
| 269 | 178 | Δ$^3$-pyrrolidine | Δ$^3$-pyrrolidine amide of 20-chloro-9-oxo-5,6,7,17,18,19-hexanor-10a-homo-13-trans-prostenoic acid |
| 270 | 140 | pyrrolidine | pyrrolidine amide of 9-oxo-13-trans-prostenoic acid |
| 271 | 166 | piperidine | piperidine amide of 20-butyl-9-oxo-7a,7b-bis-homo-13-trans-prostenoic acid |
| 272 | 183 | Δ$^3$-piperidine | Δ$^3$-piperidine amide of 20-chloro-9-oxo-7-nor-10a-homo-13-trans-prostenoic acid |
| 273 | 174 | hexamethylenimine (homopiperidine) | hexamethylenimine amide of 9-oxo-5,6,7-trinor-10a-homo-13-trans-17-cis-prostadienoic acid |
| 274 | 140 | 3-azobicyclo[3,2,2]-nonane | 3-azabicyclo[3,2,2]-nonyl amide of 9-oxo-13-trans-prostenoic acid |
| 275 | 157 | 3-azaspiro-[5,5]nonane | 3-azaspiro[5,5]nonyl amide of 9-oxo-3,4,5,6,7-pentanor-13-trans-prostenoic acid |
| 276 | 192 | 4-phenyl-piperidine | 4'-phenylpiperidine amide of 9-oxo-18-thia-7a,7b-bis-homo-13-trans-prostenoic acid |
| 277 | 162 | diallyl amine | N,N-diallyl-9-oxo-5,6,7,18,19,20-hexanor-13-trans-prostenamide |
| 278 | 167 | allyl methylamine | N-allyl-N-methyl-15-methyl-9-oxo-7a,7b-bis-homo-17,18,19,20-tetranor-13-trans-prostenamide |
| 279 | 181 | dipropargyl amine | N,N-dipropargyl-9-oxo-20-propyl-7-nor-10a-homo-13-trans-prostenamide |
| 280 | 200 | cyclohexyl amine | N-cyclohexyl-18-oxa-9-oxo-13-trans-prostenamide |
| 281 | 169 | dicyclohexyl amine | N,N-dicyclohexyl-20-butyl-9-oxo-10a-homo-13-trans-prostenamide |
| 282 | 150 | aniline | N-phenyl-9-oxo-13-trans-17-cis-prostadienamide |
| 283 | 164 | N-methyl-aniline | N-methyl-N-phenyl-9-oxo-7a,7b-bis-homo-13-trans-prostenamide |
| 284 | 140 | m-trifluoromethyl-aniline | N-(m-trifluoromethylphenyl)-9-oxo-13-trans-prostenamide |
| 285 | 147 | p-dimethylamino-aniline | N-(p-dimethylaminophenyl)-17-methyl-9-oxo-19,20-dinor-13-trans-prostenamide |
| 286 | 165 | o-chloro-aniline | N-(o-chlorophenyl)-20-chloro-9-oxo-7a,7b-bis-homo-17,18,19-trinor-13-trans-prostenamide |

TABLE XV-continued

| Ex. | Starting Prostenoic Acid of Example | Amine | Prostenoic Acid Amide Product |
|---|---|---|---|
| 287 | 180 | m-toluidine | N-(m-methylphenyl)-9-oxo-7-nor-10a-homo-13-trans-prostenamide |
| 288 | 182 | benzyl amine | N-benzyl-17-methyl-9-oxo-7,19,20-trinor-10a-homo-13-trans-prostenamide |
| 289 | 195 | dibenzyl amine | N,N-dibenzyl-9-oxo-18-thia-7a,10a-bis-homo-13-trans-prostenamide |
| 290 | 140 | 3-amino-pyridine | N-(pyridyl-3)-9-oxo-13-trans-prostenamide |
| 291 | 151 | di(3-hydroxypropyl)amine | N,N-di(3-hydroxypropyl)-20-chloro-9-oxo-6,7-dinor-13-trans-prostenamide |
| 292 | 160 | 3-hydroxypropylamine | N-(3-hydroxypropyl)-9-oxo-5,6,7-trinor-13-trans-prostenamide |
| 293 | 140 | 2-hydroxyethyl amine | N-(2-hydroxyethyl)-9-oxo-13-trans-prostenamide |
| 294 | 161 | di(2-hydroxyethyl)amine | N,N-di(2-hydroxyethyl)-9-oxo-20-propyl-5,6,7-trinor-13-trans-prostenamide |
| 295 | 155 | 2-methoxyethyl amine | N-(2-methoxyethyl)-17-methyl-9-oxo-6,7,19,20-tetranor-13-trans-prostenamide |
| 296 | 203 | 2-amino-5-diethylamino pentane | N-(5-diethylaminopentyl-2)-18-oxa-9-oxo-7a,10a-bis-homo-13-trans-prostenamide |
| 297 | 139 | 1-(2-aminoethyl)piperidine | N-[2-(piperidyl-1)-ethyl]-20-butyl-9-oxo-13-trans-prostenamide |
| 298 | 141 | 1-(2-aminoethyl)pyrrolidine | N-[2-(pyrrolidinyl-1)ethyl]-9-oxo-6,7-dinor-13-trans-prostenamide |
| 299 | 150 | 1-(2-aminoethyl)morpholine | N-[2-(morpholinyl-1)-ethyl]-9-oxo-13-trans-17-cis-prostadienamide |
| 300 | 143 | 2-(2-aminoethyl)pyridine | N-[2-(pyridyl-2)-ethyl]-15-methyl-9-oxo-17,18,19-20-tetranor-13-trans-prostenamide |
| 301 | 140 | 2-dimethylaminoethyl amine | N-(2-dimethylaminoethyl)-9-oxo-13-trans-prostenamide |
| 302 | 154 | 2-di-n-butylaminoethyl amine | N-(2-di-n-butylaminoethyl)-20-chloro-9-oxo-6,7,17,18,19-pentanor-13-trans-prostenamide |
| 303 | 172 | 3-diethylaminopropyl amine | N-(3-diethylaminopropyl)-9-oxo-18,19,20-trinor-10a-homo-13-trans-prostenamide |
| 304 | 181 | methyl (2-dimethylaminoethyl)amine | N-methyl-N-(2-dimethylaminoethyl)-9-oxo-20-propyl-7-nor-10a-homo-13-trans-prostenamide |
| 305 | 195 | 1-(3-methylaminopropyl)piperidine | N-methyl-N-[3-(piperidyl-1)propyl]-9-oxo-18-thia-7a,10a-bis-homo-13-trans-prostenamide |
| 306 | 140 | 4-methyl-piperazine | 4-methylpiperazyl amide of 9-oxo-13-trans-prostenoic acid |
| 307 | 140 | 4-phenyl-piperazine | 4-phenylpiperazyl amide of 9-oxo-13-trans-prostenoic acid |
| 308 | 140 | 1-(2-aminoethyl)piperidine | N-[2-(1-piperidyl)-ethyl]-9-oxo-13-trans-prostenamide |
| 309 | 140 | methyl (2-dimethylaminoethyl)amine | N-methyl-N-(2-dimethylaminoethyl)-9-oxo-13-trans-prostenamide |
| 310 | 140 | 2-diethylaminoethyl amine | N-(2-diethylaminoethyl)-9-oxo-13-trans-prostenamide |
| 311 | 168 | 3-dimethylaminopropyl amine | N-(3-dimethylaminopropyl)-9-oxo-10a-homo-13-trans-prostenamide |
| 312 | 140 | 1-(2-aminoethyl)pyrrolidine | N-[2-(1-pyrrolidinyl)ethyl]-9-oxo-13-trans-prostenamide |
| 313 | 140 | 1-aminoadamantane | N-(adamantyl-1)-9-oxo-13-trans-prostenamide |
| 314 | 245 | dimethyl-amine | N,N-dimethyl-3-oxa-9-oxo-13-trans-prostenamide |
| 315 | 245 | 3-diethylaminopropyl amine | N-(3-diethylaminopropyl)-3-oxa-9-oxo-13-trans-prostenamide |
| 316 | 245 | 4-methyl-piperazine | 4-methylpiperazine amide of 3-oxa-9-oxo-13-trans-prostenoic acid |
| 317 | 244 | 4-methyl-piperazine | 4-methylpiperazine amide of 9-oxo-3-thia-13-trans-prostenoic acid |
| 318 | 243 | pyrrolidine | pyrrolidine amide of 9-oxo-3,3-dimethyl-13-trans-prostenoic acid |
| 319 | 243 | ammonia | 9-oxo-3,3-dimethyl-13-trans-prostenamide |
| 320 | 247 | propylamine | N-propyl-20-chloro-9-oxo-3,3-dimethyl-17,18,19-trinor-13-trans-prostenamide |
| 321 | 246 | 1-aminoadamantane | N-(1-adamantyl)-20-chloro-3,3-dimethyl-9-oxo-13-trans-prostenamide |
| 322 | 248 | 1-(2-aminoethyl)pyrrolidine | N-[2-(1-pyrrolidinyl)ethyl]-3,3-dimethyl-9-oxo-13-trans-17-cis-prostadienamide |
| 323 | 249 | Δ³-piperidine | Δ³-piperidine amide of 3,3,20-trimethyl-9-oxo-13-trans-prostenoic acid |
| 324 | 250 | n-octyl-amine | N-octyl-20-chloro-3-oxa-9-oxo-13-trans-prostenamide |
| 325 | 251 | di-isopropyl amine | N,N-diisopropyl-20-chloro-3-oxa-9-oxo-17,18,19-trinor-13-trans-prostenamide |
| 326 | 252 | 3-dimethylaminopropyl amine | N-(3-dimethylaminopropyl)-3-oxa-9-oxo-13-trans-17-cis-prostadienamide |
| 327 | 253 | ammonia | 20-methyl-3-oxa-9-oxo-13-trans-prostenamide |
| 328 | 254 | morpholine | morpholino amide of 20-chloro-9-oxo-3-thia-13-trans-prostenoic acid |
| 329 | 255 | methyl(2-dimethylaminoethyl)amine | N-methyl-N-(2-dimethylaminoethyl)-20-chloro-9-oxo-3-thia-17,18,19-trinor-13-trans-prostenamide |
| 330 | 256 | p-chloro-aniline | N-(p-chlorophenyl)-9-oxo-3-thia-13-trans-17-cis-prostadienamide |
| 331 | 257 | 3-amino-pyridine | N-(pyridyl-3)-9-oxo-3-thia-19,20-dinor-13-trans-prostenamide |
| 332 | 136 | ammonia | 2-ethyl-9-oxo-13- |

TABLE XV-continued

| Ex. | Starting Prostenoic Acid of Example | Amine | Prostenoic Acid Amide Product |
|---|---|---|---|
| 333 | 136 | 4-methyl-piperazine | trans-prostenamide 4-methylpiperazine amide of 2-ethyl-9-oxo-13-trans-prostenoic acid |
| 334 | 137 | 3-azabicyclo[3,2,2]-nonane | 3-azabicyclo[3,2,2]-nonyl amide of 2-ethyl-9-oxo-13-trans-17-cis-prostadienoic acid |
| 335 | 138 | dibenzyl amine | N,N-dibenzyl-2-ethyl-9-oxo-20-chloro-13-trans-prostenamide |
| 336 | 138 | methyl amine | N-methyl-2-ethyl-9-oxo-20-chloro-13-trans-prostenamide |
| 337 | 242 | 3-dimethylaminopropyl amine | N-(3-dimethylaminopropyl)-9-oxo-5-cis-13-trans-prostadienamide |
| 338 | 242 | 3-azaspiro[5,5]undecane (4,4-spirocyclohexylpiperidine | 4,4-spirocyclohexylpiperidine amide of 9-oxo-5-cis-13-trans-prostadienoic acid |
| 339 | 242 | di-n-propyl amine | N,N-di-n-propyl-9-oxo-5-cis-13-trans-prostadienamide |
| 340 | 242 | p-fluoro-aniline | N-(p-fluorophenyl)-9-oxo-5-cis-13-trans-prostadien-amide |
| 341 | 243 | 3-azabicyclo[3,2,2]-nonane | 3-azabicyclo[3,2,2]-nonyl amide of 9-oxo-3,3-dimethyl-13-trans-prostenoic acid |
| 342 | 244 | 3-azabicyclo[3,2,2]-nonane | 3-azabicyclo[3,2,2]-nonyl amide of 9-oxo-3-thia-13-trans-prostenoic acid |

EXAMPLES 343-366

By the procedure of Example 259, with the substitution of the appropriate hydrazine for 3-dimethylaminopropylamine, the prostenoic acids of Table XVI which follows, are converted to the corresponding hydrazide products of the Table.

TABLE XVI

| Ex. | Starting Prostenoic Acid of Example | Hydrazine Reagent | Product Prostenoic Acid Hydrazide |
|---|---|---|---|
| 343 | 140 | hydrazine | N-amino-9-oxo-13-trans-prostenamide |
| 344 | 140 | 1,1-dimethyl hydrazine | N-(dimethylamino)-9-oxo-13-trans-prostenamide |
| 345 | 140 | 1,1-diethyl hydrazine | N-(diethylamino)-9-oxo-13-trans-prostenamide |
| 346 | 161 | 1-amino-piperidine | N-(1-piperidyl)-9-oxo-20-propyl-5,6,7-trinor-13-trans-prostenamide |
| 347 | 185 | 1-amino-hexamethyleneimine | N-(1-hexamethyleneimino)-9-oxo-19,20-dinor-7a,10a-bis-homo-13-trans-prostenamide |
| 348 | 167 | 1-amino-morpholine | N-(1-morpholinyl)-15-methyl-9-oxo-7a,7b-bis-homo-17,18,19,-20-tetranor-13-trans-prostenamide |
| 349 | 140 | 1-amino-4-methylpiperazine | N-(4-methylpiperazino)-9-oxo-13-trans-prostenamide |
| 350 | 140 | phenylhydrazine | N-anilino-9-oxo-13-trans-prostenamide |
| 351 | 189 | hydrazine | N-amino-9-oxo-18-thia-13-trans-prostenamide |
| 352 | 203 | 1,1-dimethyl hydrazine | N-(dimethylamino)-18-oxa-9-oxo-7a,10a-bis-homo-13-trans-prostenamide |
| 353 | 242 | 1,1-diethyl hydrazine | N-(diethylamino)-9-oxo-5-cis-13-trans-prostadienamide |
| 354 | 242 | 1,1-diisopropyl hydrazine | N-(diisopropylamino)-9-oxo-5-cis-13-trans-prostadienamide |
| 355 | 242 | 1-amino-piperidine | N-(1-piperidyl)-9-oxo-5-cis-13-trans-prostadienamide |
| 356 | 243 | 1,1-dimethylhydrazino | N-(dimethylamino)-3,3-dimethyl-9-oxo-13-trans-prostenamide |
| 357 | 246 | hydrazine | N-amino-20-chloro-3,3-dimethyl-9-oxo-13-trans-prostenamide |
| 358 | 249 | phenylhydrazine | N-anilino-3,3,20-trimethyl-9-oxo-13-trans-prostenamide |
| 359 | 244 | 1-amino-hexamethyleneimino | N-(1-hexamethyleneimino)-9-oxo-3-thia-13-trans-prostenamide |
| 360 | 255 | 1,1-dibutylhydrazine | N-(di-n-butylamino)-20-chloro-9-oxo-3-thia-17,18,19-tri-nor-13-trans-prostenamide |
| 361 | 245 | 1,1-dimethylhydrazine | N-(dimethylamino)-3-oxa-9-oxo-13-trans-prostenamide |
| 362 | 252 | 1-amino-4-ethylpiperazine | N-(4-ethylpiperazino-1)-3-oxa-9-oxo-13-trans-17-cis-prostadienamide |
| 363 | 253 | 1-amino-piperidine | N-(piperidino-1)-20-methyl-3-oxa-9-oxo-13-trans-prostenamide |
| 364 | 136 | 1,1-dimethylhydrazine | N-(dimethylamine)-2-ethyl-9-oxo-13-trans-prostenamide |
| 365 | 138 | hydrazine | N-amino-20-chloro-2-ethyl-9-oxo-13-trans-prostenamide |
| 366 | 137 | 1,1-dimethylhydrazine | N-(dimethylamino)-2-ethyl-9-oxo-13-trans-17-cis-prostenamide |

EXAMPLE 367

Preparation of N-(3-dimethylaminopropyl)-9-(α- and β-)-hydroxy-13-trans-prostenamide To a stirred solution of 3 g. of N-(3-dimethylaminopropyl)-9-oxo-13-trans-prostenamide in 100 ml. of absolute alcohol is added 137 mg. of sodium borohydride. The resulting solution is stirred at ambient temperature for 72 hours, then poured into 300 ml. of saturated sodium chloride solution. The mixture is extracted several times with ether, and the combined extracts are washed to neutrality with saturated sodium chloride solution, dried with anhydrous magnesium sulfate, and taken to dryness to furnish 2.9 g. (97%) of N-(3-dimethylaminopropyl)-9-(α- and β-)-hydroxy-13-trans-prostenamide.

EXAMPLES 368-453

Reduction with sodium borohydride in ethanol of the appropriate keto-amides by the procedure of Example 367 is productive of the alcohol-amides obtained as mixtures of 9α- and 9β-epimers) of Table XVII, which follows.

TABLE XVII

| Example | Starting 9-Oxo-Prostenamide of Example | Product |
|---|---|---|
| 368 | 261 | N,N-dimethyl-9-hydroxy-13-trans-prostenamide |
| 369 | 262 | N,N-di-n-butyl-9-hydroxy-20-propyl-5,6,7-trinor-13-trans-prostenamide |
| 370 | 263 | N,N-di-n-octyl-9-hydroxy-18,19,20-trinor-13-trans-prostenamide |
| 371 | 264 | N,N-di-isobutyl-20-chloro-9-hydroxy-7a,10a-bis-homo-13-trans-prostenamide |
| 372 | 265 | N-methyl-9-hydroxy-13-trans-prostenamide |
| 373 | 266 | N-n-butyl-9-hydroxy-18-thia-3,4,5,6,7-pentanor-13-trans-prostenamide |
| 374 | 267 | N-n-nonyl-18-oxa-9-hydroxy-7a,10a-bis-homo-13-trans-prostenamide |
| 375 | 268 | N-isopropyl-9-hydroxy-6,7-dinor-13-trans-17-cis-prostadienamide |
| 376 | 269 | Δ³-pyrrolidine amide of 20-chloro-9-hydroxy-5,6,7,17,18,19-hexanor-10a-homo-13-trans-prostenoic acid |
| 377 | 270 | pyrrolidine amide of 9-hydroxy-13-trans-prostenoic acid |
| 378 | 271 | piperidine amide of 20-butyl-9-hydroxy-7a,7b-bis-homo-13-trans-prostenoic acid |
| 379 | 272 | Δ³piperidine amide of 20-chloro-9-hydroxy-7-nor-10a-homo-13-trans-prostenoic acid |
| 380 | 273 | hexamethylenimine amide of 9-hydroxy-5,6,7-trinor-10a-homo-13-trans-17-cis-prostadienoic acid |
| 381 | 274 | 3-azabicyclo[3,2,2]nonyl amide of 9-hydroxy-13-trans-prostenoic acid |
| 382 | 275 | 3-azaspiro[5,5]nonyl amide of 9-hydroxy-3,4,5,6,7-pentanor-13-trans-prostenoic acid |
| 383 | 276 | 4'-phenylpiperidine amide of 9-hydroxy-18-thia-7a,7b-bis-homo-13-trans-prostenoic acid |
| 384 | 277 | N,N-diallyl-9-hydroxy-5,6,7,18,19,20-hexanor-13-trans-prostenamide |
| 385 | 278 | N-allyl-N-methyl-15-methyl-9-hydroxy-7a,7b-bis-homo-17,18,19,20-tetranor-13-trans-prostenamide |
| 386 | 279 | N,N-dipropargyl-9-hydroxy-20-propyl-7-nor-10a-homo-13-trans-prostenamide |
| 387 | 280 | N-cyclohexyl-18-oxa-9-hydroxy-13-trans-prostenamide |
| 388 | 281 | N,N-dicyclohexyl-20-butyl-9-hydroxy-10a-homo-13-trans-prostenamide |
| 389 | 282 | N-phenyl-9-hydroxy-13-trans-17-cis-prostadienamide |
| 390 | 283 | N-methyl-N-phenyl-9-hydroxy-7a,7b-bis-homo-13-trans-prostenamide |
| 391 | 284 | N-(m-trifluoromethylphenyl)-9-hydroxy-13-trans-prostenamide |
| 392 | 285 | N-(p-dimethylaminophenyl)-17-methyl-9-hydroxy-19,20-dinor-13-trans-prostenamide |
| 393 | 286 | N-(o-chlorophenyl)-20-chloro-9-hydroxy-7a,7b-bis-homo-17,18,19-trinor-13-trans-prostenamide |
| 394 | 287 | N-(m-methylphenyl)-9-hydroxy-7-nor-10a-homo-13-trans-prostenamide |
| 395 | 288 | N-benzyl-17-methyl-9-hydroxy-7,19,20-trinor-10a-homo-13-trans-prostenamide |
| 396 | 289 | N,N-dibenzyl-9-hydroxy-18-thia-7a,10a-bis-homo-13-trans-prostenamide |
| 397 | 290 | N-(pyridyl-3)-9-hydroxy-13-trans-prostenamide |
| 398 | 291 | N,N-di(3-hydroxypropyl)-20-chloro-9-hydroxy-6,7-dinor-13-trans-prostenamide |
| 399 | 292 | N-(3-hydroxypropyl)-9-hydroxy-5,6,7-trinor-13-trans-prostenamide |
| 400 | 293 | N-(2-hydroxyethyl)-9-hydroxy-13-trans-prostenamide |
| 401 | 294 | N,N-di(2-hydroxyethyl)-9-hydroxy-20-propyl-5,6,7-trinor-13-trans-prostenamide |
| 402 | 295 | N-(2-methoxyethyl)-17-methyl-9-hydroxy-6,7,19,20-tetranor-13-trans-prostenamide |
| 403 | 296 | N-(5-diethylaminopentyl-2)-18-oxa-9-hydroxy-7a,10a-bis-homo-13-trans-prostenamide |
| 404 | 297 | N-[2-(piperidyl-1)ethyl]-20-butyl-9-hydroxy-13-trans-prostenamide |
| 405 | 298 | N-[2-(pyrrolidinyl-1)ethyl]-9-hydroxy-6,7-dinor-13-trans-prostenamide |
| 406 | 299 | N-[2-(morpholinyl-1)ethyl]-9-hydroxy-13-trans-17-cis-prostadienamide |
| 407 | 300 | N-[2-(pyridyl-2)ethyl]-15-methyl-9-hydroxy-17,18,19,20-tetranor-13-trans-prostenamide |
| 408 | 301 | N-(2-dimethylaminoethyl)-9-hydroxy-13-trans-prostenamide |
| 409 | 302 | N-(2-di-n-butylaminoethyl)-20-chloro-9-hydroxy-6,7,17,18,19-pentanor-13-trans-prostenamide |
| 410 | 303 | N-(3-diethylaminopropyl)-9-hydroxy-18,19,20-trinor-10a-homo-13-trans-prostenamide |
| 411 | 304 | N-methyl-N-(2-dimethylaminoethyl)-9-hydroxy-20-propyl-7-nor-10a-homo-13-trans-prostenamide |
| 412 | 305 | N-methyl-N-[3-(piperidyl-1)propyl]-9-hydroxy-18-thia-7a,10a-bis-homo-13-trans-prostenamide |
| 413 | 306 | 4-methylpiperazyl amide of 9-hydroxy-13-trans-prostenoic acid |
| 414 | 307 | 4-phenylpiperazyl amide of 9-hydroxy-13-trans-prostenoic acid |
| 415 | 308 | N-[2-(1-piperidyl)ethyl]-9-hydroxy-13-trans-prostenamide |
| 416 | 309 | N-methyl-N-(2-dimethylaminoethyl)-9-hydroxy-13-trans-prostenamide |
| 417 | 310 | N-(2-diethylaminoethyl)-9-hydroxy-13-trans-prostenamide |
| 418 | 259 | N-(3-dimethylaminopropyl)-9-hydroxy-10a-homo-13-trans-prostenamide |
| 419 | 312 | N-[2-(1-pyrrolidinyl)ethyl]-9-hydroxy-13-trans-prostenamide |
| 420 | 313 | N-(adamantyl-1)-9-hydroxy-13-trans-prostenamide |
| 421 | 314 | N,N-dimethyl-3-oxa-9-hydroxy-13-trans-prostenamide |
| 422 | 315 | N-(3-diethylaminopropyl)-3-oxa-9-hydroxy-13-trans-prostenamide |
| 423 | 316 | 4-methylpiperazine amide of 3-oxa-9-hydroxy-13-trans-prostenoic acid |
| 424 | 317 | 4-methylpiperazine amide of 9-hydroxy-3-thia-13-trans-prostenoic acid |
| 425 | 318 | pyrrolidine amide of 9-hydroxy-3,3-dimethyl-13-trans-prostenoic acid |
| 426 | 319 | 9-hydroxy-3,3-dimethyl-13-trans-prostenamide |
| 427 | 320 | N-propyl-20-chloro-9-hydroxy-3,3-dimethyl-17,18,19-trinor-13-trans-prostenamide |
| 428 | 321 | N-(1-adamantyl)-20-chloro-3,3-dimethyl-9-hydroxy-13-trans-prostenamide |
| 429 | 322 | N-[2-(1-pyrrolidinyl)ethyl]-3,3-dimethyl-9-hydroxy-13-trans-17-cis-prostadienamide |
| 430 | 323 | Δ³-piperidine amide of 3,3,20-trimethyl-9-hydroxy-13-trans-prostenoic acid |
| 431 | 324 | N-octyl-20-chloro-3-oxa-9-hydroxy-13-trans-prostenamide |
| 432 | 325 | N,N-diisopropyl-20-chloro-3-oxa-9-hydroxy-17,18,19-trinor-13-trans-prostenamide |
| 433 | 326 | N-(3-dimethylaminopropyl)-3-oxa-9-hydroxy-13-trans-17-cis-prostadienamide |
| 434 | 327 | 20-methyl-3-oxa-9-hydroxy-13-trans-prostenamide |
| 435 | 328 | morpholino amide of 20-chloro-9-hydroxy-3-thia-13-trans-prostenoic acid |
| 436 | 329 | N-methyl-N-(2-dimethylaminoethyl)-20-chloro-9-hydroxy-3-thia-17,18,19-trinor-13-trans-prostenamide |
| 437 | 330 | N-(p-chlorophenyl)-9-hydroxy-3-thia-13-trans-17-cis-prostadienamide |
| 438 | 331 | N-(pyridyl-3)-9-hydroxy-3-thia-19,20-dinor-13-trans-prostenamide |
| 439 | 332 | 2-ethyl-9-hydroxy-13-trans-prostenamide |
| 440 | 333 | 4-methylpiperazine amide of 2-ethyl-9-hydroxy-13-trans-prostenoic acid |
| 441 | 334 | 3-azabicyclo[3,2,2]nonyl amide of 2-ethyl-9-hydroxy-13-trans-17-cis-prostadienoic acid |
| 442 | 335 | N,N-dibenzyl-2-ethyl-9-hydroxy-20-chloro-13-trans-prostenamide |
| 443 | 336 | N-methyl-2-ethyl-9-hydroxy-20-chloro-13-trans-prostenamide |
| 444 | 337 | N-(3-dimethylaminopropyl)-9-hydroxy- |

TABLE XVII-continued

| Example | Starting 9-Oxo-Prostenamide of Example | Product |
|---|---|---|
| 445 | 338 | 5-cis-13-trans-prostadienamide 4,4-spirocyclohexylpiperidine amide of 9-hydroxy-5-cis-13-trans-prostadienoic acid |
| 446 | 339 | N,N-di-n-propyl-9-hydroxy-5-cis-13-trans-prostadienamide |
| 447 | 340 | N-(p-fluorophenyl)-9-hydroxy-5-cis-13-trans-prostadienamide |
| 448 | 341 | 3-azabicyclo[3,2,2]nonyl amide of 9-hydroxy-3,3-dimethyl-13-trans-prostenoic acid |
| 449 | 342 | 3-azabicyclo[3,2,2]nonyl amide of 9-hydroxy-3-thia-13-trans-prostenoic acid |
| 450 | 343 | N-amino-9-hydroxy-13-trans-prostenamide |
| 451 | 344 | N-(dimethylamino)-9-hydroxy-13-trans-prostenamide |
| 452 | 356 | N-(dimethylamino)-9-hydroxy-3,3-dimethyl-13-trans-prostenamide |
| 453 | 363 | N-(piperidino-1)-20-methyl-3-oxa-9-hydroxy-13-trans-prostenamide |

EXAMPLE 454

Preparation of 9-oxo-13-trans-prostenohydroxamic acid

A solution of 6.46 g. (0.02 mole) of 9-oxo-13-trans-prostenoic acid (Example 140), 2.02 g. (0.02 mole) triethylamine in 135 ml. of dry tetrahydrofuran is added dropwise to a stirred and cooled solution of 2.16 g. ethyl chloroformate in 25 ml. of tetrahydrofuran during 45 minutes. The reaction mixture is stirred for another 25 minutes and the precipitated triethyl ammonium chloride is filtered. A solution of hydroxylamine (prepared from 1.4 g. (0.02 mole) of hydroxylamine hydrochloride and 0.8 g. (0.02 mole) of sodium hydroxide) in methanol is then added to the filtrate and the resulting mixture is concentrated to about one-tenth its initial volume. The residue is diluted with ether and is filtered through celite (diatomaceous earth) and concentrated. The residue is purified by adsorption chromatography on silica gel to give 4.053 g. of a light yellow oil.

EXAMPLE 455

Preparation of 4,4'-bis(dimethylamino)-N-{7-[trans-2-(1-octenyl)-5-oxocyclopentyl)-heptanoyl}carbanilide A solution of 5.02 g. of 9-oxo-13-trans-prostenoic acid (Example 140) in 110 ml. of ether is added to 4.426 g. of bis-(p-dimethylaminophenyl)carbodiimide dissolved in 180 ml. of ether. The mixture is refluxed for four hours, and then the volume is reduced to 100 ml. by evaporation. After standing five hours at 25° C. and overnight at −10° C., the precipitated product is collected by vacuum filtration and dried to give 8.9 g. solid, m.p. 70°-85° C. The material is purified by chromatography on silica gel and recrystallization from methanol to give white crystals, m.p. 76°-85° C.

EXAMPLE 456

Preparation of 3'-pyridyl 9-oxo-13-trans-prostenoate

9-Oxo-13-trans-prostenoic acid is converted to 9-oxo-13-trans-prostenoyl chloride by treatment with thionyl chloride. A benzene solution of 9-oxo-13-trans-prostenoyl chloride (24.8 moles) is slowly added to a slight excess of 3-hydroxypyridine (26 moles) in 100 ml. of benzene containing 5 ml. of triethylamine. The mixture is magnetically stirred and refluxed for 30 min. The reaction mixture is filtered and taken to dryness and the residue is dissolved in ether and washed successively with saline, dilute sodium bicarbonate solution, dried and taken to dryness. The oil is purified by adsorption chromatography on a magnesia-silica gel column and eluted with benzene to give a dark yellow oil.

EXAMPLE 457

Preparation of 1-9-oxo-5-cis,13-trans-prostadienoic acid

To a solution of 8.9 gm. of 1-15-0-acetyl $PGA_2$ methyl ester [W. P. Schneider, R. D. Hamilton, L. E. Rhuland; J. Amer. Chem. Soc., 94 2122 (1972)] and 10.97 gm. of tripropylsilane is added 170 mg. tristriphenylrhodium chloride. The resulting solution is heated in a 90° C. oil bath for 6 hours, stirred in room temperature for 48 hours, and heated 2 more hours at 85° C. At this point an additional 50 mg. of tristriphenylrhodium chloride is added and the solution is heated 5 more hours.

The reaction mixture is cooled, diluted with 300 ml. of toluene and concentrated in vacuo to give 18 gm. of an oil. The oil is dissolved in 30 ml. of methanol, and after stirring 5 minutes the solution is concentrated in vacuo. The residue is partitioned between 30 ml. of nitromethane and 30 ml. of cyclohexane. The cyclohexane phase is extracted with 20 ml. additional nitromethane. The combined nitromethane extracts are concentrated in vacuo, and 50 ml. of benzene is added and removed in vacuo to give 3.9 gm. of an oil. The cyclohexane fraction is concentrated in vacuo to give 12.3 gm. of an oil.

11.3 gm. of the oil from the cyclohexane extraction is dissolved in 700 ml. of methanol, 6 ml. of 5% aqueous sodium bicarbonate is added and the solution is stirred four days. The solution is concentrated in vacuo and 100 ml. of ether is added. The ether solution is washed twice with 50 ml. of brine, dried and concentrated in vacuo to give 8.8 gm. of an oil. This oil is dissolved in 50 ml. of hexane and extracted 3 times with 20 ml. of nitromethane. The nitromethane is concentrated in vacuo to give 4 gm. of an oil, which is combined with the 3.9 gm. of oil from the initial nitromethane extract and the 7.9 gm. is chromatographed on a 48 inch by 3 inch flat diameter nylon tube packed with 1 kg. acid-washed silica-gel. The column is developed with 7% ethyl acetate-in-benzene. The fraction corresponding to $R_f$ 0.25 – 0.55 is removed and washed 4 times with 1 liter of ether. Concentration of the ether solution gives 6 gm. of 11-deoxy-15-0-acetyl $PGE_2$ methyl ester.

The fraction corresponding to $R_f$ 0.55 – 0.75 is removed and the material is eluted with 4,500 ml. ether washes. Concentration of the ether yields 1 methyl 9-oxo-5-cis,13-trans-prostadienoate; i.r.: 1730 cm$^{-1}$, 975 cm$^{-1}$; pmr:CDCl$_3$ δ (3.68, s, 3H, COOCH$_3$), (5.4, m, 4H, vinyl). GLC analysis of the product obtained after oxidative ozonolysis indicates the presence of hexanoic acid, thereby establishing the location of the trans = at $C_{13}-C_{14}$. Saponification of this ester by the procedure described in Example 178 provides 1-9-oxo-5-cis,13-trans-prostadienoic acid.

EXAMPLE 458

Preparation of 1-methoximino-2-(5-methanesulfonyloxypentyl)-2-cyclopentene

To a cold solution of 9.85 g. (0.05 mole) of 1-methoximino-2-(5-hydroxypentyl)-2-cyclopentene (Example 126) and 7.6 g. (0.075 mole) of triethylamine in 100 ml.

of methylene chloride at −10° C. is added 6.3 g. (0.055 mole) of methanesulfonyl chloride at a rate to maintain a temperature of −10° to 0° C. The mixture is then stirred for 15 minutes and then poured into ice water. The organic phase is washed with cold 10% hydrochloric acid, cold saturated sodium bicarbonate solution, and cold saturated brine, dried (MgSO$_4$), and evaporated to yield a solid, m.p. 78°-80° C.

EXAMPLE 459

Preparation of
1-methoxyimino-2-(6-fluoro-6,6-dicarbethoxyhexyl)-2-cyclopentene

To a solution of sodio diethyl fluoromalonate, prepared from 2.062 g. (0.0491 mole) of sodium hydride in mineral oil (57.2%), 40 ml. of dry N,N-dimethylformamide and 8.174 g. (0.0458 mole) of diethyl fluoromalonate, is added dropwise 11.32 g. (0.0413 mole) of 1-methoximino-2-(5-methylsulfonyloxypentyl)-2-cyclopentene (Example 458) in 60 ml. of N,N-dimethylformamide. The mixture is refluxed for 2 hours under a nitrogen atmosphere. The mixture is concentrated and partitioned between cold dilute hydrochloric acid and diethyl ether, and the organic phase is washed with saturated brine, dried (MgSO$_4$), and evaporated to yield 13.631 g. (92%) of a yellow oil.

EXAMPLE 460

Preparation of
1-methoximino-2-(6-fluoro,6,6-dicarboxyhexyl)-2-cyclopentene

A mixture of 13.631 g. of the diester of Example 459 and 16 g. of potassium hydroxide in 364 ml. of 1:1 aqueous methanol is refluxed for 5 hours, cooled, concentrated, and is partitioned between water and diethyl ether. The aqueous phase is acidified with hydrochloric acid, extracted with ether, and the organic phase is washed with saturated brine, dried (MgSO$_4$) and evaporated to yield a solid. The solid is crystallized from diethyl ether petroleum ether (30°-60° C.) to give 10 g. (90%) of white crystals, m.p. 143°-145° C. (—CO$_2$).

EXAMPLE 461

Preparation of
1-methoximino-2-(6-fluoro-6-carboxyhexyl)-2-cyclopentene

A solution of 10 g. of the diacid of Example 460 in 60 ml. of 2-methoxyethyl ether is refluxed for 7 hours, cooled, and evaporated to yield 8.5 g. (95%) of a tan solid. A sample is crystallized from diethyl ether-petroleum ether (30°-60° C.) to give white crystals, m.p. 98°-100° C.

EXAMPLE 462

Preparation of
2-(6-fluoro-6-carboxyhexyl)cyclopent-2-en-1-one

The acid methoxime (8.5 g.) from Example 461 is refluxed for 5 hours with 180 ml. of acetone and 64 ml. of 2N hydrochloric acid. The mixture is cooled, the solvent is evaporated, and the residue is partitioned between water and diethyl ether. The organic phase is washed with saturated brine, dried (MgSO$_4$) and evaporated to yield 7.4 g. (98%) of a light yellow oil.

EXAMPLE 463

Preparation of
2-(6-fluoro-6-carbethoxyhexyl)cyclopent-2-en-1-one

The acid ketone (7.4 g.) from Example 462 is Fisher esterified with 300 ml. of absolute ethanol and 400 mg. of p-toluenesulfonic acid for 18 hours, cooled, and the solvent is evaporated. The resulting oil is dissolved in ether, washed with dilute sodium bicarbonate solution, and saline, dried (MgSO$_4$) and evaporated to give 7.306 g. (86%) of a light yellow oil.

EXAMPLE 464

Preparation of
2-(6,6-dicarbethoxy-6-phenylhexyl)-1-methoximino-2-cyclopentene

Treatment of 1-methoximino-2-(5-methanesulfonyloxypentyl)-2-cyclopentene (Example 458) with sodio diethyl phenylmalonate by the procedure of Example 35 is productive of the subject compound.

EXAMPLE 465

Preparation of
2-(6,6-dicarboxy-6-phenylhexyl)-1-methoximino-2-cyclopentene

Alkaline hydrolysis of 2-(6,6-dicarbethoxy-6-phenylhexyl)-1-methoximino-2-cyclopentene (Example 464) by the procedure of Example 36 is productive of the subject diacid.

EXAMPLE 466

Preparation of
2-(6-carboxy-6-phenylhexyl)-1methoximino-2-cyclopentene

Decarboxylation of 2-(6,6-dicarboxy-6-phenylhexyl)-1-methoximino-2-cyclopentene (Example 465) by the procedure of Example 37 is productive of the subject compound.

EXAMPLE 467

Preparation of
2-(6-carboxy-6-phenylhexyl)-2-cyclopentene-1-one

Methoxime cleavage of 2-(6-carboxy-6-phenylhexyl)-1-methoxiimino-2-cyclopentene (Example 466) in the manner of Example 38 is productive of the subject ketone.

EXAMPLE 468

Preparation of
2-(6-carbethoxy-6-phenylhexyl)-2-cyclopenten-1-one

Fisher esterification of the carboxylic acid of Example 467 in the manner of Example 39 is productive of the subject keto-ester.

EXAMPLE 469

Preparation of 2-(6-carbethoxyheptyl)-2-cyclopenten-1-one

The subject compound is prepared from 2-(5-tosyloxypentyl)-2-cyclopentenone-1-methoxime (Example 127) by treatment with sodio dietyl methylmalonate (procedure of Example 128), followed by saponification (procedure of Example 129), decarboxylation (procedure of Example 130), methoxime cleavage (procedure of Example 131) and esterification (procedure of Example 132).

EXAMPLES 470 – 506

Treatment of the listed cyclopentenone with the alanate reagent prepared from diisobutylaliminum hydride, methyl lithium, and the 1-alkyne listed in Table XVIII below, all in the manner of Example 44, furnishes the product prostenoate esters of the Table.

EXAMPLES 507 – 543

In the manner described in Example 139 the listed prostenoate esters of Table XIX below are saponified to the corresponding product prostenoic acids of the table.

TABLE XVIII

| Example | Starting cyclopentenone of Example | Starting 1-alkyne | Product 9-oxo-13-trans-prostenoate |
|---|---|---|---|
| 470 | 463 | 1-octyne | ethyl 9-oxo-2-fluoro-13-trans-prostenoate |
| 471 | 463 | 1-pentyne | ethyl 9-oxo-2-fluoro-18,19,20-trinor-13-trans-prostenoate |
| 472 | 463 | 5-methyl-1-hexyne | ethyl 9-oxo-2-fluoro-17-methyl-19,20-dinor-13-trans-prostenoate |
| 473 | 468 | 1-octyne | ethyl 9-oxo-2-phenyl-13-trans-prostenoate |
| 474 | 468 | 1-pentyne | ethyl 9-oxo-2-phenyl-18,19,20-trinor-13-trans-prostenoate |
| 475 | 468 | 5-chloro-1-pentyne | ethyl 9-oxo-2-phenyl-17-chloro-18,19,20-trinor-13-trans-prostenoate |
| 476 | 468 | 5-methyl-1-hexyne | ethyl 9-oxo-2-phenyl-17-methyl-19,20-dinor-13-trans-prostenoate |
| 477 | 468 | cis-5-octen-1-yne | ethyl 9-oxo-2-phenyl-13-trans,17-cis-prostadienoate |
| 478 | 469 | cis-5-octen-1-yne | ethyl 9-oxo-2-methyl-13-trans,17-cis-prostadienoate |
| 479 | 469 | 1-octyne | ethyl 9-oxo-2-methyl-13-trans-prostenoate |
| 480 | 469 | 1-pentyne | ethyl 9-oxo-2-methyl-18,19,20-trinor-13-trans-prostenoate |
| 481 | 469 | 5-methyl-1-hexyne | ethyl 9-oxo-2-methyl-17-methyl-19,20-dinor-13-trans-prostenoate |
| 482 | 469 | 5-chloro-1-pentyne | ethyl 9-oxo-2-methyl-17-chloro-18,19,20-trinor-13-trans-prostenoate |
| 483 | 132 | 1-pentyne | ethyl 9-oxo-2-ethyl-18,19,20-trinor-13-trans-prostenoate |
| 484 | 132 | 5-methyl-1-hexyne | ethyl 9-oxo-2-ethyl-17-methyl-19,20-dinor-13-trans-prostenoate |
| 485 | 214 | 1-pentyne | ethyl 9-oxo-3,3-dimethyl-18,19,20-trinor-13-trans-prostenoate |
| 486 | 214 | 5-methyl-1-hexyne | ethyl 9-oxo-3,3,17-trimethyl-19,20-dinor-13-trans-prostenoate |
| 487 | 219 | 1-pentyne | ethyl 9-oxo-3-oxa-18,19,20-trinor-13-trans-prostenoate |
| 488 | 219 | 5-methyl-1-hexyne | ethyl 9-oxo-3-oxa-17-methyl-19,20-dinor-13-trans-prostenoate |
| 489 | 223 | 5-methyl-1-hexyne | ethyl 9-oxo-3-thia-17-methyl-19,20-dinor-13-trans-prostenoate |
| 490 | 223 | 1-pentyne | ethyl 9-oxo-3-thia-18,19,20-trinor-13-trans-prostenoate |
| 491 | 28 | 4-phenyl-1-butyne | ethyl 9-oxo-16-phenyl-17,18,19,20-tetranor-13-trans-prostenoate |
| 492 | 28 | 3-cyclohexyl-1-propyne | ethyl 9-oxo-16,20-methano-13-trans-prostenoate |
| 493 | 219 | 4-phenyl-1-butyne | ethyl 9-oxo-3-oxa-16-phenyl-17,18,19,20-tetranor-13-trans-prostenoate |
| 494 | 223 | 4-phenyl-1-butyne | ethyl 9-oxo-3-thia-16-phenyl-17,18,19,20-tetranor-13-trans-prostenoate |
| 495 | 214 | 4-phenyl-1-butyne | ethyl 9-oxo-3,3-dimethyl-16-phenyl-17,18,19,20-tetranor-13-trans-prostenoate |
| 496 | 468 | 4-phenyl-1-butyne | ethyl 9-oxo-2,16-diphenyl-17,18,19,20-tetranor-13-trans-prostenoate |
| 497 | 469 | 4-phenyl-1-butyne | ethyl 9-oxo-2-methyl-16-phenyl-17,18,19,20-tetranor-13-trans-prostenoate |
| 498 | 219 | 3-cyclohexyl-1-propyne | ethyl 9-oxo-3-oxa-16,20-methano-13-trans-prostenoate |
| 499 | 223 | 3-cyclohexyl-1-propyne | ethyl 9-oxo-3-thia-16,20-methano-13-trans-prostenoate |
| 500 | 214 | 3-cyclohexyl-1-propyne | ethyl 9-oxo-3,3-dimethyl-16,20-methano-13-trans-prostenoate |
| 501 | 468 | 3-cyclohexyl-1-propyne | ethyl 9-oxo-2-phenyl-16,20-methano-13-trans-prostenoate |
| 502 | 469 | 3-cyclohexyl-1-propyne | ethyl 9-oxo-2-methyl-16,20-methano-13-trans-prostenoate |
| 503 | 132 | 3-cyclohexyl-1-propyne | ethyl 9-oxo-2-ethyl-16,20-methano-13-trans-prostenoate |
| 504 | 28 | 3-cyclopentyl-1-propyne | ethyl 9-oxo-16,19-methano-20-nor-13-trans-prostenoate |
| 505 | 28 | 3-cycloheptyl-1-propyne | ethyl 9-oxo-16,20-ethano-13-trans-prostenoate |
| 506 | 28 | 5-phenyl-1-pentyne | ethyl 9-oxo-17-phenyl-18,19,20-trinor-13-trans-prostenoate |

TABLE XIX

| Example | Starting alkyl prostenoate ester of Example | Product prostenoic acid |
|---|---|---|
| 507 | 470 | 9-oxo-2-fluoro-13-trans-prostenoic acid |
| 508 | 471 | 9-oxo-2-fluoro-18,19,20-trinor-13-trans-prostenoic |

TABLE XIX-continued

| Example | Starting alkyl prostenoate ester of Example | Product prostenoic acid |
|---|---|---|
| 509 | 472 | 9-oxo-2-fluoro-17-methyl-19,20-dinor-13-trans-prostenoic acid |
| 510 | 473 | 9-oxo-2-phenyl-13-trans-prostenoic acid |
| 511 | 474 | 9-oxo-2-phenyl-18,19,20-trinor-13-trans-prostenoic acid |
| 512 | 475 | 9-oxo-2-phenyl-17-chloro-18,19,20-trinor-13-trans-prostenoic acid |
| 513 | 476 | 9-oxo-2-phenyl-17-methyl-19,20-dinor-13-trans-prostenoic acid |
| 514 | 477 | 9-oxo-2-phenyl-13-trans,17-cis-prostadienoic acid |
| 515 | 478 | 9-oxo-2-methyl-13-trans,17-cis-prostadienoic acid |
| 516 | 479 | 9-oxo-2-methyl-13-trans-prostenoic acid |
| 517 | 480 | 9-oxo-2-methyl-18,19,20-trinor-13-trans-prostenoic acid |
| 518 | 481 | 9-oxo-2-methyl-17-methyl-19,20-dinor-13-trans-prostenoic acid |
| 519 | 482 | 9-oxo-2-methyl-17-chloro-18,19,20-trinor-13-trans-prostenoic acid |
| 520 | 483 | 9-oxo-2-ethyl-18,19,20-trinor-13-trans-prostenoic acid |
| 521 | 484 | 9-oxo-2-ethyl-17-methyl-19,20-dinor-13-trans-prostenoic acid |
| 522 | 485 | 9-oxo-3,3-dimethyl-18,19,20-trinor-13-trans-prostenoic acid |
| 523 | 486 | 9-oxo-3,3,17-trimethyl-19,20-dinor-13-trans-prostenoic acid |
| 524 | 487 | 9-oxo-3-oxa-18,19,20-trinor-13-trans-prostenoic acid |
| 525 | 488 | 9-oxo-3-oxa-17-methyl-19,20-dinor-13-trans-prostenoic acid |
| 526 | 489 | 9-oxo-3-thia-17-methyl-19,20-dinor-13-trans-prostenoic acid |
| 527 | 490 | 9-oxo-3-thia-18,19,20-trinor-13-trans-prostenoic acid |
| 528 | 491 | 9-oxo-16-phenyl-17,18,19,20-tetranor-13-trans-prostenoic acid |
| 529 | 492 | 9-oxo-16,20-methano-13-trans-prostenoic acid |
| 530 | 493 | 9-oxo-3-oxa-16-phenyl-17,18,19,20-tetranor-13-trans-prostenoic acid |
| 531 | 494 | 9-oxo-3-thia-16-phenyl-17,18,19,20-tetranor-13-trans-prostenoic acid |
| 532 | 495 | 9-oxo-3,3-dimethyl-16-phenyl-17,18,19,20-tetranor-13-trans-prostenoic acid |
| 533 | 496 | 9-oxo-2,16-diphenyl-17,18,19,20-tetranor-13-trans-prostenoic acid |
| 534 | 497 | 9-oxo-2-methyl-16-phenyl-17,18,19,20-tetranor-13-trans-prostenoic acid |
| 535 | 498 | 9-oxo-3-oxa-16,20-methano-13-trans-prostenoic acid |
| 536 | 499 | 9-oxo-3-thia-16,20-methano-13-trans-prostenoic acid |
| 537 | 500 | 9-oxo-3,3-dimethyl-16,20-methano-13-trans-prostenoic acid |
| 538 | 501 | 9-oxo-2-phenyl-16,20-methano-13-trans-prostenoic acid |
| 539 | 502 | 9-oxo-2-methyl-16,20-methano-13-trans-prostenoic acid |
| 540 | 503 | 9-oxo-2-ethyl-16,20-methano-13-trans-prostenoic acid |
| 541 | 504 | 9-oxo-16,19-methano-20-nor-13-trans-prostenoic acid |
| 542 | 505 | 9-oxo-16,20-ethano-13-trans-prostenoic acid |
| 543 | 506 | 9-oxo-17-phenyl-18,19,20-trinor-13-trans-prostenoic acid |

EXAMPLE 544

Preparation of 9α-hydroxy-13-trans-prostenoic acid

To a solution of 1 g. of 9-oxo-13-trans-prostenoic acid (Example 140) in 5 ml. of terahydrofuran, cooled in an ice bath, is added, in an atmosphere of nitrogen, 9 ml. of a 0.76 molar solution of lithium perhydro-9b-bora-phenalylhydride [Brown et al., J.A.C.S, 92, 709 (1970)] in tetahydrofuran. After 40 minutes at 0° C., the reaction mixture is treated with 3.6 ml. of 3N sodium hydroxide followed by 3.6 ml. of 30% hydrogen peroxide. After the addition of 50 ml. of ether, the solution is acidified with 2N hydrochloric acid. The ether phase is washed with saturated NaCl solution, dried with anhydrous MgSO$_4$ and taken to dryness. The material is chromatographed on 50 g. of silica gel. The column is washed with 250 ml. portions of 5% ether-in-benzene, 10% ether-in-benzene, and 15% ether-in-benzene; thsese washings are discarded. Elution with 800 ml. of 20% ether-in-benzene, followed by evaporation of the eluate, gives 665 mg. of product as a viscous oil. This material shows one spot on tlc; nmr (COCL$_3$) δ 6.14 (S, 2, —OH and —COOH), 5.40 (m, 2, trans —CH=λ CH—), 4.26, 3.90 (m, 1, epimerc > CHOH, 95% trans. 5% cis), 2.35 (t, 2, —CH$_2$COOH), 0.90 (distorted t, 3, terminal —CH$_3$).

EXAMPLE 545

Preparation of dl-9α-hydroxy-13-trans-prostenoic acid and dl-9β-hydroxy-8-epi-13-trans-prostenoic acid To a stirred, −78° C., solution of 1M lithium tri(sec-butyl)borohydride, 92.5 ml. (2.2 molar equivalents), in pentane: tetrahydrofuran (1:1) under nitrogen is added dropwise a solution of 12.58 g. (0.0391 mol) of dl-9-oxo-13-trans-prostenoic acid (Example 140), in 20 ml. of tetrahydrofuran. The reaction mixture is allowed to stir at −78° C. for 40 minutes and then 52 ml. of 2.5N sodium hydroxide is added followed by dropwise addition of 52 ml. of 30% hydrogen peroxide. The dry-ice bath is removed and reaction is allowed to come to room temperature. Diethyl ether (150 ml.) is added and the reaction mixture is acidified with 10% aqueous hydrochloric acid. The organic phase is separated and the aqueous phase re-extracted with ether. The combined ether extract is washed with saline, dried over magnesium sulfate and evaporated to give 13.68 g. of a light yellow oil. The crude material is submitted to dry column chromatography * using 900 g. of Woelm silica gel and is developed with cyclohexane-ethyl acetate-acetic acid (60:40:2) to yield 9.3 (74%) of an oil, which can be crystallize from hexane to give dl-9α-hydroxy-13-trans-prostenoic acid as white crystals, m.p. 48°–49° C.

* B. Loev and K. M. Snader, Chem. Ind., 15–16 (1965); progress in Separation and Purification, Vol. 3, p. 73–95, Wiley-Interscience (1970).

The dl-9β-hydroxy-8-epi-13-trans-prostenoic acid is isolated from the above dry column chromatography as an oil and crystallized from hexane to give 318 mg. (2.5%) of white crystals, m.p. 27°–28° C.

Dry column chromatography is performed in the following manner. The crude reaction mixture is dissolved in a minimum amount of dichloromethane and is placed atop 900 g. of Woelm silica gel (activity III) packed in a 87 × 2 inch (flat diameter) nylon tube. The column is developed with one column length volume of cyclohexane-ethyl acetate-acetic acid (60:40:2) and is then divided into 1 inch segments. The segments are washed with 25 ml. of ether and tlc 8 silica gel, solvent system:cyclohexane;ethyl acetate:acetic acid (60:40: 2) 3% cupric acetate in 9% phosphoric acid] of the segments is used to locate the products. The segments containing the products are combined and the products are extracted from the silica gel with diethyl ether are then isolated on evaporation of solvent.

dl-9α-Hydroxy-13-trans-prostenoic acid is found along the column at $R_f$ 0.35 – 0.56 and the dl-9β-hydroxy-8-epi-13-trans-prostenoic acid at $R_f$ 0.65 – 0.67.

Examples 546 – 579

Reduction of the 9-oxo-prostenoic acids listed in Table XX below with lithium (tri-sec-butyl)borohydride in the manner described in Example 545 provides the product 9α-hydroxy-prostenoic acids of the table. In addition there is also obtained a lesser amount of the corresponding 9β-hyroxy-8-epi-13-trans-prostenoic acid, separated from the major product by chromatography.

TABLE XX

| Example | Starting 9-oxo-prostenoic acid of Example | Product 9α-hydroxy-13-trans-prostenoic acid |
|---|---|---|
| 546 | 507 | 9α-hydroxy-2-fluoro-13-trans-prostenoic acid |
| 547 | 508 | 9α-hydroxy-2-fluoro-18,19,20-trinor-13-trans-prostenoic acid |
| 548 | 509 | 9α-hydroxy-2-fluoro-17-methyl-19,20-dinor-13-trans-prostenoic acid |
| 549 | 510 | 9α-hydroxy-2-phenyl-13-trans-prostenoic acid |
| 550 | 511 | 9α-hydroxy-2-phenyl-18,19,20-trinor-13-trans-prostenoic acid |
| 551 | 512 | 9α-hydroxy-2-phenyl-17-chloro-18,19,20-trinor-13-trans-prostenoic acid |
| 552 | 513 | 9α-hydroxy-2-phenyl-17-methyl-19,20-dinor-13-trans-prostenoic acid |
| 553 | 514 | 9α-hydroxy-2-phenyl-13-trans,17-cis-prostadienoic acid |
| 554 | 515 | 9α-hydroxy-2-methyl-13-trans,17-cis-prostadienoic acid |
| 555 | 516 | 9α-hydroxy-2-methyl-13-trans-prostenoic acid |
| 556 | 517 | 9α-hydroxy-2-methyl-18,19,20-trinor-13-trans-prostenoic acid |
| 557 | 518 | 9α-hydroxy-2-methyl-17-methyl-19,20-dinor-13-trans-prostenoic acid |
| 558 | 519 | 9α-hydroxy-2-methyl-17-chloro-18,19,20-trinor-13-trans-prostenoic acid |
| 559 | 520 | 9α-hydroxy-2-ethyl-18,19,20-trinor-13-trans-prostenoic acid |
| 560 | 521 | 9α-hydroxy-2-ethyl-17-methyl-19,20-dinor-13-trans-prostenoic acid |
| 561 | 522 | 9α-hydroxy-3,3-dimethyl-18,19,20-trinor-13-trans-prostenoic acid |
| 562 | 523 | 9α-hydroxy-3,3,17-trimethyl-19,20-dinor-13-trans-prostenoic acid |
| 563 | 524 | 9α-hydroxy-3-oxa-18,19,20-trinor-13-trans-prostenoic acid |
| 564 | 525 | 9α-hydroxy-3-oxa-17-methyl-19,20-dinor-13-trans-prostenoic acid |
| 565 | 526 | 9α-hydroxy-3-thia-17-methyl-19,20-dinor-13-trans-prostenoic acid |
| 566 | 527 | 9α-hydroxy-3-thia-18,19,20-trinor-13-trans-prostenoic acid |
| 567 | 528 | 9α-hydroxy-16-phenyl-17,18,19,20-tetranor-13-trans-prostenoic acid |
| 568 | 529 | 9α-hydroxy-16,20-methano-13-trans-prostenoic acid |
| 569 | 530 | 9α-hydroxy-3-oxa-16-phenyl-17,18,19,20-tetranor-13-trans-prostenoic acid |
| 570 | 531 | 9α-hydroxy-3-thia-16-phenyl-17,18,19,20-tetranor-13-trans-prostenoic acid |
| 571 | 532 | 9α-hydroxy-3,3-dimethyl-16-phenyl-17,18,19,20-tetranor-13-trans-prostenoic acid |
| 572 | 533 | 9α-hydroxy-2,16-diphenyl-17,18,19,20-tetranor-13-trans-prostenoic acid |
| 573 | 534 | 9α-hydroxy-2-methyl-16-phenyl-17,18,19,20-tetranor-13-trans-prostenoic acid |
| 574 | 535 | 9α-hydroxy-3-oxa-16,20-methano-13-trans-prostenoic acid |
| 575 | 536 | 9α-hydroxy-3-thia-16,20-methano-13-trans-prostenoic acid |
| 576 | 537 | 9α-hydroxy-3,3-dimethyl-16,20-methano-13-trans- |

TABLE XX-continued

| Example | Starting 9-oxo-prostenoic acid of Example | Product 9α-hydroxy-13-trans-prostenoic acid |
| --- | --- | --- |
| 577 | 538 | prostenoic acid<br>9α-hydroxy-2-phenyl-16,20-methano-13-trans-prostenoic acid |
| 578 | 539 | 9α-hydroxy-2-methyl-16,20-methano-13-trans-prostenoic acid |
| 579 | 540 | 9α-hydroxy-2-ethyl-16,20-methano-13-trans-prostenoic acid |

EXAMPLE 580

Ethyl 10-hydroxymethylene-9-oxo-13-trans-prostenoate

A mixture of 25 g. of ethyl 9-oxo-13-trans-prostenoate (Example 44), 25 g. of sodim hydride oil dispersion (57%), 29 ml. of ethyl formate, and 500 ml. of anhydrous benzene is stirred under nitrogen for 18 hours. Excess sodium hydride is destroyed by the addition of methanol. The mixture is extracted three times with water. The combined extracts are acidified with 4N hydrochloric acid. The oil which separates is extracted with ether, and the ether extract is washed several times with saturated sodium chloride solution, dried with anhydrous magnesium sulfate and taken to dryness to give 26.3 g. (97%) of product. The material gives a positive enol test with alcoholic ferric chloride solution.

EXAMPLE 581

Ethyl 10-cyano-9-oxo-13-trans-prostenoate

A solution of 3 g. of ethyl 10-hydroxymethylene-9-oxo-13-trans-prostenoate (Example 580) in 100 ml. of anhydrous benzene containing 1.79 g. of O,N-bis(trifluoroacetyl)hydroxylamine and 0.63 ml. of reagent pyridine is refluxed for 2 hours, and then kept at ambient temperature for 18 hours. The solution is taken to dryness. The residue is dissolved in ether and the resulting solution is washed with ice cold 1% potassium hydroxide, saturated sodium chloride solution, dried with anhydrous magnesium sulfate and taken to dryness to give 1.3 g. of product as an oil.

EXAMPLE 582

Ethyl 9-oxo-10-phenyl-13-trans-prostenoate

To a solution prepared by the interaction of 181 mg. of potassium with 50 ml. of anhydro-t-butanol is added 2 g. of ethyl 10-hydroxymethylene-9-oxo-13-trans-prostenoate (Example 580), followed by the addition of 1.41 g. of diphenyliodonium chloride. The resulting suspension is stirred at the reflux temperature for 24 hours. The solvent is partially removed and the reaction mixture is diluted with water and acidified with concentrated hydrochloric acid. The solution is extracted several times with ether. The sombined extracts are washed with saturated sodium chloride solution, dried with anhydrous magnesium sulfate and taken to dryness. The residue is dissolved in 50 ml. of methanol and the solution is treated with 3 ml. of 1N methanolic sodium methoxide at the reflux temperature in an atmosphere of nitrogen for 1 hour. The cooled solution is acidified with glacial acetic acid, flooded with water and the resulting mixture is extracted several times with ether. The combined extracts are washed with saturated sodium chloride solution, dried with anhydrous magnesium sulfate and taken to dryness to give 2.1 g. of product as an oil.

EXAMPLE 583

Ethyl 10-ethoxalyl-9-oxo-13-trans-prostenoate

To a solution of 1.72 g. of sodium in 260 ml. of absolute ethanol, under nitrogen atmosphere, is added, with ice bath cooling, 11 g. of freshly distilled diethyloxalate in one portion. To the resulting solution is added dropwise at a fast rate, 25 g. of ethyl 9-oxo-13-trans-prostenoate (Example 44). The solution is stirred at 0° C. for an additional 15 minutes, then at ambient temperature for 18 hours. The solution is poured into 800 ml. of water and the resulting solution is extracted with ether. The aqueous phase is acidified with 4N hydrochloric acid and extracted several times with ether. The combined extracts are washed with saturated sodium chloride solution, dried with anhydrous magnesium sulfate and taken to dryness to give 28.8 g. (90%) of product as an oil.

EXAMPLE 584

Ethyl 10-methyl-9-oxo-13-trans-prostenoate

A mixture of 3 g. of ethyl 10-ethoxalyl-9-oxo-13-trans-prostenoate (Example 583) and 2 g. of anhydrous potassium carbonate in 60 ml. of acetone containing 5 ml. of methyl iodide is stirred at ambient temperature in a stoppered flask for 11 days. The solids are filtered. The mother liquor is taken to dryness and the residual oil is dissolved in ether. The solution is washed several times with ice cold 1N potassium hydroxide solution, dried with anhydrous magnesium sulfate and taken to dryness to afford 2.53 g. of product as an oil.

EXAMPLE 585

Ethyl 10-methylthio-9-oxo-13-trans-prostenoate

A solution of 2 g. of ethyl 10-ethoxalyl-9-oxo-13-trans-prostenoate (Example 583) in 25 ml. of glyme is added to a suspension of 196 mg. of sodium hydride (60% dispersion in oil). After about 30 minutes there is added 900 mg. of methyl p-toluenethiosulfonate. The solution is stirred at the reflux temperature under nitrogen atmosphere for 18 hours. The filtered solution is taken to dryness. The residue is dissolved in ether and the solution is washed with 1% potassium hydroxide solution, saturated sodium chloride solution, dried with anhydrous magnesium sulfate and taken to dryness to give 1.5 g. of product as an oil.

EXAMPLE 586

Ethyl 10-benzoyloxy-9-oxo-13-trans-prostenoate

To a stirred suspension of 196 mg. of sodium hydride (60% dispersion in oil) in 35 ml. of anhydrous benzene is added a solution of 2 g. of ethyl 10-ethoxalyl-9-oxo-13-trans-prostenoate (Example 583) in 35 ml. of benzene. After about 30 minutes there is added at 0° C., a solution of 1.075 g. of dibenzoylperoxide in 10 ml. of benzene. The solution is allowed to stir at ambient temperature for 7 days. The solution is washed with ice cold 1% potassium hydroxide solution, saturated sodium chloride solution, dried with anhydrous magnesium sulfate and taken to dryness to give 1.33 g. of oil. The oil is chromatographed on 30 g. of silica gel. The column is washed with 200 ml. of benzene, 100 ml. of 10% ether-in-benzene, 100 ml. of 50% ether-in-benzene. These washings are discarded. Elution with 200 ml. of ether affords 802 mg. of product as an oil.

EXAMPLE 587

Ethyl 9-pyrrolidyl-9,13-trans-prostadienoate

A solution of 6 g. of ethyl 9-oxo-13-trans-prostenoate (Example 44) in 125 ml. of anhydrous benzene containing 20 mg. of p-toluenesulfonic acid and 2.2 ml. of pyrrolidine is stirred at the reflux temperature for 18 hours. Water is collected by a Dean -Stark apparatus. The solution is taken to dryness, dissolved in ether and filtered for clarification. Evaporation of the solvent affords 5.6 g. of product as an oil.

EXAMPLE 588

Ethyl 10-fluoro-9-oxo-13-trans-prostenoate

Perchloryl fluoride is bubbled into a solution of 3 g. ethyl 9-pyrrolidyl-10,13-trans-prostadienoate (Example 587) in 400 ml. of anhydrous benzene at a fast rate for a period of 4 minutes. The solution is flushed with nitrogen, washed with saturated sodium bicarbonate solution, saturated sodium chloride solution, dried with anhydrous magnesium sulfate and taken to dryness to afford 2.6 g. of product as an oil.

EXAMPLE 589

Ethyl 9-methylene-13-trans-prostenoate

Sodium hydride (830 mg. as 57% oil dispersion) in a 300 ml. 2-necked flask is washed several times with hexane to remove mineral oil. The flask is equipped with a rubber stopple and reflux condenser. Dimethyl sulfoxide (20 ml.) is introduced by means of a syringe and the mixture is stirred in an nitrogen atmosphere at 75°-80° C. for 45 minutes. The resulting solution is cooled in an ice water bath and 7.09 g. of methyltriphenylphosphonium bromide in 10 ml. of hot dimethylsulfoxide is introduced. The resulting brown colored solution is stirred at room temperature for 10 minutes and then there is added 6 g. of ethyl 9-oxo-13-trans-prostenoate (Example 44). The red colored reaction solution is stirred at ambient temperature for 20 hours. The solution is poured into 150 ml. of water. An equal volume of hexane is added and the mixture is filtered from precipitated salts. The hexane layer is separated and the aqueous phase is extracted several times with hexane. The combined hexane extracts are washed with saturated sodium chloride solution, dried with anhydrous magnesium sulfate and taken to dryness to give 3 g. of oily material. Vapor phase chromatography showes the material to contain unreacted ethyl 9-oxo-13-trans-prostenoate which is removed in the following manner. The oily material is allowed to react with 1 g. of semicarbazide hydrochloride and 2 g. of anhydrous sodium acetate in 30 ml. of ethanol containing 7 ml. of water at 100° C. for 10 minutes, then at ambient temperature for 2 hours. The resulting solution is flooded with water and extracted several times with ether. The combined ether extracts are washed with water, dried with anhydrous magnesium sulfate and taken to dryness to afford 3 g. of oily material, which is chromatographed on 90 g. of silica gel. The column is washed with 600 ml. of benzene and this eluate is taken to dryness to give 1.22 g. of product as an oil.

EXAMPLE 590

9-Methylene-13-trans-prostenoic acid

A suspension of 1.2 g. of ethyl 9-methylene-13-trans-prostenoate (Example 533) in 16 ml. of 50% aqueous methanol containing (445 mg. of potassium hydroxide is stirred at 50° C. for 4 hours, then at ambient temperature for 18 hours. The resulting solution is acidified with 3N hydrochloric acid and extracted several times with ether. The combined ether extracts are washed with saturated sodium chloride solution, dried with anhydrous magnesium sulfate and taken to dryness to give 950 mg. (84%) of product as an oil.

EXAMPLES 590A-590E

Saponification of the prostenoate esters listed in Table XXI below with an equimolar amount of potassium hydroxide by the procedure described in Example 590.

TABLE XXI

| Example | Starting alkyl prostenoate of Example | Product prostenoic acid |
|---|---|---|
| 590A | 581 | 9-oxo-10-cyano-13-trans-prostenoic acid |
| 590B | 582 | 9-oxo-10-phenyl-13-trans-prostenoic acid |
| 590C | 584 | 9-oxo-10-methyl-13-trans-prostenoic acid |
| 590D | 585 | 9-oxo-10-methylthio-13-trans-prostenoic acid |
| 590E | 588 | 9-oxo-10-fluoro-13-trans-prostenoic acid |

EXAMPLE 591

Ethyl 9-hydroxy-9-methyl-13-trans-prostenoate

To a Grignard solution prepared from 250 mg. of magnesium and 0.7 ml. of methyl iodide in 15 ml. of ether under nitrogen atmosphere is added dropwise a solution of 3 g. of ethyl 9-oxo-13-trans-prostenoate (Example 44) in 15 ml. of ether, and the resulting pasty solution is stirred for 18 hours. The ethereal layer is washed successively with saturated ammonium chloride solution and water, dried with anhydrous magnesium sulfate and taken to dryness to give 2.9 g. of oily material. Vapor phase chromatography indicated the presence of unreacted starting material. This material was pooled with similar material from other experiments for removal of unreacted starting material in the following manner. Pooled material (12g.) is dissolved in 100 ml. of absolute ethanol and 25 ml. of water and treated with 4 g. of semicarbazidehydrochloride and 8 g. of sodium acetate at 85°-90° C. for 10 minutes. The resulting solution after standing at ambient temperature for 18 hours is partitioned between water and ether. The combined extracts are washed with water, dried with anhydrous magnesium sulfate and taken to dryness to give 9.6 g. of oily material. The oil is chromatographed on 300 g. of silica gel. Elution with 1200 ml. of 20% ether-in-benzene gives 4.82 g. of product; nmr (COCl$_3$) δ 5.40 (m, 2, trans —C$\underline{H}$=C$\underline{H}$—), 4.13 (q, 2, —OC$\underline{H}_2$CH$_3$), 1.28 (t, 3, o CH$_2$C$\underline{H}_3$) 1.29, 1.16 (s, C$_9$ epimeric-O$\underline{H}$), 0.92 (distorted t, 3, terminal CH$_3$); nmr (CDCl$_3$ with tris(dipavalomethanato)europium added)

two new singlets at δ 4.78 and 4.73 (total of 3 protons, about equally divided), 9-CH₃ epimers.

EXAMPLE 592

9-Hydroxy-9methyl-13-trans-prostenoic acid

A. To a Grignard solution prepared from 670 mg. (3 mol equivalent) of magnesium and 1.73 ml. of methyl iodide in 10 ml. of ether under nitrogen atmosphere is added dropwise a solution of 3 g. of 9-oxo-13-trans-prostenoic acid (Example 140) in 15 ml. of ether and the resulting pasty solution is stirred at ambient temperature for 30 minutes. Saturated ammonium chloride (50 ml.) is added followed by 15 ml. of water and 50 ml. of ether. The ethereal layer is washed with ammonium chloride solution, water, dried with anhydrous magnesium sulfate and evaporated to give 2.6 g. (83%) of 9-hydroxy-9-methyl-13-trans-prostenoic acid; nmr (CDCl₃) δ 5.70 (s, 2, OH and COOH), 5.40 (m, 2, trans —CH=CH), 1.29, 1.16 (s, C₉ epimeric-OH), 0.91 (t, 3, terminal-CH₃).

B. Purified ethyl 9-hydroxy-9-methyl-13-transprostenoate Example 591 is saponified according to the procedure described in Example 178. There is obtained 1.74 g. (95%) of syrupy product.

EXAMPLE 593

Preparation of ethyl 9-hydroxy-9-phenyl-13-trans-prostenoate

In the manner described above for the preparation of ethyl 9-hydroxy-9-methyl-13-trans-prostenoate (Example 591), treatment of 3 g. of ethyl 9-oxo-13-trans-prostenoate (Example 44) with phenylmagnesium bromide, prepared from 1.5 g. of bromobenzene and 230 mg. of magesium in 25 ml. of ether furnished 3 g. of crude product. Removal of starting ketone by means of its semicarbazone as described above furnishes 1.1 g. (30%) of product; glc of product gave two closely related peaks in the proportion of about 9:1.

EXAMPLE 594

Preparation of 9-hydroxy-9-phenyl-13-trans-prostenoic acid

In the manner described above in Example 140 saponification of 1.1 g. of ester furnishes 815 mg. (79%) of product.

EXAMPLE 595

Preparation of ethyl 9β-hydroxy-8-epi-13-trans-prostenoate

Treatment of 9β-hydroxy-8-epi-13-trans-prostenoic acid (Example 545) with ethanol and p-toluenesulfonic acid, and purification all as described in Example 601 yields the title compound as an oil.

EXAMPLE 596

Preparation of ethyl 9β-mesyloxy-8-epi-13-trans-prostenoate

To a solution of 1.0 g. ethyl 9β-hydroxy-8-epi-13-trans-prostenoate (Example 595) in 5 ml. of dry pyridine cooled to 0° C. is added dropwise 0.344 g. of methanesulfonyl chloride and the mixture is stirred at 0° C. for 2 hours. The mixture is poured onto crushed ice and extracted into ether. The organic phase is washed with cold water and saturated brine, dried (MgSO₄) and evaporated in vacuo to yield the title compound.

EXAMPLE 597

Preparation of ethyl 9α-acetoxy-8-epi-13-trans-prostenoate

A mixture of 1.1 g. of ethyl 9β-mesyloxy-8-epi-13-trans-prostenoate (Example 596) and 0.970 g. of anhydrous tetraethylammonium acetate in 5 ml. of anhydrous 1:1 hexamethylphosphoramide-acetone is stirred at 65° C. for 2 days and then cooled. The mixture is poured into ice water and is extracted into ether. The organic phase is washed with water and saturated brine, dried (MgSO₄) and evaporated in vacuo. The residue is purified by dry column chromatography upon silica gel using 4:1 benzene-ethyl acetate as eluting solvent to yield the title compound.

EXAMPLE 598

Preparation of 9α-hydroxy-8-epi-13-trans-prostenoic acid

A mixture of 0.50 g. of ethyl 9α-acetoxy-8-epi-13-trans-prostenoate (Example 597) and 0.30 g. of potassium hydroxide in 5 ml. of 1:1 aqueous methanol is heated to 75° C. for 24 hours cooled, and partially evaporated in vacuo. The residue is acidified with excess dilute hydrochloric acid and is extracted into ether. The organic phase is washed with water and saturated brine, dried (MgSO₄), and evaporated to yield an oil. The latter is purified by dry column chromatography upon silica gel using 60:40:2 cyclohexane-ethyl acetate-acetic acid to yield the title compound.

EXAMPLE 599

Preparation of dl-9α(hydrogenphthaloyloxy)-13-trans-prostenoic acid

A mixture of 1 g. (3.08 mmol) of dl-9α-hydroxy-13-trans-prostenoic acid (Example 545) 479 mg. (3.04 mmol) of phthalic anhydride in 5 ml. of dry pyridine is stirred under nitrogen, in an oil bath at 110° C. for 3 hours. The still warm solution is then poured onto 10 g. of ice containing 5 ml. conc. hydrochloric acid. The reaction mixture is extracted with diethyl ether and the combined extracts washed with saline, dried over magnesium sulfate and concentrated. The residue is triturated with benzene, the insoluble phthalic acid is filtered and the solvent is evaporated to give 1.395 g. of an oil. The crude product is purified by dry column silica gel chromatography as described in Example 545 to give 1.082 g. of product, Rf 0.27–0.54, as an oil.

EXAMPLE 600

Preparation of (−) bis 1-(−)-α-phenylethylamine salt of dl-9α-(hydrogenphthaloyloxy)-13-trans-prostenoic acid and (+) bis d-(+)-α-phenylethylamine salt of dl-9α-(hydrogenphthaloyloxy)-13-trans-prostenoic acid To a solution of 895 mg. (1.91 mmols) of dl-9α-(hydrogenphthaloyloxy)-13-trans-prostenoic acid in 8 ml. of diethyl ether is added a solution of 464 mg. (3.82 mmol) of (−)-α-phenylethylamine $[\alpha]_D^{20}$ −39° (heat), and is stirred for 1 hour. The reaction mixture is concentrated and the residue is dissolved in a minimum amount of ethyl acetate-chloroform (1:1) and allowed to cool in the ice box for 18 hours. The 1 g. of bis salt which separates is recrystallized three times from acetone to constant melting point and rotation to give 238 mg. of salt, m.p. 108°–109°C. $[\alpha]_D^{25}$ −58° (CHCl₃, C=1.02). The mother liquors are concentrated and the partially active (+) bis salt is decomposed by treating with water, concentrated hydrochloric acid (2:1) to give 323 mg. of the hydrogenphthalate. In the manner described above the hydrogenphthalate is treated with (+)-α-phenylethylamine, $[\alpha]_D^{25}$ + 39° (neat), to give 279 mg. of bis salt. The salt is recrystallized three times from acetone to give 157 mg. of white crystals, m.p. 108°-109° C., $[\alpha]_D^{25}$ = +58° (CHCl₃, C=0.881).

EXAMPLE 601

Preparation of dl-ethyl 9α-hydroxy-13-trans-prostenoate

A solution of 200 mg. (0.0616 mmol) of dl-9α-hydroxy-13-trans-prostenoic acid, 5mg. of p-toluenesulfonic acid monohydrate in 50 ml. of ethanol is hated at reflux for 18 hours. The ethanol is evaporated and the residue is dissolved in ether and the solution is washed with sodium bicarbonate solution, saline, dried over magnesium sulfate and concentrated to give 204 mg. (95%) of an oil IR 3600 cm⁻¹ (hydroxyl) 1740 cm⁻¹ (ester carbonyl) 962 ⁻¹ (trans-vinyl group).

EXAMPLE 602

Preparation of (−)-9α-hydroxy-13-trans-prostenoic acid

A mixture of 0.156 g. of potassium hydroxide and 0.215 g. of the bis 1-(−)-α-methylbenzylamino salt of 9α-hydrogenphthaloyloxy-13-trans-prostenoic acid (Example 600 ) in 2.5 ml. of water is heated to 100° C. for 20 hours, cooled, acidified with excess dilute hydrochloric acid, and extracted eith ether. The organic phase is washed with water and saturated brine, dried (MgSO₄), and evaporated to an oil. The latter is purified by thick layer chromatography on silica gel using 60:40:2 - cyclohexane-ethyl acetate-acetic acid as eluting solvent to yield the title compound, m.p. 31-33° C. (hexane), $[\alpha]_D^{25}$ = +48° (±1) (C = 1.24, CHCl₃).

EXAMPLE 603

Preparation of (+)-9α-hydroxy-13-trans-prostenoic acid

Treatment of the bis d-(+)-α-methylbenzylamine salt of 9α-hydrogenphthaloyloxy-13-trans-prostenoic acid (Example 600 ) with potassium hydroxide in water and purification all as described in the preceding Example 602 yields the tital compound, m.p. 33°-34°(hexane), $[\alpha]_D^{25}$ = +46° (±1) (C = 1.395, CHCl₃).

EXAMPLE 604

Preparation of (+)-9-oxo-13-trans-prostenoic acid

To a solution of 0.100 g. of (−)-9α-hydroxy-13-trans-prostenoic acid in 2 ml. of distilled acetone at 0° C. is added dropwise standard Jones reagent [K. Bowden, I.M. Heilbron, E.R.H. Jones, and B.C.L. Weedon, J. Chem. Soc., 39 (1946)] until a slight excess is obtained. The mixture is hand swirled for 2 minutes and is then treated dropwise with isopropanol to destroy the excess oxidant. The reaction mixture is diluted with water and extracted into methylene chloride. The organic phase is washed with water and saturated brine, dried (MgSO₄0 and evaporated to an oil. The latter is purified by thick layer chromatography upon silica gel using 60:40:2 -cyclohexane-ethyl acetate-acetic acid to yield the title compound as an oil, $[\alpha]_D^{25}$ = +55° (+1) (C= 0.991, CHCl₃).

EXAMPLE 605

Preparation of (−)-9-oxo-13-trans-prostenoic acid

Treatment of (+)-9α-hydroxyprostenoic acid in acetone with Jones reagent and purificaion all as described in the preceding Example 604 yields the title compound as an oil, $[\alpha]_D^{25}$ = −51° (±1) (C = 1.11, CHCl₃).

EXAMPLE 606

Preparation of (+)−ethyl 9α-(−)α-methoxy-α-trifluoromethylphenylacetoxy)-13-trans-prestenoate and (−)-ethyl 9α-((−) α-methoxy-α-trifluoromethylphenylacetoxy)-13-trans-prostenoate (−)-9α-hydroxy-13-trans-prostenoic acid and (+)-9α-hydroxy-13-trans-prostenoic acid To a stirred solution of 234 mg. (0.683 mmol) of dl-ethyl 9α-hydroxy-13-trans-prostenoate (Example 560 ) in 1.5 ml. of dry pyridine, uner nitrogen, is slowly added 217 mg. (0.860 mmol) of (−) (α-methoxy-α-trifluoromethylphenylacetyl chloride [J.A. Dale, D.L. Drill and H.S. Mosher, *J. Org. Chem.*, 34 2543 (1969)] and is allowed to stir at room temperature for 2 hours. The pyridine is removed in vacuo and the residue is partitioned between water and diethyl ether. The organic phase is washed with dilute hydrochloric acid, sodium bicarbonate solution, saline, dried over magnesium sulfate and evaporated. The oil is distilled under reduced pressure to give 188 mg. of dl-ethyl 9α-((+)α-methoxy-α-trifluoromethylphenylacetoxy)-13-trans-prostenoate as a colorless oil, b.p. 180°-190° C. (bath temperature) at 0.8 torr. The latter is separated by thick layer chromatography on silica gel using 1-chlorobutane as eluting solvent and 3 developments to yield (−)-ethyl 9α((−)α-methoxy-α-trifluoromethylphenylacetoxy)-13-trans-prostenoate as the more mobile diastereoisomer, $[\alpha]_D^{25}$ = 19° (C = 1.0, CHCl₃) and (+)-ethyl 9α-((−)α-methoxy-α-trifluoromethylphenylacetoxy)-13-trans-prostenoate as the less mobile diastereoisomer $[\alpha]_D^{25}$ = +3° (C = 1.51, CHCl₃).

Each diastereoisomeric ethyl 9α-((−)α-methoxy-α-trifluroomethylphenylacetoxy)-13-trans-prostenoate is saponified to its coresponding enantiomeric 9α-hydroxy-13-trans-prostenoic acid by refluxing 100 mg. of the diastereoisomer with 300 mg. of potassium hydroxide in 1:1 aqueous methanol for 24 hours, cooling, partially evaporating the solvent in vacuo, acidifying with dilute hydrochloric acid, extracting into ether, washing the organic phase with water and saturated brine, drying with MgSO₄, and evaporating. The residue is purified by thick layer chromatography upon silica gel using 60:40:2 cyclohexane-ethyl acetate-acetate acid as eluting solvent to yield the desired enantiomeric 9α-hydroxy-13-trans-prostenoic acid.

EXAMPLE 607

Preparation of (+)-ethyl 9α((+)-1-phenylethylcarbamoyl)-13-trans-prostenoate and (−)-ethyl 9α-((+)-1-phenylethylcarbamoyl)-13-trans-prostenoate (−)-9α-hydroxy-13-trans-prostenoic acid and (+)-9αhydroxy-13-trans-prostenoic acid Each diastereoisomeric ethyl 9α-((+)-1-phenylethylcarbamoyl)-13-trans-prostenoate is saponified to its corresponding enantiomeric 9α-hydroxy-13-trans-prostenoic acid by refluxing 100 mg. of the diastereoisomer with 300 mg. of potassium hydroxide in 1:1 aqueous methanol for 24 hours, cooling, partially evaporating the solvent in vacuo, acidifying with dilute hydrochloric acid, extracting into ether, washing the organic phase with water and saturated brine, drying with MgSO₄, and evaporating. The residue is purified by thick layer chromatography upon silica gel using 60:40:2 cyclohexaneethyl acetate-acetic acid as eluting solvent to yield the desired enantiomeric 9α-hydroxy-13-trans-prosteoic acid.

EXAMPLE 608

Preparation of (+)-ethyl 9-(L-1:carboxy-1-isobutylmethoxyimino)-13-trans-prostenoate and (−)-ethyl 9-(L-1-carboxy-1-isobutylmethoxyimino)-13-trans-prostenoate (−0-ethyl-9-oxo-13-transprostencate, and (−0-ethyl-9-oxo-13-trans-prostenoate A mixture of 0.460 g. of (±)-ethyl 9-oxo-13-trans-prostenoate, 0.300 g. of L-1-carboxy-1-isobutylmethoxime hydrochloride [E. Testa, B.J.R. Nicolaus, L. Mariani, and G. Pagani, Helv. Chim. Acta, 47 766 (1963)], and 0.7 ml. of pyridine in 10 ml. of methanol is stirred at room temperature for 4 hours and then evaporated in vacuo. The residue is partitioned between water and ether. The organic phase is washed with water and saturated brine, dried (MgSO₄), and evaporated. The residue is subjected to dry column chromatography upon silica gel to afford the title oximes.

Each diastereoicomeric ethyl 9-(L-1-carboxy-1-isobutylmethoximino)-13-trans-protenoate is hydrolyzed to its corresponding enantiomeric ethyl 9-oxo-13-trans-prostenoate by treating 0.100 g. of the diastereoisomeric alkoxime with 0.200 g. of ammonium acetate in 5 ml. of 1:2 aqueous tetrahydrofuran and 0.069 g. of titanium trichloride at 60° C. for 4 hours under an inert atmosphere. The resulting mixture is partitioned between water and ether, and the organic phase is washed with water and saturated brine, dried (MgSO₄), and evaporated. The residue is purified by thick layer chromatography on silica gel using 4:1 benzene-ethyl acetate to yield the enantiomeric ethyl 9-oxo-13-trans-prostenoate as an oil.

EXAMPLES 609–699

Treatment of the prostenoic acids listed in Table XXII below with the listed amine or ammonia by the procedure of Example 258 (for ammonia), 259 (for dibasic amines) and 260 (for monobasic amines) furnishes the product prostenoic acid amides of the table.

TABLE XXII

| Example | Starting prostenoic acid of Example | Amine | Product Prostenoic Acid Amide |
| --- | --- | --- | --- |
| 609 | 457 | 4-methylpiperazine | 4-methylpiperazine amide of 1-9-oxo-5-cis,13-trans-prostadienoic acid |
| 610 | 457 | pyrrolidine | pyrrolidine amide of 1-9-oxo-5-cis,13-trans-prostadienoic acid |
| 611 | 457 | morpholine | morpholine amide of 1-9-oxo-5-cis,13-trans-prostadienoic acid |
| 612 | 457 | piperidine | piperidine amide of 1-9-oxo-5-cis,13-trans-prostadienoic acid |
| 613 | 457 | ammonia | 1-9-oxo-5-cis,13-trans-prostadienamide |
| 614 | 457 | dimethylamine | N,N-dimethyl-1-9-oxo-5-cis,13-trans-prostadienamide |
| 615 | 457 | 2-hydroxyethyl-amine | N-(2-hydroxyethyl)-1-9-oxo-5-cis,13-trans-prostadienamide |
| 616 | 457 | 3-hydroxypropyl-amine | N-(3-hydroxypropyl)-1-9-oxo-5-cis,13-trans-prostadienamide |
| 617 | 457 | diethylamine | N,N-diethyl-1-9-oxo-5-cis,13-trans-pro-stadienamide |
| 618 | 457 | 3-dimethylamino-propylamine | N-(3-dimethylaminopropyl)-1-9-oxo-5-cis,13-trans-prostadienamide |
| 619 | 457 | 2-dimethylamino-ethylamine | N-(2-dimethylaminoethyl)-1-9-oxo-5-cis,13-trans-prostadienamide |
| 620 | 457 | ethylamine | N-ethyl-1-9-oxo-5-cis,13-trans-prosta-dienamide |
| 621 | 507 | 4-methylpiperazine | 4-methylpiperazine amide of 9-oxo-2-fluoro-13-trans-prostenoic acid |
| 622 | 507 | dimethylamine | N,N-dimethyl-9-oxo-2-fluoro-13-trans-prostenamide |
| 623 | 509 | morpholine | Morpholine amide of 9-oxo-2-fluoro-17-methyl-18,19,-dinor-13-trans-prostenoic acid |
| 624 | 508 | 2-hydroxyethylamine | N-(2-hydroxyethyl)-9-oxo-2-fluoro-18,19,20-trinor-13-trans-prostenamide |
| 625 | 510 | ammonia | 9-oxo-2-phenyl-13-trans-prostenamide |
| 626 | 511 | 3-dimethylamino-propylamine | N-(3-dimethylaminopropyl)-9-oxo-2-phenyl-18,19,20-trinor-13-trans-prostenamide |
| 627 | 512 | 4-methylpiperazine | 4-methylpiperazine amide of 9-oxo-2-phenyl-17-chloro-18,19,20-trinor-13-trans-prostenoic acid |
| 628 | 513 | pyrrolidine | Pyrrolidine amide of 9-oxo-2-phenyl-17-methyl-19,20-dinor-prostenoic acid |
| 629 | 514 | 3-aminopyridine | N-(pyridyl-3)-9-oxo-2-phenyl-13-trans,17-cis-prostadienamide |
| 630 | 515 | dimethylamine | N,N-dimethyl-9-oxo-2-methyl-13-trans,17-cis-prostadienamide |
| 631 | 516 | 3-dimethylamino-propylamine | N-(3-dimethylaminopropyl)-9-oxo-2-methyl-13-trans-prostenamide |
| 632 | 517 | ammonia | 9-oxo-2-methyl-18,19,20-trinor-13-trans-prostenamide |
| 633 | 518 | morpholine | Morpholine amide of 9-oxo-2-methyl-17-methyl-19,20-dinor-13-trans-prostenoic acid |
| 634 | 519 | 4-methylpiperazine | 4-methylpiperazine amide of 9-oxo-2-methyl-17-chloro-18,19,20-trinor-13-trans-prostenoic acid |
| 635 | 520 | ethylamine | N-ethyl-9-oxo-2-ethyl-18,19,20-trinor-13-trans-prostenamide |

TABLE XXII-continued

| Example | Starting prostenoic acid of Example | Amine | Product Prostenoic Acid Amide |
|---|---|---|---|
| 636 | 521 | 3-aminopyridine | N-(pyridyl-3)-9-oxo-2-ethyl-17-methyl-19,20-dinor-13-trans-prostenamide |
| 637 | 522 | 4-methylpiperazine | 4-methylpiperazine amide of 9-oxo-3,3-dimethyl-18,19,20-trinor-13-trans-prostenoic acid |
| 638 | 522 | morpholine | morpholine amide of 9-oxo-3,3-dimethyl-18,19,20-trinor-13-trans-prostenoic acid |
| 639 | 522 | dimethylamine | N,N-dimethyl-9-oxo-3,3-dimethyl-18,19,20-trinor-13-trans-prostenamide |
| 640 | 523 | 4-methylpiperazine | 4-methylpiperazine amide of 9-oxo-3,3,17-trimethyl-19,20-dinor-13-trans-prostenoic acid |
| 641 | 523 | morpholine | Morpholine amide of 9-oxo-3,3,17-trimethyl-19,20-dinor-13-trans-prostenoic acid |
| 642 | 523 | 2-hydroxyethylamine | N-(2-hydroxyethyl)-9-oxo-3,3,17-trimethyl-19,20-dinor-13-trans-prostenamide |
| 643 | 524 | 3-dimethylaminopropylamine | N-(3-dimethylaminopropyl)-9-oxo-3-oxa-18,19,20-trinor-13-trans-prostenamide |
| 644 | 525 | 2-hydroxyethylamine | N-(2-hydroxyethyl)-9-oxo-3-oxa-17-methyl-19,20-dinor-13-trans-prostenamide |
| 645 | 526 | pyrrolidine | Pyrrolidine amide of 9-oxo-3-thia-17-methyl-19,20-dinor-13-trans-prostenoic acid |
| 646 | 527 | ammonia | 9-oxo-3-thia-18,19,20-trinor-13-trans-prostenamide |
| 646A | 528 | ammonia | 9-oxo-16-phenyl-17,18,19,20-tetranor-13-trans-prostenamide |
| 646B | 528 | 2-hydroxyethylamine | N-(2-hydroxyethyl)-9-oxo-16-phenyl-17,18,19,20-tetranor-13-trans-prostenamide |
| 647 | 530 | dimethylamine | N,N-dimethyl-9-oxo-3-oxa-16-phenyl-17,18,19,20-tetranor-13-trans-prostenamide |
| 648 | 531 | 3-dimethylaminopropylamine | N-(3-dimethylaminopropyl)-9-oxo-3-thia-16-phenyl-17,18,19,20-tetranor-13-trans-prostenamide |
| 649 | 532 | 4-methylpiperazine | 4-methylpiperazine amide of 9-oxo-3,3-dimethyl-16-phenyl-17,18,19,20-tetranor-13-trans-prostenoic acid |
| 650 | 533 | morpholine | Morpholine amide of 9-oxo-2,16-diphenyl-17,18,18,20-tetranor-13-trans-prostenoic acid |
| 651 | 534 | pyrrolidine | Pyrrolidine amide of 9-oxo-2-methyl-16-phenyl-17,18,19,20-tetranor-13-trans-prostenoic acid |
| 652 | 529 | ammonia | 9-oxo-16,20-methano-13-trans-prostenamide |
| 653 | 535 | dimethylamine | N,N-dimethyl-9-oxo-3-oxa-16,20-methano-13-trans-prostenamide |
| 654 | 536 | 3-aminopyridine | N-pyridyl-3)-9-oxo-3-thia-16,20-methano-13-trans-prostenamide |
| 655 | 537 | 3-hydroxypropylamine | N-(3-hydroxypropyl)-9-oxo-3,3-dimethyl-16,20-methano-13-trans-prostenamide |
| 656 | 538 | piperidine | Piperidine amide of 9-oxo-2-phenyl-16,20-methano-13-trans-prostenoic acid |
| 657 | 539 | 4-methylpiperazine | 4-methylpiperazine amide of 9-oxo-2-methyl-16,20-methano-13-trans-prostenoic acid |
| 658 | 540 | Morpholine | Morpholine amide of 9-oxo-2-ethyl-16,20-methano-13-trans-prostenoic acid |
| 659 | 541 | ethylamine | N-ethyl-9-oxo-20-nor-16,20-methano-13-trans-prostenamide |
| 660 | 542 | ammonia | 9-oxo-16,20-ethano-13-trans-prostenamide |
| 661 | 543 | 4-methylpiperazine | 4-methylpiperazine amide of 9-oxo-17-phenyl-18,19,20-trinor-13-trans-prostenoic acid |
| 662 | 543 | homopiperidine | Homopiperidine amide of 9-oxo-17-phenyl-18,19,20-trinor-13-trans-prostenoic acid |
| 663 | 543 | ethylamine | N-ethyl-9-oxo-17-phenyl-18,19,20-trinor-13-trans-prostenamide |
| 664 | 590 | ammonia | 9-methylene-13-trans-prostenamide |
| 665 | 590 | 2-hydroxyethylamine | N-(2-hydroxyethyl)-9-methylene-13-trans-prostenamide |
| 666 | 590 | 3-dimethylaminopropylamine | N-(3-dimethylaminopropyl)-9-methylene-13-trans-prostenamide |
| 667 | 590 | butylamine | N-butyl-9-methylene-13-trans-prostenamide |
| 668 | 590 | ethylamine | N-ethyl-9-methylene-13-trans-prostenamide |
| 669 | 590 | dimethylamine | N,N-dimethyl-9-methylene-13-trans-prostenamide |
| 670 | 590 | pyrrolidine | Pyrrolidine amide of 9-methylene-13-trans-prostenoic acid |
| 671 | 590 | morpholine | Morpholine amide of 9-methylene-13-trans-prostenoic acid |
| 672 | 590 | 4-methylpiperazine | 4-methylpiperazine amide of 9-methylene-13-trans-prostenoic acid |
| 673 | 590A | ammonia | 9-oxo-10-cyano-13-trans-prostenamide |
| 674 | 590A | 2-hydroxyethylamine | N-(2-hydroxyethyl)-9-oxo-10-cyano-13-trans-prostenamide |
| 675 | 590B | dimethylamine | N,N-dimethyl-9-oxo-10-phenyl-13-trans-prostenamide |
| 676 | 590B | morpholine | Morpholine amide of 9-oxo-10-phenyl-13-trans-prostenoic acid |
| 677 | 590C | 4-methylpiperazine | 4-methylpiperazine amide of 9-oxo-10-methyl-13-trans-prostenoic acid |
| 678 | 590C | propylamine | N-propyl-9-oxo-10-methyl-13-trans-prostenamide |

TABLE XXII-continued

| Example | Starting prostenoic acid of Example | Amine | Product Prostenoic Acid Amide |
|---|---|---|---|
| 679 | 590D | 3-dimethylamino-propylamine | N-3-dimethylaminopropyl)-9-oxo-10-methyl-thio-13-trans-prostenamide |
| 680 | 590D | dimethylamine | N,N-dimethyl-9-oxo-10-methylthio-13-trans-prostenamide |
| 681 | 590D | pyrrolidine | Pyrrolidine amide of 9-oxo-10-methylthio-13-trans-prostenoic acid |
| 682 | 590E | morpholine | Morpholine amide of 9-oxo-10-fluoro-13-trans-prostenoic acid |
| 683 | 590E | 3-aminopyridine | N-(pyridyl-3)-9-oxo-10-fluoro-13-trans-prostenamide |
| 684 | 590E | dimethylamine | N,N-dimethyl-9-oxo-10-fluoro-13-trans-prostenamide |
| 685 | 604 | ammonia | Amide of (+) -9-oxo-13-trans-prostenoic acid |
| 686 | 604 | dimethylamine | N,N-dimethyl amide of (+) -9-oxo-13-trans-prostenoic acid |
| 687 | 604 | 4-methylpiperazine | 4-methylpiperazine amide of (+) -9-oxo-13-trans-prostenoic acid |
| 688 | 604 | morpholine | Morpholine amide of (+) -9-oxo-13-trans-prostenoic acid |
| 689 | 604 | pyrrolidine | Pyrrolidine amide of (+) -9-oxo-13-trans-prostenoic acid |
| 690 | 604 | 3-aminopyridine | 3-aminopyridine amide of (+) -9-oxo-13-trans-prostenoic acid |
| 691 | 604 | 2-hydroxyethyl-amine | 2-hydroxyethyl amide of (+) -9-oxo-13-trans-prostenoic acid |
| 692 | 604 | 3-dimethylamino-propylamine | 3-dimethylaminopropyl amide of (+) -9-oxo-13-trans-prostenoic acid |
| 693 | 605 | ammonia | Amide of (−) -9-oxo-13-trans-prostenoic acid |
| 694 | 605 | methylamine | Methylamide of (−) -9-oxo-13-trans-prostenoic acid |
| 695 | 605 | diethylamine | Diethyl amide of (−) -9-oxo-13-trans-prostenoic acid |
| 696 | 605 | 2-hydroxyethylamine | 2-hydroxyethyl amide of (−) -9-oxo-13-trans-prostenoic acid |
| 697 | 605 | 4-methylpiperazine | 4-methylpiperazine amide of (−) -9-oxo-13-trans-prostenoic acid |
| 698 | 605 | morpholine | Morpholine amide of (−) -9-oxo-13-trans-prostenoic acid |
| 699 | 605 | piperidine | Piperidine amide of (−) -9-oxo-13-trans-prostenoic acid |

EXAMPLES 700–737

By the procedure of Example 259, with the substitution of the appropriate hydrazine for 3-dimethylamino-propylamine, the prostenoic acids listed below in Table XXIII below are converted to the corresponding hydrazide products of the table.

TABLE XXIII

| Example | Starting prostenoic acid of Example | Hydrazine Reagent | Product Prostenoic Acid Hydrazide |
|---|---|---|---|
| 700 | 457 | hydrazine | 1-N-amino-9-oxo-5-cis,13-trans-prosta-dienamide |
| 701 | 457 | 1,1-dimethylhydrazine | 1-N-dimethylamino-9-oxo-5-cis,13-trans-prostadienamide |
| 702 | 507 | 1,1-diethylhydrazine | N-diethylamino-9-oxo-2-fluoro-13-trans-prostadienamide |
| 703 | 510 | hydrazine | N-amino-9-oxo-2-phenyl-13-trans-prostenamide |
| 704 | 511 | 1,1-dimethylhydrazine | N-dimethylamino-9-oxo-2-phenyl-18,19,20-trinor-13-trans-prostenamide |
| 705 | 512 | 1-aminopiperidine | N(1-piperidyl)-9-oxo-2-phenyl-17-chloro-18,19,20-trinor-13-trans-prostenamide |
| 706 | 513 | 1-amino-4-methyl-piperazine | N-(4-methylpiperazino)-9-oxo-2-phenyl-17-methyl-19,20-dinor-13-trans-prostenamide |
| 707 | 514 | phenylhydrazine | N-anilino-9-oxo-2-phenyl-13-trans,17-cis-prostadienamide |
| 708 | 515 | 1,1-dimethylhydrazine | N-dimethylamino-9-oxo-2-methyl-13-trans,17-cis-prostadienamide |
| 709 | 516 | hydrazine | N-amino-9-oxo-2-methyl-13-trans-prostenamide |
| 710 | 517 | 1-aminomorpholine | N-morpholino-9-oxo-2-methyl-18,19,20-trinor-13-trans-prostenamide |
| 711 | 518 | 1-aminopiperidine | N-piperidino-9-oxo-2-methyl-17-methyl-19,20-dinor-13-trans-prostenamide |
| 712 | 519 | 1,1-diethylhydrazine | N-diethylamino-9-oxo-2-methyl-17-chloro-18,19,20-trinor-13-trans-prostenamide |
| 713 | 520 | phenylhydrazine | N-anilino-9-oxo-2-ethyl-18,19,20-trinor-13-trans-prostenamide |
| 714 | 523 | 1,1-dimethylhydrazine | N-dimethylamino-9-oxo-3,3,17-trimethyl-19,20-13-dinor-13-trans-prostenamide |
| 715 | 528 | hydrazine | N-amino-9-oxo-16-phenyl-17,18,19,20-tetranor-13-trans-prostenamide |
| 716 | 530 | 1,1-dimethylhydrazine | N-dimethylamino-9-oxo-3-oxa-16-phenyl-17,18,19,20-tetranor-13-trans-prostenamide |
| 717 | 531 | phenylhydrazine | N-anilino-9-oxo-3-thia-16-phenyl-17,18,19,20-tetranor-13-trans-prostenamide |

TABLE XXIII-continued

| Example | Starting prostenoic acid of Example | Hydrazine Reagent | Product Prostenoic Acid Hydrazide |
|---|---|---|---|
| 718 | 532 | 1-aminopiperidine | N-(1-piperidyl)-9-oxo-3,3-dimethyl-16-phenyl-17,18,19,20-tetranor-13-trans-prostenamide |
| 719 | 533 | 1-aminomorpholine | N-morpholino-9-oxo-2,16-diphenyl-17,18,19,20-tetranor-13-trans-prostenamide |
| 720 | 534 | 1,1-diethylhydrazine | N-diethylamino-9-oxo-2-methyl-16-phenyl-17,18,19,20-tetranor-13-trans-prostenamide |
| 721 | 529 | hydrazine | N-amino-9-oxo-16,20-methano-13-trans-prostenamide |
| 722 | 535 | 1,1-dimethylhydrazine | N-dimethylamino-9-oxo-3-oxa-16,20-methano-13-trans-prostenamide |
| 723 | 538 | phenylhydrazine | N-anilino-9-oxo-2-phenyl-16,20-methano-13-trans-prostenamide |
| 724 | 539 | 1,1-dimethylhydrazine | N-dimethylamino-9-oxo-2-methyl-16,20-methano-13-trans-prostenamide |
| 725 | 590 | hydrazine | N-amino-9-methylene-13-trans-prostenamide |
| 726 | 590 | 1,1-dimethylhydrazine | N-dimethylamino-9-methylene-13-trans-prostenamide |
| 727 | 590A | hydrazine | N-amino-9-oxo-10-cyano-13-trans-prostenamide |
| 728 | 590B | 1,1-dimethylhydrazine | N-dimethylamino-9-oxo-10-phenyl-13-trans-prostenamide |
| 729 | 590C | phenylhydrazine | N-anilino-9-oxo-10-methyl-13-trans-prostenamide |
| 730 | 590D | 1-aminopiperidine | N-(piperidyl-1)-9-oxo-10-methylthio-13-trans-prostenamide |
| 731 | 590E | 1,1-dimethylhydrazine | N-dimethylamino-9-oxo-10-fluoro-13-trans-prostenamide |
| 732 | 604 | 1,1-dimethylhydrazine | 2,2-dimethylhydrazide of (+)-9-oxo-13-trans-prostenoic acid |
| 733 | 604 | hydrazine | hydrazide of (+)-9-oxo-13-trans-prostenoic acid |
| 734 | 604 | 1-aminopiperidine | 1-aminopiperidine hydrazide of (+)-9-oxo-13-trans-prostenoic acid |
| 735 | 605 | phenylhydrazine | 2-phenylhydrazide of (−)-9-oxo-13-trans-prostenoic acid |
| 736 | 605 | 1,1-dimethylhydrazine | 2,2-dimethylhydrazide of (−)-9-oxo-13-trans-prostenoic acid |
| 737 | 605 | 1-aminomorpholine | 1-aminomorpholine hydrazide of (−)-9-oxo-13-trans-prostenoic acid |

EXAMPLES 737A–853

Reduction with sodium borohydride in ethanol of the listed 9-oxo-prostenoic acid amides or hydrazides of Table XXIV below by the procedure of Example 367 furnishes the product 9α- and 9β-hydroxy amides or hydrazides of the table. The 9-hydroxy epimers are separable by the usual chromatographic procedures.

Alternatively the 9α-hydroxy epimer may be obtained relatively free of the 9β-epimer if the 9-oxo derivative listed in the table is reduced with lithium(tri-sec-butyl)-borohydride by the procedure described in Example 545 or by the procedure of Example 546 wherein the reducing agent is lithium perhydro-9β-boraphenalylhydride.

Table XXIV

| Example | Starting 9-oxo prostenoic acid amide or hydrazide of Example | Product 9-Hydroxy prostenoic acid amide or hydrazide |
|---|---|---|
| 737A | 609 | 4-methylpiperazine amides of 1-9α-hydroxy and 9β-hydroxy-5-cis,13-trans-prostadienoic acid |
| 737B | 610 | Pyrrolidine amides of 1-9α-hydroxy and 9β-hydroxy-5-cis,13-trans-prostadienoic acid |
| 737C | 611 | Morpholine amides of 1-9α-hydroxy and 9β-hydroxy-5-cis,13-trans-prostadienoic acid |
| 737D | 612 | Piperidine amides of 1-9α-hydroxy and 9β-hydroxy-5-cis,13-trans-prostadienoic acid |
| 738 | 613 | 1-9α-hydroxy and 9β-hydroxy-5-cis,13-trans-prostadienamide |
| 739 | 614 | N,N-dimethyl-1-9α-hydroxy and 9β-hydroxy-5-cis,13-trans-prostadienamide |
| 740 | 615 | N-(2-hydroxyethyl)-1-9α-hydroxy and 9β-hydroxy-5-cis,13-trans-prostadienamide |
| 741 | 616 | N-(3-hydroxypropyl)-1-9α-hydroxy and 9β-hydroxy-5-cis,13-trans-prostadienamide |
| 742 | 617 | N,N-diethyl-1-9α-hydroxy and 9β-hydroxy-5-cis,13-trans-prostadienamide |
| 743 | 618 | N-(3-dimethylaminoproyl)-1-9α-hydroxy and 9β-hydroxy-5-cis,13-trans-prostadienamide |
| 744 | 619 | N-(2-dimethylaminoethyl)-1-9α-hydroxy and 9β-hydroxy-5-cis,13-trans-prostadienamide |
| 745 | 620 | N-ethyl-1-9α-hydroxy and 9β-hydroxy-5-cis,13-trans-prostadienamide |
| 746 | 621 | 4-methylpiperazine amides of 9α-hydroxy and 9β-hydroxy-2-fluoro-13-trans-prostenoic acid |
| 747 | 622 | N,N-dimethyl-9α-hydroxy and 9β-hydroxy-2-fluoro-13-trans-prostenamide |
| 748 | 623 | Morpholine amides of 9α-hydroxy and 9β-hydroxy-2-fluoro-17-meythyl-18,19-dinor-13-trans-prostenoic acid |
| 749 | 624 | N-(2-hydroxyethyl)-9α-hydroxy and 9β-hydroxy-2-fluoro-18,19,20-trinor-13-trans-prostenamide |
| 750 | 625 | 9α-hydroxy and 9β-hydroxy-2-phenyl-13-trans-prostenamide |

– 4,054,604 –

Table XXIV-continued

| Example | Starting 9-oxo prostenoic acid amide or hydrazide of Example | Product 9-Hydroxy prostenoic acid amide or hydrazide |
|---|---|---|
| 751 | 626 | N-(3-dimethylaminopropyl)-9α-hydroxy and 9β-hydroxy-2-phenyl-18,19,20-trinor-13-trans-prostenamide |
| 752 | 627 | 4-methylpiperazine amides of 9α-hydroxy and 9β-hydroxy-2-phenyl-17-chloro-18,19,20-trinor-13-trans-prostenoic acid |
| 753 | 628 | Pyrrolidine amides of 9α-hydroxy and 9β-hydroxy-2-phenyl-17-methyl-19,20-dinor-13-trans-prostenoic acid |
| 754 | 629 | N-(pyridyl-3)-9α-hydroxy and 9β-hydroxy-2-phenyl-13-trans,17-cis-prostadienamide |
| 755 | 630 | N,N-dimethyl-9α-hydroxy and 9β-hydroxy-2-methyl-13-trans,17-cis-prostadienamide |
| 756 | 631 | N-(3-dimethylaminopropyl)-9α-hydroxy and 9β-hydroxy-2-methyl-13-trans-prostenamide |
| 757 | 632 | 9α-hydroxy and 9β-hydroxy-2-methyl-18,19,20-trinor-13-trans-prostenamide |
| 758 | 633 | Morpholine amides of 9α-hydroxy and 9β-hydroxy-2,-17-dimethyl-19,20-dinor-13-trans-prostenoic acid |
| 759 | 634 | 4-methylpiperazine amides of 9α-hydroxy and 9β-hydroxy-2-methyl-17-chloro-18,19,20-trinor-13-trans-prostenoic acid |
| 760 | 635 | N-ethyl-9α-hydroxy and 9β-hydroxy-2-ethyl-18,19,20-trinor-13-trans-prostenamide |
| 761 | 636 | N-(pyridyl-3)-9α-hydroxy and 9β-hydroxy-2-ethyl-17-methyl-19,20-dinor-13-trans-prostenamide |
| 762 | 637 | 4-methylpiperazine amides of 9α-hydroxy and 9β-hydroxy-3,3-dimethyl-18,19,20-trinor-13-trans-prostenoic acid |
| 763 | 638 | Morpholine amides of 9α-hydroxy and 9β-hydroxy-3,3-dimethyl-18,19,20-trinor-13-trans-prostenoic acid |
| 764 | 639 | N,N-dimethyl-9α-hydroxy and 9β-hydroxy-3,3-dimethyl-18,19,20-trinor-13-trans-prostenamide |
| 765 | 640 | 4-methylpiperazine amides of 9α-hydroxy and 9β-hydroxy-3,3,17-trimethyl-19,20-dinor-13-trans-prostenoic acid |
| 766 | 641 | Morpholine amides of 9α-hydroxy and 9β-hydroxy-3,3,17-trimethyl-19,20-dinor-13-trans-prostenoic acid |
| 767 | 642 | N-(2-hydroxyethyl)-9α-hydroxy and 9β-hydroxy-3,3,17-trimethyl-19,20-dinor-13-trans-prostenamide |
| 768 | 643 | N-(3-dimethylaminopropyl)-9α-hydroxy and 9β-hydroxy-3-oxa-18,19,20-trinor-13-trans-prostenamide |
| 769 | 644 | N-(2-hydroxyethyl)-9α-hydroxy and 9β-hydroxy-3-oxa-17-methyl-19,20-dinor-13-trans-prostenamide |
| 770 | 645 | Pyrrolidine amides of 9α-hydroxy and 9β-hydroxy-3-thia-17-methyl-19,20-dinor-13-trans-prostenoic acid |
| 771 | 646 | 9α-hydroxy and 9β-hydroxy-3-thia-18,19,20-trinor-13-trans-prostenamide |
| 772 | 646A | 9α-hydroxy and 9β-hydroxy-16-phenyl-17,18,19,20-tetranor-13-trans-prostenamide |
| 773 | 646B | N-(2-hydroxyethyl)-9α-hydroxy and 9β-hydroxy-16-phenyl-17,18,19,20-tetranor-13-trans-prostenamide |
| 774 | 647 | N,N-dimethyl-9α-hydroxy and 9β-hydroxy-3-oxa-16-phenyl-17,18,19,20-tetranor-13-trans-prostenamide |
| 775 | 648 | N-(3-dimethylaminopropyl)-9α-hydroxy and 9β-hydroxy-3-thia-16-phenyl-17,18,19,20-tetranor-13-trans-prostenamide |
| 776 | 649 | 4-methylpiperazine amides of 9α-hydroxy and 9β-hydroxy-3,3-dimethyl-16-phenyl-17,18,19,20-tetranor-13-trans-prostenoic acid |
| 777 | 650 | Morpholine amides of 9α-hydroxy and 9β-hydroxy-2,16-diphenyl-17,18,19,20-tetranor-13-trans-prostenoic acid |
| 778 | 651 | Pyrrolidine amides of 9α-hydroxy and 9β-hydroxy-2-methyl-16-phenyl-17,18,19,20-tetranor-13-trans-prostenoic acid |
| 779 | 652 | 9α-hydroxy and 9β-hydroxy-16,20-methano-13-trans-prostenamide |
| 780 | 653 | N,N-dimethyl-9α-hydroxy and 9β-hydroxy-3-oxa-16,20-methano-13-trans-prostenamide |
| 781 | 654 | N-(pyridyl-3)-9α-hydroxy and 9β-hydroxy-3-thia-16,20-methano-13-trans-prostenamide |
| 782 | 655 | N-(3-hydroxypropyl)-9α-hydroxy and 9β-hydroxy-3,3-dimethyl-16,20-methano-13-trans-prostenamide |
| 783 | 656 | Piperidine amides of 9α-hydroxy and 9β-hydroxy-2-phenyl-16,20-methano-13-trans-prostenoic acid |
| 784 | 657 | 4-methylpiperazine amides of 9α-hydroxy and 9β-hydroxy-2-methyl-16,20-methano-13-trans-prostenoic acid |
| 785 | 658 | Morpholine amides of 9α-hydroxy and 9β-hydroxy-2-ethyl-16,20-methano-13-trans-prostenoic acid |
| 786 | 659 | N-ethyl-9α-hydroxy and 9β-hydroxy-20-nor-16,20-methano-13-trans-prostenamide |
| 787 | 660 | 9α-hydroxy and 9β-hydroxy-16,20-ethano-13-trans-prostenamide |
| 788 | 661 | 4-methylpiperazine amides of 9α-hydroxy and 9β-hydroxy-17-phenyl-18,19,20-trinor-13-trans-prostenoic acid |
| 789 | 662 | Homopiperidine amides of 9α-hydroxy and 9β-hydroxy-17-phenyl-18,19,20-trinor-13-trans-prostenoic acid |
| 790 | 663 | N-ethyl-9α-hydroxy and 9β-hydroxy-17-phenyl-18,19,20-trinor-13-trans-prostenamide |
| 791 | 673 | 9α-hydroxy and 9β-hydroxy-10-cyano-13-trans-prostenamide |
| 792 | 674 | N-(2-hydroxyethyl)-9α-hydroxy and 9β-hydroxy-10-cyano-13-trans-prostenamide |
| 793 | 675 | N,N-dimethyl-9α-hydroxy and 9β-hydroxy-10-phenyl-13-trans-prostenamide |
| 794 | 676 | Morpholine amides of 9α-hydroxy and 9β-hydroxy-10- |

Table XXIV-continued

| Example | Starting 9-oxo prostenoic acid amide or hydrazide of Example | Product 9-Hydroxy prostenoic acid amide or hydrazide |
|---|---|---|
| | | phenyl-13-trans-prostenoic acid |
| 795 | 677 | 4-methylpiperazine amides of 9α-hydroxy and 9β-hydroxy-10-methyl-13-trans-prostenoic acid |
| 796 | 678 | N-propyl-9α-hydroxy and 9β-hydroxy-10-methyl-13-trans-prostenamide |
| 797 | 679 | N-(3-dimethylaminopropyl)-9α-hydroxy and 9β-hydroxy-10-methylthio-13-trans-prostenamide |
| 798 | 680 | N,N-dimethyl-9α-hydroxy and 9α-hydroxy-10-methylthio-13-trans-prostenamide |
| 799 | 681 | Pyrrolidine amides of 9α-hydroxy and 9β-hydroxy-10-methylthio-13-trans-prostenoic acid |
| 800 | 682 | Morpholine amides of 9α-hydroxy and 9β-hydroxy-10-fluoro-13-trans-prostenoic acid |
| 801 | 683 | N-(pyridyl-3)-9α-hydroxy and 9β-hydroxy-10-fluoro-13-trans-prostenamide |
| 802 | 684 | N,N-dimethyl-9α-hydroxy and 9β-hydroxy-10-fluoro-13-trans-prostenamide |
| 803 | 685 | Amides of (+)-9-oxo-13-trans-prostenoic acid |
| 804 | 686 | N,N-dimethyl amides of (+)-9-oxo-13-trans-prostenoic acid |
| 805 | 687 | 4-methylpiperazine amides of (+)-9α-hydroxy and 9β-hydroxy-13-trans-prostenoic acid |
| 806 | 688 | Morpholine amides of (+)-9α-hydroxy and 9β-hydroxy-13-trans-prostenoic acid |
| 807 | 689 | Pyrrolidine amides of (+)-9α-hydroxy and 9β-hydroxy-13-trans-prostenoic acid |
| 808 | 690 | 3-aminopyridine amides of (+)-9α-hydroxy and 9β-hydroxy-13-trans-prostenoic acid |
| 809 | 691 | 2-hydroxyethyl amides of (+)-9α-hydroxy and 9β-hydroxy-13-trans-prostenoic acid |
| 810 | 692 | 3-dimethylaminopropyl amides of (+)-9α-hydroxy and 9β-hydroxy-13-trans-prostenoic acid |
| 811 | 693 | Amides of (−)-9α-hydroxy and 9β-hydroxy-13-trans-prostenoic acid |
| 812 | 694 | Methyl amides of (−)-9α-hydroxy and 9β-hydroxy-13-trans-prostenoic acid |
| 813 | 695 | Diethyl amides of (−)-9α-hydroxy and 9β-hydroxy-13-trans-prostenoic acid |
| 814 | 696 | 2-hydroxyethyl amides of (−)-9α-hydroxy and 9β-hydroxy-13-trans-prostenoic acid |
| 815 | 697 | 4-methylpiperazine amides of (−)-9α-hydroxy and 9β-hydroxy-13-trans-prostenoic acid |
| 816 | 698 | Morpholine amides of (−)-9α-hydroxy and 9β-hydroxy-13-trans-prostenoic acid |
| 817 | 699 | Piperidine amides of (−)-9α-hydroxy and 9β-hydroxy-13-trans-prostenoic acid |
| 818 | 700 | 1-N-amino-9α-hydroxy and 9β-hydroxy-5-cis,13-trans-prostadienamide |
| 819 | 701 | 1-N-dimethylamino-9α-hydroxy and 9β-hydroxy-5-cis,13-trans-prostadienamide |
| 820 | 702 | N-diethylamino-9α-hydroxy and 9β-hydroxy-2-fluoro-13-trans-prostenamide |
| 821 | 703 | N-amino-9α-hydroxy and 9β-hydroxy-2-phenyl-13-trans-prostenamide |
| 822 | 704 | N-dimethylamino-9α-hydroxy and 9β-hydroxy-2-phenyl-18,19,20-trinor-13-trans-prostenamide |
| 823 | 705 | N-(1-piperidiyl)-9α-hydroxy and 9β-hydroxy-2-phenyl-17-chloro-13-trans-prostenamide |
| 824 | 706 | N-(4-methylpiperazino)-9α-hydroxy and 9β-hydroxy-2-phenyl-17-methyl-19,20-dinor-13-trans-prostenamide |
| 825 | 707 | N-anilino-9α-hydroxy and 9β-hydroxy-2-phenyl-13-trans,-17-cis-prostadienamide |
| 826 | 708 | N-dimethylamino-9α-hydroxy and 9β-hydroxy-2-methyl-13-trans,17-cis-prostadienamide |
| 827 | 709 | N-amino-9α-hydroxy and 9β-hydroxy-2-methyl-13-trans-prostenamide |
| 828 | 710 | N-morpholino-9α-hydroxy and 9β-hydroxy-2-methyl-18,19,20-trinor-13-trans-prostenamide |
| 829 | 711 | N-piperidino-9α-hydroxy and 9β-hydroxy-2,17-dimethyl-19,20-dinor-13-trans-prostenamide |
| 830 | 712 | N-diethylamino-9α-hydroxy and 9β-hydroxy-2-methyl-17-chloro-18,19,20-trinor-13-trans-prostenamide |
| 831 | 713 | N-anilino-9α-hydroxy and 9β-hydroxy-2-ethyl-18,19,20-trinor-13-trans-prostenamide |
| 832 | 714 | N-dimethylamino-9α-hydroxy and 9β-hydroxy-3,3,17-trimethyl-19,20-dinor-13-trans-prostenamide |
| 833 | 715 | N-amino-9α-hydroxy and 9β-hydroxy-16-phenyl-17,18,19,20-tetranor-13-trans-prostenamide |
| 834 | 716 | N-dimethylamino-9α-hydroxy and 9β-hydroxy-3-oxa-16-phenyl-17,18,19,20-tetranor-13-trans-prostenamide |
| 835 | 717 | N-anilino-9α-hydroxy and 9β-hydroxy-3-thia-16-phenyl-17,18,19,20-tetrano-13-trans-prostenamide |
| 836 | 718 | N-(1-piperidyl)-9α-hydroxy and 9β-hydroxy-3,3-dimethyl-16-phenyl-17,18,19,20-tetranor-13-trans-prostenamide |
| 837 | 719 | N-morpholino-9α-hydroxy and 9β-hydroxy-2,16-diphenyl-17,18,19,20-tetranor-13-trans-prostenamide |
| 838 | 720 | N-diethylamino-9α-hydroxy and 9β-hydroxy-2-methyl-16-phenyl-17,18,19,20-tetranor-13-trans-prostenamide |
| 839 | 721 | N-amino-9α-hydroxy and 9β-hydroxy-16,20-methano-13-trans-prostenamide |
| 840 | 721 | N-dimethylamino-9α-hydroxy and 9β-hydroxy-3-oxa-16,20- |

Table XXIV-continued

| Example | Starting 9-oxo prostenoic acid amide or hydrazide of Example | Product 9-Hydroxy prostenoic acid amide or hydrazide |
|---|---|---|
| | | methano-13-trans-prostenamide |
| 841 | 723 | N-anilino-9α-hydroxy and 9β-hydroxy-2-phenyl-16,20-methano-13-trans-prostenamide |
| 842 | 724 | N-dimethylamino-9α-hydroxy and 9β-hydroxy-2-methyl-16,20-methano-13-trans-prostenamide |
| 843 | 727 | N-amino-9-oxo-10-cyano-13-trans-prostenamide |
| 844 | 728 | N-dimethylamino-9-oxo-10-phenyl-13-trans-prostenamide |
| 845 | 729 | N-anilino-9-oxo-10-methyl-13-trans-prostenamide |
| 846 | 730 | N-(piperidyl-1)-9-oxo-10-methylthio-13-trans-prostenamide |
| 847 | 731 | N-dimethylamino-9-oxo-10-fluoro-13-trans-prostenamide |
| 848 | 732 | 2,2-dimethylhydrazide of (+)-9-oxo-13-trans-prostenoic acid |
| 849 | 733 | Hydrazide of (+)-9-oxo-13-trans-prostenoic acid |
| 850 | 734 | 1-aminopiperidine hydrazide of (+)-9-oxo-13-trans-prostenoic acid |
| 851 | 735 | 2-phenylhydraizde of (−)-9-oxo-13-trans-prostenoic acid |
| 852 | 736 | 2,2-dimethylhydrazide of (−)-9-oxo-13-trans-prostenoic acid |
| 853 | 737 | 1-aminomorpholine hydrazide of (−)-9-oxo-13-trans-prostenoic acid |

We claim:

1. A racemic compound consisting of enantiomers of the formulae:

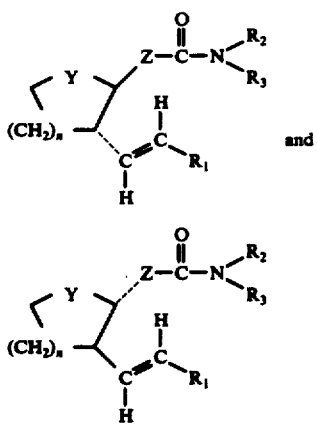

wherein $n$ is an integer from 1 to 2, inclusive; Y is a divalent radical selected from the group consisting of those of the formulae:

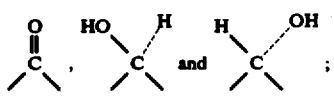

Z is a divalent radical selected from the group consisting of those of the formulae:

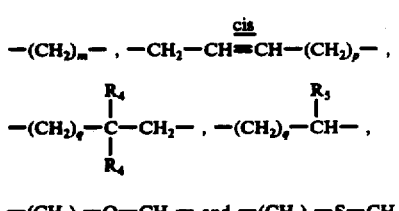

wherein $m$ is an integer from 1 to 8, inclusive, $p$ is an integer from 2 to 4, inclusive, $q$ is an integer from 3 to 6, inclusive, $R_4$ is an alkyl group having from 1 to 3 carbon atoms, and $R_5$ is a lower alkyl group, phenyl or fluoro; $R_1$ is selected from the group consisting of a straight chain alkyl group having from 3 to 10 carbon atoms, a straight chain alkyl group having from 3 to 6 carbon atoms and having one branched lower alkyl group, a straight chain alkenyl group having from 3 to 6 carbon atoms, a straight chain ω-haloalkyl group having from 3 to 6 carbon atoms, a straight ω-phenylalkyl group having from 1 to 4 carbon atoms in the chain, a straight chain ω-(cycloalkyl)alkyl group having from 1 to 4 carbon atoms in the chain and from 5 to 7 carbon atoms in cycloalkyl, and moieties of the formulae:

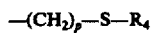

where $p$ and $R_4$ are as hereinabove defined; $R_2$ is selected from the group consisting of hydrogen, lower alkyl, lower alkenyl, lower alkynyl, cyclohexyl, phenyl lower alkyl and ω-hydroxy lower alkyl; $R_3$ is selected from the group consisting of hydrogen, lower alkyl, lower alkenyl, lower alkynyl, cyclohexyl, phenyl, trifluoromethylphenyl, di(lower alkyl)aminophenyl, chlorophenyl, lower alkylphenyl, phenyl lower alkyl, ω-hydroxy lower alkyl, ω-lower alkoxy lower alkyl, ω-di(lower alkyl)amino lower alkyl, amino, and di(lower alkyl)amino; and the pharmaceutically acceptable anionic salts thereof when $R_3$ contains a basic nitrogen atom.

2. A racemic compound consisting of enantiomers of the formulae:

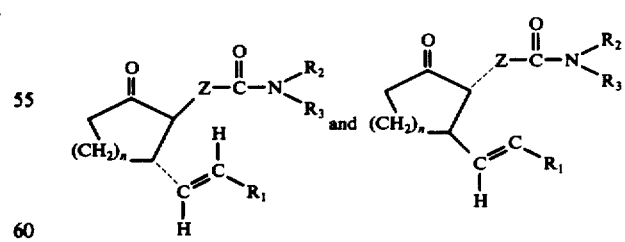

wherein $n$ is an integer from 1 to 2, inclusive; Z is a divalent radical selected from the group consisting of those of the formulae:

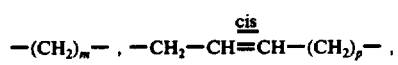

-continued

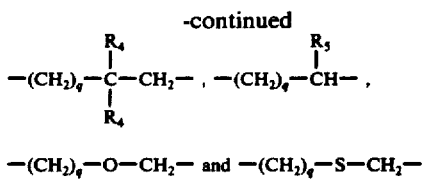

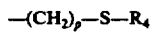

wherein m is an integer from 1 to 8, inclusive, p is an integer from 2 to 4, inclusive, q is an integer from 3 to 6, inclusive, and $R_4$ is an alkyl group having from 1 to 3 carbon atoms, and $R_5$ is a lower alkyl group, phenyl or fluoro; $R_1$ is selected from the group consisting of a straight chain alkyl group having from 3 to 10 carbon atoms, a straight chain alkyl group having from 3 to 6 carbon atoms and having one branched lower alkyl group, a straight chain alkenyl group having from 3 to 6 carbon atoms, a straight chain ω-haloalkyl group having from 3 to 6 carbon atoms, a straight chain ω-phenylalkyl group having from 1 to 4 carbon atoms in the chain, a straight chain ω-(cycloalkyl)alkyl group having from 1 to 4 carbon atoms in the chain and from 5 to 7 carbon atoms in cycloalkyl, and moieties of the formulae:

$$-(CH_2)_p-S-R_4$$

wherein p and $R_4$ are as hereinabove defined; $R_2$ is selected from the group consisting of hydrogen, lower alkyl, lower alkenyl, lower alkynyl, cyclohexyl, phenyl lower alkyl, and ω-hydroxy lower alkyl; $R_3$ is selected from the group consisting of hydrogen, lower alkyl, lower alkenyl, lower alkynyl, cyclohexyl, phenyl, trifluoromethylphenyl, di(lower alkyl)aminophenyl, chlorophenyl, lower alkylphenyl, phenyl lower alkyl, ω-hydroxy lower alkyl, ω-lower alkoxy lower alkyl, ω-di(lower alkyl)amino lower alkyl amino and di(lower alkyl)amino; and the pharmaceutically acceptable anionic salts thereof when $R_3$ contains a basic nitrogen atom.

3. The racemic compound according to claim 2 wherein n is 1, $R_1$ is n-hexyl, $R_2$ is hydrogen, $R_3$ is 3-dimethylaminopropyl, and Z is $-(CH_2)_6-$; N-(3-dimethylaminopropyl)-9-oxo-13-trans-prostenamide.

4. The racemic compound according to claim 2 wherein n is 1, $R_1$ is n-hexyl, $R_2$ is hydrogen, $R_3$ is β-hydroxyethyl, and Z is $-(CH_2)_6-$; N-β-hydroxyethyl amide of 9-oxo-13-trans-prostenoic acid.

5. The racemic compound according to claim 2 wherein n is 1, $R_1$ is n-hexyl, $R_2$ is hydrogen, $R_3$ is 3-dimethylaminopropyl, and Z is

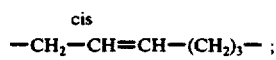

N-(3-dimethylaminopropyl)-9-oxo-5-cis-13-trans-prostadieneamide.

6. The racemic compound according to claim 2 wherein n is 1, $R_1$ is n-hexyl, $R_2$ is hydrogen, $R_3$ is hydrogen, and Z is $-(CH_2)_4-C(CH_3)_2-CH_2-$; 9-oxo-3,3-dimethyl-13-trans-prostenemide.

7. The racemic compound according to claim 2 wherein n is 1, $R_1$ is n-hexyl, $R_2$ is hydrogen, $R_3$ is 3-dimethylaminopropyl, and Z is $-(CH_2)_4-O-CH_2-$; N-(3-diethylaminopropyl)-3-oxa-9-oxo-13-trans-prostenamide.

8. The racemic compound according to claim 2 wherein n is 1, $R_1$ is 6-chlorohexyl, $R_2$ is hydrogen, $R_3$ is amino, and Z is $-(CH_2)_4-C(CH_3)_2-CH_2-$; N-amino-20-chloro-3,3-dimethyl-9-oxo-13-trans-prostenamide.

9. The racemic compound according to claim 2 wherein in n is 2, $R_1$ is n-hexyl, $R_2$ is hydrogen, $R_3$ is 3-dimethylaminopropyl, and Z is $-(CH_2)_6-$; N-(3-dimethylaminopropyl)-9-oxo-10a-homo-13-trans-prostenamide.

10. A racemic compound consisting of enantiomers of the formulae:

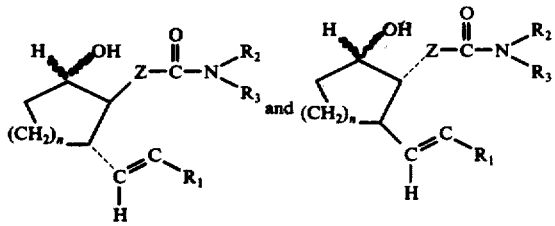

wherein n is an integer from 1 to 2, inclusive; Z is a divalent radical selected from the group consisting of those of the formulae:

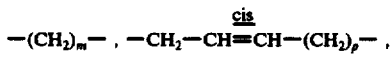

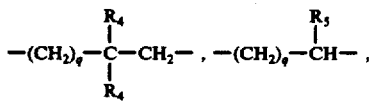

wherein m is an integer from 1 to 8 inclusive, p is an integer from 2 to 4, inclusive, q is an integer from 3 to 6, inclusive, $R_4$ is an alkyl group having from 1 to 3 carbon atoms, and $R_5$ is a lower alkyl group, phenyl or fluoro; $R_1$ is selected from the group consisting of a straight chain alkyl group having from 3 to 10 carbon atoms, a straight chain alkyl group having from 3 to 6 carbon atoms and having one branched lower alkyl group, a straight chain alkenyl group having from 3 to 6 carbon atoms, a straight chain ω-haloalkyl group having from 3 to 6 carbon atoms, a straight chain ω-phenylalkyl group having from 1 to 4 carbon atoms in the chain, a straight chain ω-(cycloalkyl)alkyl group having from 1 to 4 carbon atoms in the chain and from 5 to 7 carbon atoms in cycloalkyl, and moieties of the formulae:

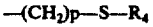

wherein p and $R_4$ are as hereinabove defined; $R_2$ is selected from the group consisting of hydrogen, lower alkyl, lower alkenyl, lower alkynyl, cyclohexyl, phenyl lower alkyl and ω-hydroxy lower alkyl; $R_3$ is selected from the group consisting of hydrogen, lower alkyl, lower alkenyl, lower alkynyl, cyclohexyl, phenyl, trifluoromethylphenyl, di(lower alkyl)aminophenyl, chlorophenyl, lower alkylphenyl, phenyl lower alkyl, ω-hydroxy lower alkyl, ω-lower alkoxy lower alkyl, ω-di(lower alkyl)amino lower alkyl, amino, and di(lower alkyl)-amino; and the pharmaceutically acceptable anionic salts thereof when $R_3$ contains a basic nitrogen atom.

11. The racemic compound according to claim 10 wherein n is 1, $R_1$ is n-hexyl, $R_2$ is hydrogen, $R_3$ is 3-dimethylaminopropyl, and Z is $-(CH_2)_6-$; N-(3-dimethylaminopropyl)-9-hydroxy-13-trans-prostenamide.

12. The racemic compound according to claim 10 wherein $n$ is 1, $R_1$ is $n$-hexyl, $R_2$ is hydrogen, $R_3$ is 2-dimethylaminoethyl, and Z is —(CH$_2$)$_6$—; N-(2-dimethylaminoethyl)-9-hydroxy-13-trans-prostenamide.

13. The racemic compound according to claim 10 wherein $n$ is 1, $R_1$ is n-hexyl, $R_2$ is hydrogen, $R_3$ is 3-dimethylaminopropyl, and Z is —(CH$_2$)$_4$—O—CH$_2$—; N-(3-diethylaminopropyl)-9 -hydroxy-3-oxa-13-trans-prostenamide.

14. The racemic compound according to claim 10 wherein $n$ is 2, $R_1$ is n-hexyl, $R_2$ is hydrogen, $R_3$ is 3-dimethylaminopropyl, and Z is —(CH$_2$)$_6$—; N-(3-dimethylaminopropyl)—9-hydroxy-10a-homo-13-trans-prostenamide.

15. An enantiomer selected from the group consisting of those of the formulae:

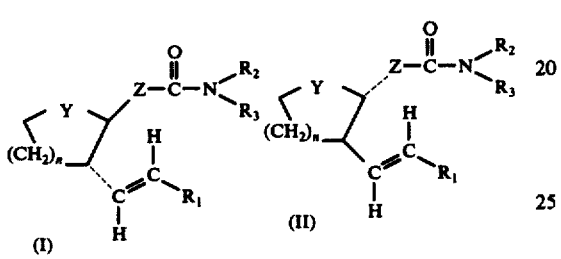

wherein $n$ is an integer from 1 to 2, inclusive; Y is a divalent radical selected from the group consisting of those of the formulae:

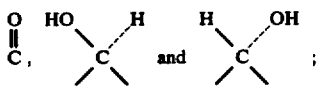

Z is a divalent radical selected from the group consisting of those of the formulae:

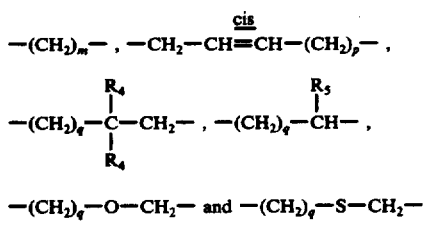

wherein $m$ is in integer from 1 to 8, inclusive, $p$ is an integer from 2 to 4, inclusive, $q$ is an integer from 3 to 6 inclusive, and $R_4$ is an alkyl group having from 1 to 3 carbon atoms, and $R_5$ is a lower alkyl group, phenyl or fluoro; $R_1$ is selected from the group consisting of a straight chain alkyl group having from 3 to 10 carbon atoms, a straight chain alkyl group having from 3 to 6 carbon atoms and having one branched lower alkyl group, a straight chain alkenyl group having from 3 to 6 carbon atoms, a straight chain ω-haloalkyl group having from 3 to 6 carbon atoms, a straight chain ω-phenylalkyl group having from 1 to 4 carbon atoms in the chain, a straight chain ω-(cycloalkyl)alkyl group having from 1 to 4 carbon atoms in the chain and from 5 to 7 carbon atoms in cycloalkyl, and moieties of the formulae:

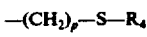

wherein $p$ and $R_4$ are as hereinabove defined; $R_2$ is selected from the group consisting of hydrogen, lower alkyl, lower alkenyl, lower alkynyl, cyclohexyl, phenyl lower alkyl, and ω-hydroxy lower alkyl; $R_3$ is selected from the group consisting of hydrogen, lower alkyl, lower alkenyl, lower alkynyl, cyclohexyl, phenyl, trifluoromethylphenyl, di(lower alkyl)aminophenyl, chlorophenyl, lower alkylphenyl, phenyl lower alkyl, ω-hydroxy lower alkyl, ω-lower alkoxy lower alkyl, ω-di(lower alkyl)amino lower alkyl, amino, and di(lower alkyl)amino; and the pharmaceutically acceptable anionic salts thereof when $R_3$ contains a basic nitrogen atom.

16. An enantiomer selected from the group consisting of those of the formulae:

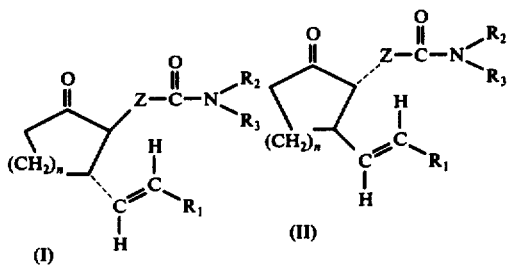

wherein $n$ is an integer from 1 to 2, inclusive; Z is a divalent radical selected from the group consisting of those of the formulae:

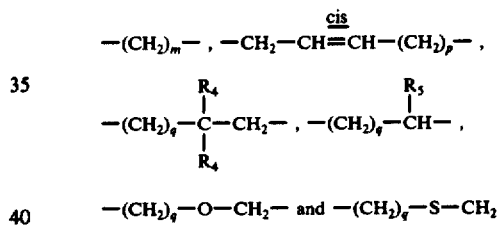

wherein $m$ is an integer from 1 to 8, inclusive, $p$ is an integer from 2 to 4, inclusive, $q$ is in integer from 3 to 6, inclusive, and $R_4$ is an alkyl group having from 1 to 3 carbon atoms, and $R_5$ is a lower alkyl group, phenyl or fluoro; $R_1$ is selected from the group consisting of a straight chain alkyl group having from 3 to 10 carbon atoms, a straight chain alkyl group having from 3 to 6 carbon atoms and having one branched lower alkyl group, a staight chain alkenyl group having from 3 to 6 carbon atoms, a straight chain ω-haloalkyl group having from 3 to 6 carbon atoms, a straight chain ω-phenylaklyl group having from 1 to 4 carbon atoms in the chain, a straight chain ω-(cycloalkyl)alkyl group having from 1 to 4 carbon atoms in the chain and from 5 to 7 carbon atoms in cycloalkyl, and moieties of the formulae:

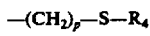

wherein $p$ and $R_4$ are as hereinabove defined; $R_2$ is selected from the group consisting of hydrogen, lower alkyl, lower alkenyl, lower alkynyl, cyclohexyl, phenyl lower alkyl, and ω-hydroxy lower alkyl; $R_3$ is selected from the group consisting of hydrogen, lower alkyl, lower alkenyl, lower alkynyl, cyclohexyl, phenyl, trifluoromethylphenyl, di(lower alkyl)aminophenyl, chlorophenyl, lower alkylphenyl, phenyl lower alkyl, ω- hydroxy lower alkyl, ω-lower alkoxy lower alkyl, ω-di(lower alkyl)amino lower alkyl, amino, and di(lower alkyl)amino; and the pharmaceutically acceptable anionic salts thereof when $R_3$ contains a basic nitrogen atom.

17. The enantiomer according to claim 16, Formula (II) thereof, wherein n is 1, $R_1$ is 3-methyl-n-butyl, $R_2$ is hydrogen, $R_3$ is dimethylamino, Z is —$(CH_2)_4$—C$(CH_3)_2$—$CH_2$—; 1-N-dimethylamino-9-oxo-3,3,17-trimethyl-19,20-dinor-13-trans-prostenamide.

18. An enantiomer selected from the group consisting of those of the formulae:

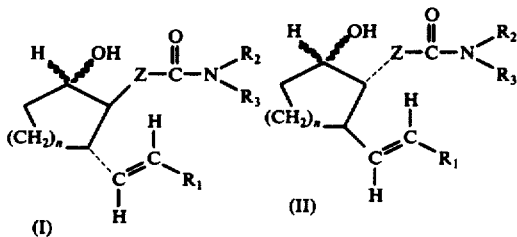

wherein n is an integer from 1 to 2, inclusive; Z is a divalent radical selected from the group consisting of those of th formulae:

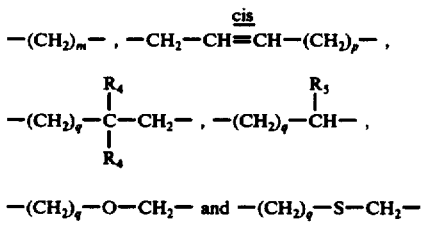

wherein m is an integer from 1 to 8, inclusive, p is an integer from 2 to 4, inclusive, q is an integer from 3 to 6, inclusive, and $R_4$ is an alkyl group having from 1 to 3 carbon atoms, and $R_5$ is a lower alkyl group, phenyl or fluorine; $R_1$ is selected from the group consisting of a straight chain alkyl group having from 3 to 10 carbon atoms, a straight chain alkyl group having from 3 to 6 carbon atoms and having one branched lower alkyl group, a straight chain alkenyl group having from 3 to 6 carbon atoms, a straight chain ω-haloalkyl roup having from 3 to 6 carbon atoms, a straight chain ω-phenylalkyl group having from 1 to 4 carbon atoms in the chain, a straight chain ω-(cycloalkyl)alkyl group having from 1 to 4 carbon atoms in the chain and from 5 to 7 carbon atoms in cycloalkyl, and moieties of the formulae:

$$—(CH_2)_p—S—R_4$$

wherein p and $R_4$ are as hereinabove defined; $R_2$ is selected from the group consisting of hydrogen, lower alkyl, lower alkenyl, lower alkynyl, cyclohexyl, phenyl lower alkyl, and ω-hydroxy lower alkyl; $R_3$ is selected from the group consisting of hydrogen, lower alkyl, lower alkenyl, lower alkynyl, cyclohexyl, phenyl, trifluoromethylphenyl, di(lower alkyl)aminophenyl, chlorophenyl, lower alkylphenyl, phenyl lower alkyl, ω-hydroxy lower alkyl, ω-lower alkoxy lower alkyl, ω-di(lower alkyl)amino lower alky, amino, and di(lower alkyl)amino; and the pharmaceutically acceptable anionic salts thereof when $R_3$ contains a basic nitrogen atom.

19. The enantiomer according to claim 18, Formula (II) thereof, wherein n is 1, $R_1$ is 3-methyl-n-butyl, $R_2$ is hydrogen, $R_3$ is dimethylamino, and Z is —$(CH_2)_6$—; 1-N-dimethylamino-9α-hydroxy-17methyl-19,20-dinor-13-trans-prostenamide.

* * * * *